United States Patent
Bozek et al.

(10) Patent No.: US 11,850,330 B2
(45) Date of Patent: Dec. 26, 2023

(54) BIOPRINTED HAIR FOLLICLES AND USES THEREOF

(71) Applicant: Organovo, Inc., San Diego, CA (US)

(72) Inventors: Emily Bozek, San Diego, CA (US); Jonah Cool, San Diego, CA (US); Harry S. Rapoport, San Diego, CA (US); Christian Holmes, San Diego, CA (US); Stephen L. Pentoney, San Diego, CA (US); Chad Viergever, San Diego, CA (US); Howard Hwang, San Diego, CA (US); Christopher Shaw, San Diego, CA (US)

(73) Assignee: Organovo, Inc., San Diego, CA (US)

(*) Notice: Subject to any disclaimer, the term of this patent is extended or adjusted under 35 U.S.C. 154(b) by 1190 days.

(21) Appl. No.: 16/349,108

(22) PCT Filed: Nov. 10, 2017

(86) PCT No.: PCT/US2017/061029
§ 371 (c)(1),
(2) Date: May 10, 2019

(87) PCT Pub. No.: WO2018/089750
PCT Pub. Date: May 17, 2018

(65) Prior Publication Data
US 2019/0275208 A1    Sep. 12, 2019

Related U.S. Application Data

(60) Provisional application No. 62/420,489, filed on Nov. 10, 2016.

(51) Int. Cl.
| | | |
|---|---|---|
| *A61L 27/60* | (2006.01) | |
| *A61L 27/38* | (2006.01) | |
| *A61L 27/52* | (2006.01) | |
| *C12N 5/071* | (2010.01) | |
| *A61K 35/36* | (2015.01) | |
| *A61K 47/36* | (2006.01) | |
| *A61L 27/24* | (2006.01) | |

(52) U.S. Cl.
CPC ............ *A61L 27/60* (2013.01); *A61K 35/36* (2013.01); *A61K 47/36* (2013.01); *A61L 27/3813* (2013.01); *A61L 27/52* (2013.01); *C12N 5/0626* (2013.01); *C12N 5/0627* (2013.01); *C12N 5/0629* (2013.01); *C12N 5/0697* (2013.01); *A61L 27/24* (2013.01); *C12N 2533/74* (2013.01)

(58) Field of Classification Search
None
See application file for complete search history.

(56) References Cited

U.S. PATENT DOCUMENTS

| | | |
|---|---|---|
| 6,568,787 B1 | 5/2003 | Girones et al. |
| 6,887,490 B1 * | 5/2005 | Jahoda ............... A61P 43/00 424/572 |
| 7,887,843 B2 | 2/2011 | Libera et al. |
| 7,980,645 B2 | 7/2011 | Ohtsuka et al. |
| 8,931,880 B2 | 1/2015 | Murphy et al. |
| 8,980,628 B2 * | 3/2015 | Qiao .................. A61L 27/3886 435/395 |
| 9,149,952 B2 | 10/2015 | Murphy et al. |
| 9,227,339 B2 | 1/2016 | Murphy et al. |
| 9,315,043 B2 | 4/2016 | Murphy et al. |
| 9,321,998 B2 * | 4/2016 | Toyoshima ......... A61L 27/3886 |
| 9,499,779 B2 | 11/2016 | Murphy et al. |
| 9,855,369 B2 | 1/2018 | Murphy et al. |
| 10,174,276 B2 | 1/2019 | Murphy et al. |
| 10,967,560 B2 | 4/2021 | Murphy et al. |
| 11,413,805 B2 | 8/2022 | Murphy et al. |
| 11,529,436 B2 | 12/2022 | Retting et al. |
| 2003/0175410 A1 | 9/2003 | Campbell et al. |
| 2005/0089512 A1 * | 4/2005 | Schlotmann ........ A61L 27/3804 435/371 |
| 2005/0091576 A1 | 4/2005 | Relyea et al. |
| 2007/0258956 A1 | 11/2007 | Higgins et al. |
| 2008/0070304 A1 | 3/2008 | Forgacs et al. |
| 2011/0052693 A1 | 3/2011 | Kao et al. |
| 2012/0276154 A1 | 11/2012 | Mahjour et al. |
| 2013/0078666 A1 | 3/2013 | Stark et al. |
| 2013/0164339 A1 | 6/2013 | Murphy et al. |
| 2013/0190210 A1 | 7/2013 | Murphy et al. |
| 2013/0245544 A1 | 9/2013 | De, Jr. et al. |

(Continued)

FOREIGN PATENT DOCUMENTS

| | | |
|---|---|---|
| CN | 104013999 B | 5/2016 |
| EP | 2674484 A1 | 12/2013 |

(Continued)

OTHER PUBLICATIONS

Dua et al. J Cutan Aesthet Surg. May-Aug. 2010; 3(2): 76-81. (Year: 2010).*

(Continued)

*Primary Examiner* — Allison M Fox

(74) *Attorney, Agent, or Firm* — STERNE, KESSLER, GOLDSTEIN & FOX P.L.L.C.

(57) ABSTRACT

Disclosed are compositions comprising cellular constructs comprising mesenchymal cells and epithelial cells. Also disclosed are methods of making the cellular constructs, methods of hair restoration, and kits. The invention also discloses parallel bio-printing systems and methods for making cellular constructs, such as cellular constructs comprising mesenchymal cells and epithelial cells.

23 Claims, 35 Drawing Sheets

(56) References Cited

U.S. PATENT DOCUMENTS

| | | |
|---|---|---|
| 2015/0004273 A1 | 1/2015 | Forgacs et al. |
| 2015/0037445 A1 | 2/2015 | Murphy et al. |
| 2015/0093932 A1 | 4/2015 | Ning et al. |
| 2015/0139960 A1 | 5/2015 | Tumey et al. |
| 2016/0122723 A1 | 5/2016 | Retting et al. |
| 2016/0184481 A1 | 6/2016 | Thangapazham et al. |
| 2016/0272946 A1 | 9/2016 | Shepherd et al. |
| 2017/0130192 A1 | 5/2017 | Retting et al. |
| 2017/0199507 A1 | 7/2017 | Murphy et al. |
| 2017/0281528 A1 | 10/2017 | Fabrikant |
| 2018/0265839 A1 | 9/2018 | Retting et al. |
| 2018/0313822 A1 | 11/2018 | Murphy et al. |
| 2020/0197152 A1 | 6/2020 | Murphy et al. |
| 2021/0008788 A1 | 1/2021 | Murphy et al. |
| 2021/0123906 A1 | 4/2021 | Murphy et al. |
| 2021/0291432 A1 | 9/2021 | Murphy et al. |
| 2022/0009156 A1 | 1/2022 | Murphy et al. |
| 2022/0009157 A1 | 1/2022 | Murphy et al. |
| 2022/0195380 A1 | 6/2022 | Retting et al. |

FOREIGN PATENT DOCUMENTS

| | | | |
|---|---|---|---|
| JP | 2011092179 A | 5/2011 | |
| JP | 2013542728 A | 11/2013 | |
| JP | 2014204711 A | 10/2014 | |
| WO | WO-2005081970 A2 | 9/2005 | |
| WO | WO-2009107266 A1 | 9/2009 | |
| WO | WO-2010008905 A2 | 1/2010 | |
| WO | WO-2010030964 A2 | 3/2010 | |
| WO | WO 11/094964 * | 8/2011 | ............ C12N 5/04 |
| WO | WO-2012054195 A2 | 4/2012 | |
| WO | WO-2013040078 A2 | 3/2013 | |
| WO | WO-2013040087 A2 | 3/2013 | |
| WO | WO-2013123049 A1 | 8/2013 | |
| WO | WO-2013158508 A1 | 10/2013 | |
| WO | WO-2015017579 A1 | 2/2015 | |
| WO | WO-2016073782 A1 | 5/2016 | |
| WO | WO-2016115034 A1 | 7/2016 | |
| WO | WO-2017083402 A1 | 5/2017 | |

OTHER PUBLICATIONS

Machine translation of WO 11/094964 (Year: 2011).*
Brown TM, Krishnamurthy K. Histology, Dermis. [Updated Nov. 14, 2022]. In: StatPearls [Internet]. Treasure Island (FL): StatPearls Publishing; Jan. 2023—Retrieved from internet Apr. 22, 2023, URL: https://www.ncbi.nlm.nih.gov/books/NBK535346/#_NBK535346_pubdet_(Year: 2022).*
Alonso et al., PNAS, 2003, 100(Suppl 1): 11830-11835. (Year: 2003).*
Higgins, C.A., et al., "Microenvironmental Reprogramming by Three-dimensional Culture Enables Dermal Papilla Cells to Induce De Novo Human Hair-follicle Growth," Proceedings of the National Academy of Sciences of the United States of America 110(49):19679-19688, National Academy of Sciences, United States (Dec. 2013).
International Search Report and Written Opinion for International Application No. PCT/US2017/061029, dated Jan. 23, 2018, 11 pages.
Jaks, V., et al., "The Hair Follicle—a Stem Cell Zoo," Experimental Cell Research 316(8):1422-1428, Academic Press, United States (May 2010).
Mahjour, S.B., et al., "Hair Follicle Regeneration in Skin Grafts: Current Concepts and Future Perspectives," Tissue Engineering. Part B, Reviews 18(1): 15-23, Mary Ann Liebert, United States (Feb. 2012).
Rassman, W.R et al., "Follicular Unit Extraction: Minimally Invasive Surgery for Hair Transplantation," Dermatol. Surgery 28(8):720-727, Wolters Kluwer Health, United States (Aug. 2002).
Sher, D., "L'Oréal Partners with Poietis to Develop 3D Printed Hair Follicles," 3dprintingmedia.network, published Oct. 19, 2016, accessed at https://www.3dprintingmedia.network/loreal-partners-poietis-develop-3d-printed-hair-follicles/, accessed on Jan. 20, 2023, 6 pages.
Unger, W., "Commentary," Dermatol Surgery 28:727-728, Lippincott, Williams & Wilkins, United States (2002).
Extended European Search Report for EP Application No. 17868625, dated Aug. 31, 2020, European Patent Office, Netherlands, 12 pages.
Partial European Search Report for EP Application No. 17868625, dated May 29, 2020, European Patent Office, Netherlands, 16 pages.
Lee, V, et al., "Design and Fabrication of Human Skin by Three-Dimensional Bioprinting," Tissue Engineering: Part C 20(6):473-484, Mary Ann Liebert, Inc., United States (2014).
Michael, S., et al., "Tissue Engineered Skin Substitutes Created by Laser-Assisted Bioprinting Form Skin-Like Structures in the Dorsal Skin Fold Chamber in Mice," PLOS One 8(3):e57741, Scientific Research Publishing Inc., United States 12 pages (2013).
Velasquillo, C., et al., "Skin 3D Bioprinting. Applications in Cosmetology," Journal of Cosmetics, Dermatological Sciences and Applications 3:85-89, Scientific Research Publishing Inc., United States (2013).
Koch, L., et al., "Laser printing of skin cells and human stem cells," Tissue Engineering Part C Methods 16(5):847-854, Mary Ann Liebert, Inc., United States (2010).
Malda, J., et al., "25th anniversary article: Engineering hydrogels for biofabrication," Advanced Materials 25(36):5011-5028, Wiley-VCH, Germay (2013).
Macneil, S., "Progress and opportunities for tissue-engineered skin," Nature 445(7130):874- 880, Nature Publishing Group, England (2007).
Ponec, M., et al., "Endothelial network formed with human dermal microvascular endothelial cells in autologous multicellular skin substitutes," Angiogenesis 7(4):295-305, Springer, Germany (2004).
Pampaloni, F. and Stelzer, E.H.K., "Three-Dimensional Cell Cultures in Toxicology," Biotechnology and Genetic Engineering Reviews 26:117-138, Taylor & Francis, England (2009).
Dababneh, A.B., et al., "Bioprinting Technology: A Current State-of-the-Art Review," Journal of Manufacturing Science and Engineering 136(6):061016/1-061016/11, The American Society of Mechanical Engineers, United States (2014).
Koch, L. et al., "Skin Tissue Generation by Laser Cell Printing," Biotechnology and Bioengineering 109(7): 1855-1863, Wiley and Sons, United States (2012).
Rimann, et al., "Additive Verfahren mit biologischen Materialien," cited in NPL23 as Orthopaede vol. 46, Aug. 24, 2014.
Rimann, et al., "Skin bioprinting: an innovative approach to produce standardized skin models on demand," cited in NPL23 as CTI Medtech Event 2012, Luzern, Switzerland, Sep. 24, 2012, retrieved on Apr. 18, 2018 from https://www.zhaw.ch/storage/lsfm/institute-zentren/icbt/tedd/bioprinting-poster.pdf.
Young-Joon, S. et al., "Bioprinting technology and its applications," Eur J of Cardio-Thoracic Surgery 46(3):342-348, Oxford University Press, England (2014).
Extended European Search Report for EP Application No. EP 15857287.5, Munich, Germany, dated May 3, 2018, 8 pages.
Auxenfans, C., et al., "Evolution of three dimensional skin equivalent models reconstructed in vitro by tissue engineering," Eur. J. Dermatol. 19(2): 107-113, John Libbey Eurotext, France (2009).
Furukawa, K.S., et al., "Tissue-engineered skin using aggregates of normal human skin fibroblasts and biodegradable material," J. Artif. Organs 4:353-356, Springer, Germany (2001).
Lee, W., et al. "Multi-layered culture of human skin fibroblasts and keratinocytes through three-dimensional freeform fabrication," Biomaterials 30:1587-1595, Elsevier Science, Netherlands (2009).
Co-Pending U.S. Appl. No. 18/068,137, filed Dec. 19, 2022, inventor Murphy, Keith, et al. (Unpublished).

* cited by examiner

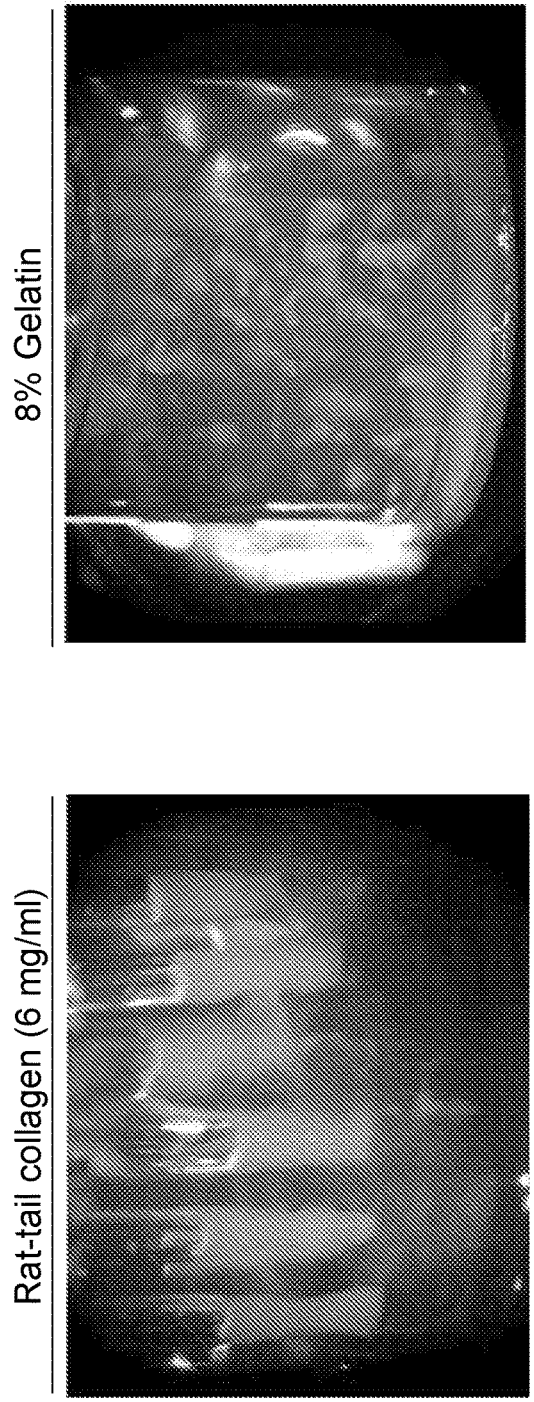
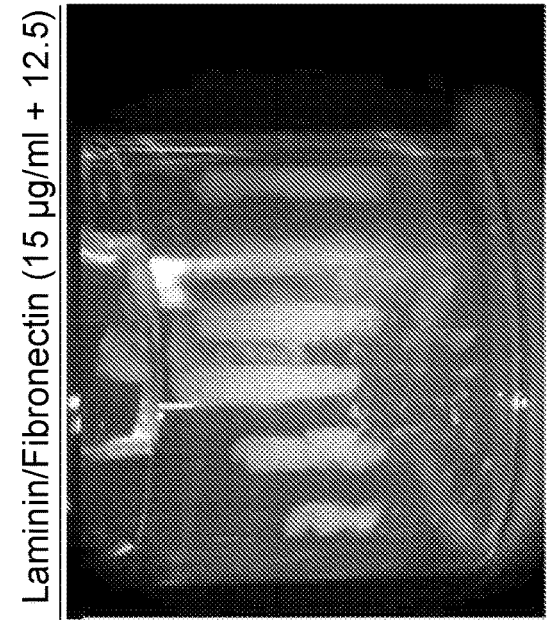
FIG. 6A
FIG. 6B
FIG. 6C

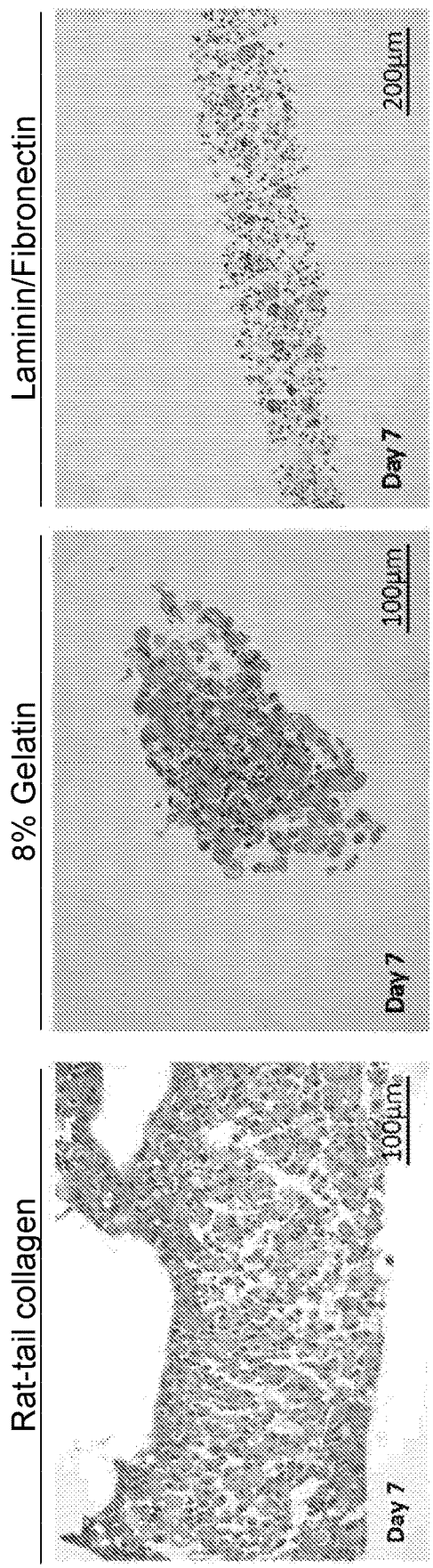
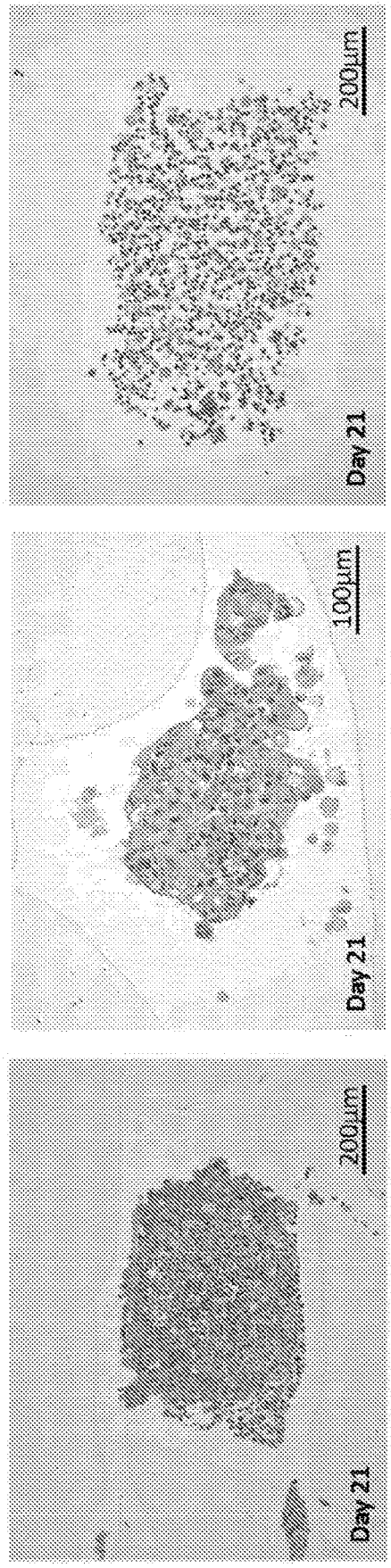
FIG. 7A  FIG. 7C  FIG. 7E
FIG. 7B  FIG. 7D  FIG. 7F

Scale Bars = 100 μm

BrdU/CK6

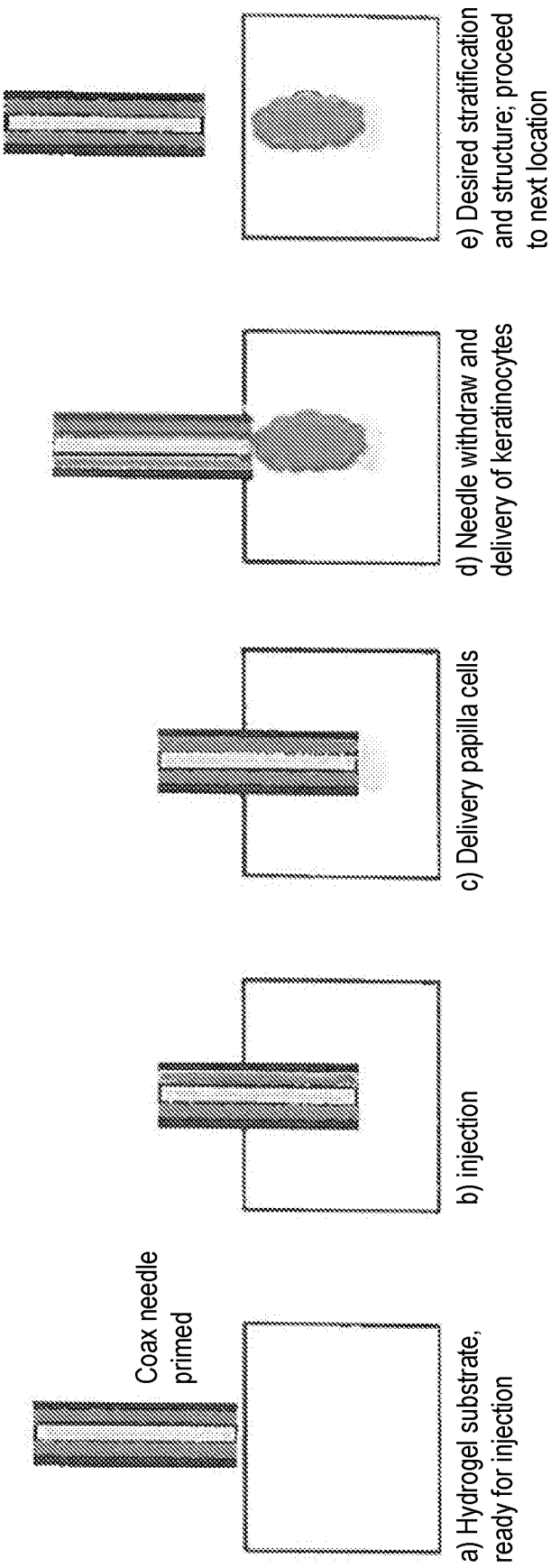

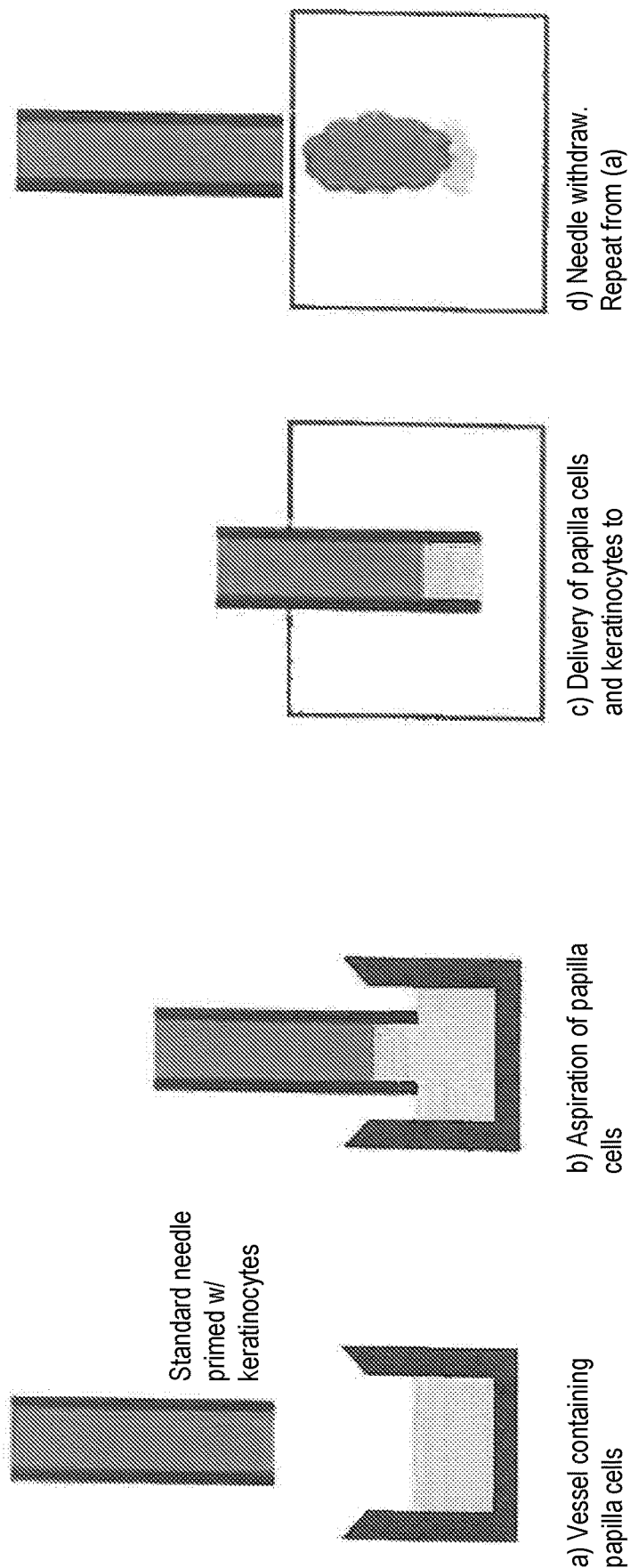

BIOPRINTED HAIR FOLLICLES AND USES THEREOF

BACKGROUND OF THE INVENTION

Field of the Invention

The invention is in the field of hair transplant compositions and methods. In particular, the present invention provides compositions comprising cellular constructs comprising mesenchymal cells and epithelial cells. The invention also provides methods of making the cellular constructs, methods of hair restoration, and kits. The invention also discloses parallel bio-printing systems and methods for making cellular constructs using the parallel bio-printing system, such as cellular constructs comprising mesenchymal cells and epithelial cells.

Background Art

Modern hair transplantation began in the 1950s when hair follicles were harvested using 4-mm punches. The punch size was gradually reduced to enhance graft survival and to make the transplanted hair look more natural. Micrografting—the use of a large number of small grafts harvested with a multi-bladed knife—then became the standard for hair transplantation in the early 1990s. Punch harvesting was then abandoned in favor of donor strip excision to maximize yield and minimize damage to the donor follicles. A significant disadvantage to single strip harvesting was the resulting donor scar. Such a scar presented cosmetic issues in patients who choose to wear their hair very short or in patients who heal with a widened scar. Single strip harvesting sometimes was also problematic in patients with very tight scalps where a primary closure was difficult. See, Rassman et al., *Dermatol. Surg.* 28:720-727 (2002).

In an effort to overcome the disadvantages of single strip harvesting of hair follicles, Rassman et al. (2002) developed follicular unit extraction (FUE) in which individual follicular units (FUs) were removed directly from the donor through very small punch incisions. There were a number of significant disadvantages to FUE including (1) donor area damage (the excision of FUs involved a tremendous increase in the total length of the incisions compared to conventional strip harvesting), (2) cosmetic factors (large areas of the donor area had to be clipped short in preparation for FUE in order to find a significant number of FU that were suitable for extraction, presenting a "significant post-op cosmetic problem"), (3) follicle damage (more FUs were damaged than expected with conventional harvesting), (4) distortion of follicle direction (when the small donor sites healed, they created scars that distorted the hair direction or angle of adjacent FU), (5) increased risk of infection (if additional FUE procedures were done one or a few days apart in order to avoid distortion of follicle direction, there was almost certainly a greater likelihood of bacterial pathogens being present in the donor area), and (6) increased operating time (FUE was far more time consuming than conventional harvesting). See, Unger, W., "Commentary," *Dermatol. Surg.* 28:727-728 (2002).

An alternative to FUE is de novo engineering of human hair follicles. Work over the past 2-3 decades has narrowed down the critical cells involved in hair formation to a mesenchymal population comprising dermal papilla cells and overlying epithelial keratinocytes. Subsequent work established that dermal papilla cells are strictly required for inducing keratinocytes to form the hair sheath and shaft. Initial reconstitution experiments were done with rodent cells but did not immediately translate to successful hair growth when comparable human cells were tested. This highlights species specific differences in hair formation. It has been found that aggregating human dermal papilla cells into 3D spheroids partially restored the intact dermal papilla gene-expression signature within the cells and, in turn, their associated hair-inducing properties. Use of spheroid culture was deemed to be necessary, but two of seven cell lines failed to promote neohairs in recipient skin and the hair follicles that did grow were small and often failed to produce hair fibers that exited the skin surface. Higgins et al., *PNAS* 110:19679-88 (2013).

Accordingly, there is need in the art for new methods of de novo generation of hair follicles that overcome the prior disadvantages. The present invention overcomes these disadvantages and provides a near unlimited supply of FUs for transplantation and treatment of hair loss. The present invention further provides a parallel bio-printing system and corresponding methods of using the parallel bio-printing system to make cellular constructs. Unlike conventional three-dimensional printing materials such as thermoplastics that are essentially fixed once they are printed, bioinks may have a fluid dynamic nature and thus, have a tendency to flow after bio-printing. An approach to deal with the dynamic nature of bioinks is to bio-print into a support material, such as a semi-solid material. The support material can limit the flow of the bio-printed bio-inks. As a result, thin vertical structures that normally lack the integrity to hold its shape after bio-printing can become possible. However, this approach presents a technical problem when two materials, such as two separate bio-inks, must be bio-printed differentially, such as abutted line segments in serial or parallel formations. For example, the motion of the second dispenser and/or the dispensed second bio-ink can directly disturb the first bio-ink dispensed by the first dispenser, or indirectly via disturbing the support material. Thus, a solution to this technical problem is to develop a bio-printer having a parallel dispense system having a common outlet with two dispense tips, wherein the two dispense tips are substantially in parallel.

Even when bio-printing on a flat surface, without support material, the ability to produce geometry with two separate bio-inks abutted may be compromised by the flow behavior of the respective bio-inks. The realized bioprinted structure may deviate substantially if the first dispensed bio-ink flows into the target area of the second dispensed bio-ink. This technical problem is solved by the present invention's parallel bio-printing system and corresponding methods because they enable deposition of two separate bio-inks from two separate dispense tips substantially in parallel. This facilitates the differential deposition and/or patterning of multiple, separate bioinks by addressing the aforementioned complications associated with the rheological properties of bio-inks. Specifically the invention allows the deposition of multiple, separate bio-inks to achieve a desired pattern before the first bio-ink's post-deposition flows compromise said pattern, and/or by limiting the motion within a support material to one individual dispenser capable of depositing two or more distinct bio-inks.

Another significant technical challenge is the fluid dynamics of the bio-inks. Fluidic resistance increases with fluidic path length. Dead volume should ideally be minimized due to the value of the biomaterial constituent components of the bio-inks. Dead volume can be minimized by minimizing the diameter of the fluidic channel. Fluidic resistance increases as the fluidic channel's diameter decreases. Bio-inks are often non-Newtonian in nature, meaning their viscosities are not constant, but rather vary with applied force. This variable viscosity adds complexity to the bio-printing process, making controlled dispense of the bio-inks a technical challenge. Thus, the inherently high fluidic resistance coupled with the non-Newtonian properties of the bio-inks present complications. Specifically, the time at which material starts and/or stops flowing out of the dispenser is not the same as the time at which force is applied to and/or removed from the dispenser, respectively. This directly inhibits the dispenser from achieving its purpose of facilitating high-resolution, differential patterning of multiple, separate bio-inks. For example, if a first bio-ink is still flowing out of the first dispense tip when the second bio-ink starts to flow out of the second dispense tip, then the realized structure will deviate from the desired structure.

The purpose of the parallel bio-printing systems and methods described herein is to facilitate the differential deposition and/or patterning of multiple, separate bio-inks by addressing the aforementioned technical challenges associated with the rheological properties of the bio-inks. Specifically the invention allows the simultaneous deposition of multiple, separate bio-inks to achieve a desired structure and/or pattern before the materials' post-deposition flows compromise said pattern, and by limiting the motion within a support material to one individual dispenser capable of depositing two or more distinct bio-inks. To address the technical challenges relating to fluid dynamics of bio-inks, as described above, the disclosed parallel bio-printing system enables the application of an opposite force, such as an aspiration step, to stop biomaterials, such as bio-inks, from flowing. In addition, the disclosed parallel bio-printing system enables the return of temporal control to the parallel bio-printing system and allows subsequent bio-inks to be deposited without be negatively affected by the first dispensed bio-ink.

SUMMARY OF THE INVENTION

The invention provides compositions comprising a hydrogel comprising a plurality of channels comprising cellular constructs comprising mesenchymal cells and epithelial cells. In one embodiment the hydrogel is collagen, denatured collagen, gelatin, hyaluronic acid or salt thereof, fibrin, alginate, agarose, chitosan, or combinations thereof. In certain embodiments, the hydrogel, cellular constructs and/or the channels further comprise at least one additional cell type. In other embodiments, the at least one additional cell type in the hydrogel, cellular constructs and/or channels are dermal fibroblasts, endothelial cells, pre-adipocytes, immune cells, melanocytes, or stem cells. In other embodiments, the hydrogel, cellular constructs and/or the channels comprise at least one hair follicle maturation factor. In other embodiments, the at least one hair follicle maturation factor is a fibroblast growth factor (FGF), a Wnt agonist, a bone morphogenetic protein (BMP), or a combination thereof. In other embodiments, the FGF is FGF7, FGF9, FG10 or a combination thereof. In other embodiments, the Wnt agonist is CHIR99021, LiCl, SB-216763, or CAS 853220-52-7. In other embodiments, the BMP is BMP2, BMP4 or BMP6. In other embodiments, the cellular constructs further comprise melanocytes. In other embodiments, the cellular constructs are substantially straight. In other embodiments, the cellular constructs are curved. In other embodiments, the surfaces of the cellular constructs are irregular. In other embodiments, the mesenchymal cells are segmented at one end of the cellular constructs and the epithelial cells are segmented at the other end of the cellular constructs. In other embodiments, the cellular constructs are 50 to 10,000 μm in length and 50 to 2000 μm in diameter. In other embodiments, the cellular constructs are 4 to 10 mm in length and 50 to 750 μm in diameter. In other embodiments, the ratio of mesenchymal cells to epithelial cells is 10:1 to 1:10. In other embodiments, the ratio of mesenchymal cells to epithelial cells is 1:2 to 1:1. In other embodiments, the mesenchymal cells are dermal papilla cells. In other embodiments, the cellular constructs further comprise cysts. In other embodiments, the cysts comprise dermal papilla cells. In other embodiments, the epithelial cells are dermal epithelial cells. In other embodiments, the dermal epithelial cells are keratinocytes. In other embodiments, the mesenchymal and epithelial cells are human cells.

The volume of the hydrogel may range from 300 μl up to 50 ml or more depending on the number of cellular constructs.

The invention further provides a kit comprising the composition of the invention and instructions for use of the kit. In one embodiment, the kit further comprises an instrument to implant the cellular constructs.

The invention further provides a method of making the composition of the invention, comprising deposition of the mesenchymal cells and epithelial cells into the hydrogel. In one embodiment, a mixture of the mesenchymal cells and epithelial cells are deposited into the hydrogel by insertion of a needle into the hydrogel and withdrawal of the needle concurrent with extrusion of the mesenchymal cells and epithelial cells from the tip of the needle, such as a dispense tip. The tip of a needle and a "dispense tip" are used interchangeably throughout this disclosure. In other embodiments, the mesenchymal cells and epithelial cells are deposited into the hydrogel by insertion of one or more needles into the hydrogel and withdrawal of the needle(s) concurrent with extrusion of the mesenchymal cells and epithelial cells from the tip of the needle. In other embodiments, the mesenchymal cells are segmented at the tip of the needle. In other embodiments, the mesenchymal cells are deposited from the tip of the needle and then the epithelial cells are deposited from the needle to provide a segmented cell construct with the mesenchymal cells at the bottom end of the channels and the epithelial cells at the top end of the channels. In other embodiments, the needle is first loaded with epithelial cells then the needle is loaded with mesenchymal cells at the tip of the needle prior to deposition of the cells. In other embodiments, the needle is a multiaxial needle having a core and at least one mantle layer providing concentric flow of at least two different inputs for at least two different types of cells, wherein the mesenchymal cells are extruded from the core and the epithelial cells are extruded from a mantle layer. In other embodiments, the mesenchymal cells are deposited from the core of the needle and then the epithelial cells are deposited from the mantle layer of the needle to provide a segmented cell construct with the mesenchymal cells at the bottom end of the channels and the epithelial cells at the top end of the channels. In other embodiments, the mesenchymal cells and epithelial cells are deposited as part of one or more compositions further comprising an extrusion compound. In other embodiments, the extrusion compound is an alginate, a hydrogel, a collagen, Novogel®, Matrigel®, extracellular matrix components, or a water soluble, cross-linkable, biodegradable polymer. In other embodiments, the method further comprises maturing the cellular constructs. In one embodiment, the cellular constructs are matured for 1 to 42 days. In other embodiments, the cellular constructs are matured for 7 to 21 days. In other embodiments, the method further comprises removing the cellular constructs from the hydrogel. In other embodiments, the deposition is controlled by an automated device comprising at least one needle and one or more reservoirs in fluid communication with the needle and a means for extruding the contents of the at least one needle, wherein the one or more reservoirs comprise mesenchymal cells, epithelial cells or mixtures thereof, and an actuation means that positions the needle relative to the surface of the hydrogel. In other embodiments, the automated device deposits a plurality of constructs in the hydrogel. In other embodiments, the automated device comprises a computer processor communicatively connected to the means for extruding the contents of the at least one needle. In other embodiments, the mesenchymal and epithelial cells are human cells. In other embodiments, the epithelial cells are not deposited as spheroids.

The invention further provides cellular constructs in the form of a column comprising mesenchymal cells and epithelial cells. In one embodiment, the cellular construct further comprises melanocytes. In other embodiments, the cellular construct is substantially straight. In other embodiments, the cellular construct is curved. In other embodiments, the surfaces of the cellular construct is irregular. In other embodiments, the mesenchymal cells are segmented at one end of the cellular construct and the epithelial cells are segmented at the other end of the cellular construct. In other embodiments, the cellular construct is 50 to 10,000 μm in length and 50 to 2000 μm in diameter. In other embodiments, the cellular construct is 4 to 10 mm in length and 50 to 750 μm in diameter. In other embodiments, the ratio of mesenchymal cells to epithelial cells is 10:1 to 1:10. In other embodiments, the ratio of mesenchymal cells to epithelial cells is 1:2 to 1:1. In other embodiments, the mesenchymal cells are dermal papilla cells. In other embodiments, the cellular construct further comprises cysts. In other embodiments, the cysts comprise dermal papilla cells. In other embodiments, the epithelial cells are dermal epithelial cells. In other embodiments, the dermal epithelial cells are keratinocytes. In other embodiments, the mesenchymal and epithelial cells are human cells.

The invention further provides a method of hair restoration in an individual, comprising implanting at least one cellular construct described herein into the skin of the individual. In one embodiment, the skin is the scalp. In other embodiments, the implantation is manual. In other embodiments, the implantation is automated.

The invention further provides a method of hair restoration in an individual, comprising implanting a composition comprising mesenchymal cells and epithelial cells into the skin of the individual. In one embodiment, the composition is implanted by insertion of a needle into the skin. In another embodiment, the needle is a co-axial device having two or more separate material pathways providing concentric flow around a common axis of at least two different inputs for at least two different types of cells, wherein the mesenchymal cells are extruded from the core and the epithelial cells are extruded from a mantle layer of the coaxial needle. In another embodiment, the skin is the scalp. In another embodiment, the implantation is manual. In another embodiment, the implantation is automated.

Also disclosed is a parallel bio-printing system comprising a first dispenser comprising a first bio-ink and a first outlet, the first bio-ink comprises a plurality of human cells; a second dispenser comprising a second bio-ink and a second outlet, the second bio-ink comprises a plurality of human cells; a common dispense module comprising a first module, a second module, and a common outlet; the first module is in fluidic communication with the first dispenser, the first module comprises a first inlet, a first body, and a first dispense tip; the second module is in fluidic communication with the second dispenser, the second module comprises a second inlet, a second body, and a second dispense tip; and the common outlet comprises the first dispense tip and the second dispense tip, the first dispense tip is substantially in parallel with the second dispense tip, the first dispense tip for depositing at least a portion of the first bio-ink, and the second dispense tip for depositing at least a portion of the second bio-ink.

Further disclosed is a method of making a cellular construct comprising the steps of descending a common outlet a first pre-determined distance into a semi-solid material, the common outlet comprises a first dispense tip and a second dispense tip, the first dispense tip is substantially in parallel with the second dispense tip, wherein as the common outlet descends into the semi-solid material, the common outlet displaces an area of the semi-solid material equivalent to an area of the common outlet descended into the semi-solid material; depositing, using the first dispense tip, a pre-determined amount of a first bio-ink into the semi-solid material, the first bio-ink comprises a plurality of human cells, wherein the depositing occurs while the common outlet ascends a first pre-determined distance; and depositing, using the second dispense tip, a pre-determined amount of a second bio-ink into the semi-solid material, the second bio-ink comprises a plurality of human cells, wherein the depositing occurs while the common outlet ascends a second pre-determined distance, wherein the dispensed pre-determined amount of the first bio-ink and the dispensed pre-determined amount of the second bio-ink form a cellular construct within the semi-solid material.

BRIEF DESCRIPTION OF THE DRAWINGS

FIG. 1A depicts a micrograph of a follicle organoid showing a layered structure after 24 hrs. FIG. 1B is two bar charts comparing expression of genes in 2D culture of human hair dermal papilla (HHDP) cells compared to expression of genes expressed in follicle organoids. The follicle organoids manifested repression of genes associated with 2D HHDP culture and induction of gene expression found in native hair follicles.

FIG. 3E is a micrograph of dermal papilla printed into bioprinted skin.

FIGS. 6A-6C are photographs depicting the effect of various types of hydrogel compositions (FIG. 6A, rat-tail collagen (6 mg/ml); FIG. 6B, gelatin (8%); FIG. 6C, laminin/fibronectin (15 µg/ml±12.5)) on cellular construct maturation and cohesion within the channels. These results indicate that the selection of hydrogel had a clear effect on the maturation and cohesiveness of the cellular constructs and that the addition of extracellular matrix (ECM) did not significantly improve deposition.

FIGS. 7A-7F depict tissue constructs made from mixed papilla cells and keratinocytes when deposited into rat-tail collagen (FIG. 7A, 7 days culture; FIG. 7B, 21 days culture), when deposited into 8% gelatin (FIG. 7C, 7 days culture; FIG. 7D, 21 days culture), and when deposited into laminin/fibronectin (FIG. 7E, 7 days culture; FIG. 7F, 21 days culture). These constructs lacked organization as seen in native hair follicles. These results also demonstrate a lack of organization of cellular constructs containing ECM.

In FIG. 8D, rat tail collagen was added to the cell paste but not to the supporting hydrogel. These tissue constructs developed cyst formation characteristic of hair follicles.

FIG. 19B depicts a magnified portion of the end of the needle showing a 30° bevel.

FIGS. 20A-20E depict the coaxial needle delivery technique. FIG. 20A depicts the coaxial needle, primed with mesenchymal cells (dermal papilla cells) in the core and epithelial cells (keratinocytes) in the mantle layer, positioned on top of a hydrogel. FIG. 20B depicts the injection of the needle into the hydrogel. FIG. 20C depicts injection of the mesenchymal cells into the hydrogel. FIG. 20D depicts injection of the epithelial cells as the needle is withdrawn. FIG. 20E depicts the withdrawn needle above the hydrogel containing a channel with mesenchymal cells segmented at the bottom of the channel and epithelial cells segmented at the top of the channel.

FIGS. 21A-21D depict an alternative method of providing segmented channels where a needle is first primed with mesenchymal cells and placed over a vessel containing epithelial cells (FIG. 21A), the needle is inserted into the epithelial cells and the epithelial cells are aspirated into the needle (FIG. 21B), the needle is then inserted into a hydrogel (FIG. 21C), and the needle is then withdrawn from the hydrogel concurrent with the injection of the mesenchymal cells and epithelial cells (FIG. 21D) to give a channel with mesenchymal cells segmented at the bottom of the channel and epithelial cells segmented at the top of the channel.

DETAILED DESCRIPTION OF THE INVENTION

Definitions

Figure 1A:
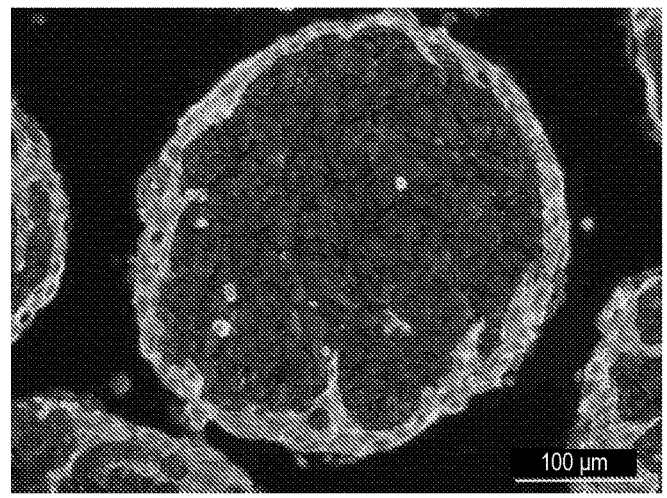
FIGS. 1A-1B depict characterization of follicle organoids.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

As used herein, "tissue" means an aggregate of cells. In some embodiments, the cells in the tissue are cohered or fused.

As used herein, "bioprinting," "bio-printing," "bio-printed," or "bio-printed" means utilizing three-dimensional, precise deposition of cells (e.g., cell solutions, cell-containing gels, cell suspensions, cell concentrations, multicellular aggregates, multicellular bodies, etc.) via methodology that is compatible with an automated or semi-automated, computer-aided, three-dimensional prototyping device (e.g., a bioprinter). Suitable bioprinters include the Novogen Bioprinter® from Organovo, Inc. (San Diego, CA) and those described in U.S. Pat. No. 9,149,952 and U.S. Publ Appl. Nos. 2015/0093932, 2015/0004273, and 2015/0037445.

As used herein, mesenchymal cells are multipotent stromal cells that can differentiate into papilla cells as well as the papilla cells themselves. Mesenchymal cells are present in extracellular matrix. Mesenchymal cells and papilla cells may be obtained commercially from PromoCell GmbH and ScienCell Research Laboratories. The mesenchymal cells may be cultured in commercially available growth media such as available from Sigma-Aldrich Co., LLC.

As used herein, epithelial cells are cells that from the epithelium. An example of epithelial cells are keratinocytes which form about 90% of the outermost layer of the skin. Epithelial cells and keratinocytes may be obtained commercially from PromoCell GmbH, and Lonza. The epithelial cells may be cultured in commercially available growth media such as available from Sigma-Aldrich Co., LLC.

As used herein, melanocytes are melanin-producing cells that may be found in the bottom layer of the epidermis and in hair follicles. Melanocytes may be isolated from the epidermis of juvenile foreskin or adult skin from different locations. In one embodiment, melanocytes are selected that produce melanin of particular intensity/colors to match the natural color of the recipient of hair restoration. In one embodiment, the melanocytes are lightly-pigmented. In another embodiment, the melanocytes are darkly-pigmented. Melanocytes may be obtained commercially from PromoCell GmbH, the American Type Culture Collection ATCC, and Genlantis. The melanocytes may be cultured in commercially available growth media such as available from ATCC, PromoCell GmbH, Lonza, Genlantis and Provitro.

As used herein an "individual" is an organism of any mammalian species including but not limited to humans, primates, apes, monkey, dogs, cats, mice, rats, rabbits, pigs, horses and others. A subject can be any mammalian species alive or dead.

As used herein, a "hair follicle maturation factor" is any factor that promotes the maturation of mesenchymal and epidermal cells to produce cysts that are capable of growing hair. Examples of hair follicle maturation factors include fibroblast growth factors (FGFs) and Wnt agonists, BMPs, BMP inhibitors, TNF agonists. Particular FGFs include FGF5, FGF7, FGF9, and FGF10. Particular BMPs include BMP2, BMP4 and BMP6. Wnt agonists are molecules that inhibit GSK3 (e.g. GSK3-β) in the context of the canonical Wnt signaling pathway. Non-limiting examples of Wnt agonists include CHIR99021, LiCl, SB-216763, and CAS 853220-52-7. Other Wnt agonists are commercially available from sources such as Santa Cruz Biotechnology and R & D Systems.

As used herein, "about" or "approximately" means ±10% of the recited value. For example, about 10 includes 9-11. Alternatively, approximately 10 includes 9-11.

In one embodiment, the cellular constructs are segmented. By "segmented" is intended that the constructs contain one or more regions with differential concentrations of mesenchymal cells and epithelial cells. In one embodiment, a segmented construct comprises one region containing just mesenchymal cells and another region with just epithelial cells. In this embodiment, it is understood that other optional cell types may be present in the regions. In another embodiment, a segmented construct comprises one region wherein a majority of cells are mesenchymal cells and another region where a majority of cells are epithelial cells. Again, in this embodiment, it is understood that other optional cell types may be present in the regions.

Hydrogels include those derived from collagen, hyaluronate, hyaluronan, fibrin, alginate, agarose, chitosan, and combinations thereof. In other embodiments, suitable hydrogels are synthetic polymers. In further embodiments, suitable hydrogels include those derived from poly(acrylic acid) and derivatives thereof, poly(ethylene oxide) and copolymers thereof, poly(vinyl alcohol), polyphosphazene, and combinations thereof. In various specific embodiments, the confinement material is selected from: hydrogel, Novo-Gel™, agarose, alginate, gelatin, Matrigel®, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly(lactic acid), silicon, silk, or combinations thereof. In some embodiments, the hydrogel is cross-linked. A cross-linked hydrogel provides a rigidity that permits repeated insertion of needles, such as dispense tips, into the same channel without disruption of the channel. Crosslinkable hydrogel-forming materials include polysaccharides such as alginate and salts thereof, peptides, polyphosphazenes, and polyacrylates, which are cross-linked ionically, and block polymers such as polyethylene oxide-polypropylene glycol block copolymers which are cross-linked by temperature or pH, respectively. In some embodiments, the hydrogel is biodegradable.

In another embodiment, the hydrogel, cellular constructs and/or channels further comprise a growth factor or hormone. In one embodiment, hydrogel, cellular constructs and/or channels comprise a melanocyte-stimulating hormone (MSH) such as α-MSH, β-MSH, or γ-MSH.

Hydrogel Compositions

Provided is a composition comprising a hydrogel comprising a plurality of channels comprising cellular constructs comprising mesenchymal cells and epithelial cells. In some embodiments, the hydrogel, cellular constructs and/or the channels further comprise at least one additional cell type such as dermal fibroblasts, endothelial cells, pre-adipocytes, immune cells, melanocytes, or stem cells. Examples of useful stem cells include any that are naturally part of hair follicles including stem cells identified by their distinct gene/protein-expression or promoter activity such as Lgr5, CD34, LRC, Lgr6, Lrig1/MTS24, Blimp1 and K15*. See Jaks et al., Exp. Cell Res. 316:1422-1428 (2010). In one embodiment, the hydrogel, cellular constructs and/or the channels comprise at least one hair follicle maturation factor. The at least one hair follicle maturation factor includes, but is not limited to a fibroblast growth factor (FGF), a Wnt agonist, a BMP, or a combination thereof. The FGF includes, but is not limited to FGF7, FGF9, FG10 or a combination thereof. The Wnt agonist includes, but is not limited to, CHIR99021, LiCl, SB-216763, and CAS 853220-52-7. The BMPs include, but is not limited to BMP2, BMP4, and BMP6.

In one embodiment, the cellular constructs further comprise melanocytes.

The cellular constructs are elongated and may be substantially straight or curved.

In one embodiment, the surfaces of the cellular constructs are irregular.

In one embodiment, the mesenchymal cells are segmented at one end of the cellular constructs and the epithelial cells are segmented at the other end of the cellular constructs. In another embodiment, the cellular constructs are 50 to 10,000 µm in length and 50 to 2000 µm in diameter. In another embodiment, the cellular constructs are 4 to 10 mm in length and 50 to 750 µm in diameter.

In one embodiment, the ratio of mesenchymal cells to epithelial cells is 10:1 to 1:10. In another embodiment, the ratio of mesenchymal cells to epithelial cells is 1:2 to 1:1.

In one embodiment, the mesenchymal cells are dermal papilla cells.

In one embodiment, the cellular constructs comprise cysts that give rise to hair. In another embodiment, the cysts comprise dermal papilla cells.

In one embodiment, the epithelial cells are dermal epithelial cells. In another embodiment, the dermal epithelial cells are keratinocytes.

In one embodiment, the mesenchymal and epithelial cells are human cells.

In one embodiment, the hydrogel comprises collagen, hyaluronic acid or salt thereof, fibrin, alginate, agarose, chitosan, or combinations thereof. In another embodiment, the hydrogel comprises alginate. In another embodiment, the hydrogel is cross-linked. It has been discovered that use of an alginate hydrogel gave very smooth deposition compared to other hydrogels. Although some channels in alginate had a cap of cells, the caps were much less frequent than with other hydrogels.

Kits

Also provided is a kit comprising the hydrogel composition with the cellular constructs and instructions for maintenance and use of the kit. For example, the instructions may instruct the user to keep the hydrogel composition refrigerated, e.g., at 4 to 40° C. In another embodiment, the instructions may instruct the user to remove the cellular constructs from the hydrogel composition and implant them under the skin of an individual. In one embodiment, the skin is the scalp of the individual.

In one embodiment, the kit may further comprise an instrument to remove and implant the cellular constructs. Any instrument useful for the implantation of hair follicles may be provided. In one embodiment, the instrument is forceps. In another embodiment, the instrument is a tube that is inserted into the hydrogel and slides over the cellular construct. The tube may be made of any biocompatible rigid substance including glass, stainless steel and plastic. A slight vacuum may be applied to the tube to facilitate the insertion of the cellular construct into the tube. The tube is then withdrawn and relocated to a recipient area and inserted under the skin. In one embodiment, the tube is beveled at the end to facilitate the insertion into the hydrogel. In another embodiment, the bevel is 10 to 45 degrees. In another embodiment, the bevel is about 30 degrees. In another embodiment, the beveled end of the tube is sharp so as to allow the insertion of the tube containing the construct into the skin. In another embodiment, the discharge of the cellular construct is facilitated by application of a positive pressure to the tube. In another embodiment, the cellular construct is rinsed prior to implantation.

In one embodiment, the kit may comprise a robotic device that removes the cellular constructs from the hydrogel and implants them into the skin of an individual. The robotic device may comprise computer-aided device that positions the tube, removes the cellular construct from the hydrogel, and inserts the cellular constructs into the skin according to a computer script. In further embodiments, the computer script is, for example, one or more computer programs, computer applications, or computer modules. The kit may comprise one or more tubes for removal and delivery of the cellular constructs.

In another embodiment, the kit may further comprise adipose-derived stromal and/or stem cells that may be combined with the cellular constructs prior to implantation. Methods for isolating and implanting the adipose-derived stromal and stem cells are described in U.S. Publ. Appl. No. 2007/0258956. The kit may also include instructions to implant the adipose-derived and/or stem cells together with the cellular construct as unitary or separate compositions.

In another embodiment, the kit may further comprise at least one hair follicle maturation factor. The at least one hair follicle maturation factor include, but are not limited to a fibroblast growth factor (FGF), a Wnt agonist, or a combination thereof. The FGF includes, but is not limited to FGF7, FGF9, FG10 or a combination thereof. The Wnt agonist includes, but is not limited to, CHIR99021, LiCl, SB-216763, and CAS 853220-52-7. The kit may also include instructions to implant the at least one hair follicle maturation factor together with the cellular construct as unitary or separate compositions.

Methods of Making the Hydrogel Compositions

Also provided is a method of making the composition comprising deposition of the mesenchymal cells and epithelial cells into the hydrogel. In one embodiment, a mixture of the mesenchymal cells and epithelial cells are deposited into the hydrogel by insertion of one or more needles, into the hydrogel and withdrawal of the needle(s) concurrent with extrusion of the mesenchymal cells and epithelial cells from the tip of the needle, such as a dispense tip. When more than one needle is employed, the needles are inserted sequentially, e.g., the first needle containing mesenchymal cells is inserted into the hydrogel and the mesenchymal cells are deposited and then the second needle is inserted into the channel made by the first needle and the epithelial cells are deposited. In one embodiment, the cells are deposited as part of a composition comprising one or more extrusion compounds. In another embodiment, the cells are deposited without an extrusion compound. In another embodiment, the mesenchymal cells and epithelial cells are deposited into the hydrogel by insertion of a needle into the hydrogel and withdrawal of the needle concurrent with extrusion of the mesenchymal cells and epithelial cells from the tip of the needle, such as a dispense tip. In one embodiment, the mesenchymal cells are segmented at the tip of the needle, such as a dispense tip. In another embodiment, the mesenchymal cells are deposited from the tip of the needle, such as a dispense tip, and then the epithelial cells are deposited from the needle to provide a segmented cell construct with the mesenchymal cells at the bottom end of the channels and the epithelial cells at the top end of the channels. In another embodiment, the needle is first loaded with epithelial cells then the needle is loaded with mesenchymal cells at the tip of the needle, such as a dispense tip, prior to deposition of the cells.

Figure 19A:
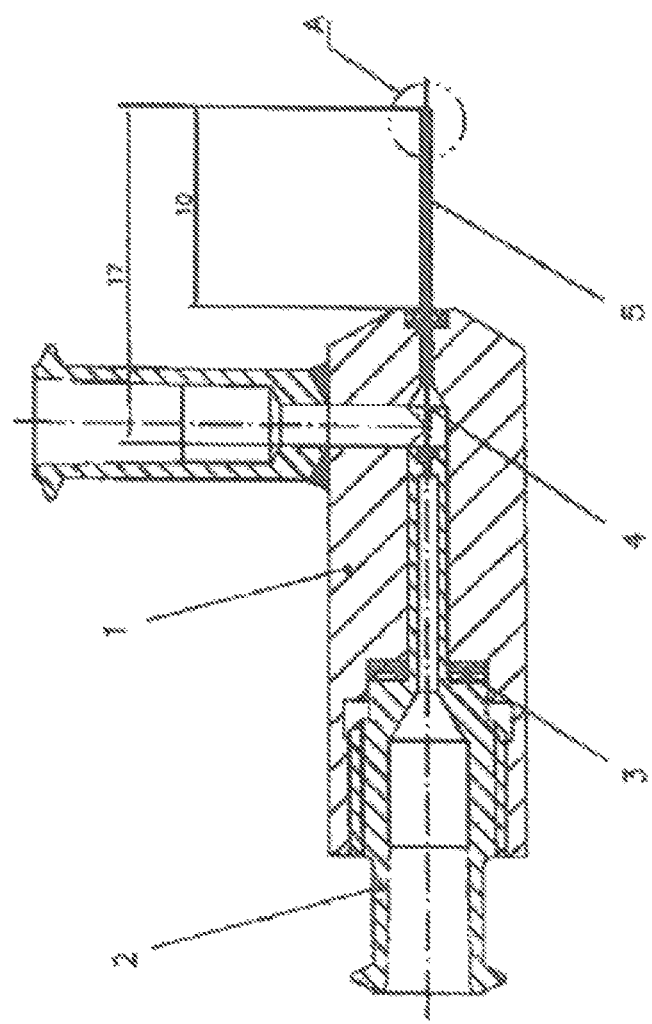
FIGS. 19A-19B depict a coaxial needle providing concentric flow of two different inputs for two different types of cells, e.g., wherein the mesenchymal cells are extruded from the core and the epithelial cells are extruded from a mantle layer.
Figure 19B:
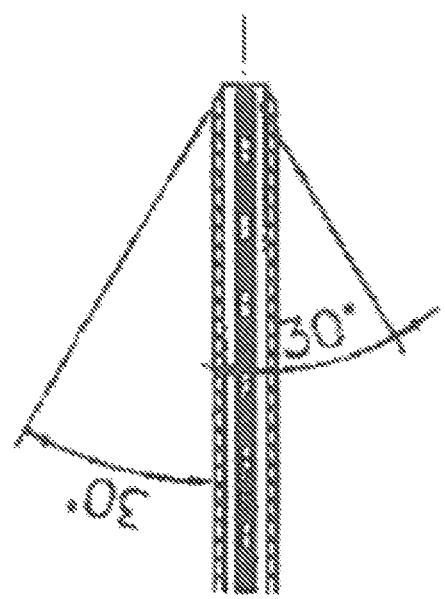

In one embodiment, the needle is a co-axial device having two or more separate material pathways providing concentric flow around a common axis of at least two different inputs for at least two different types of cells, wherein the mesenchymal cells are extruded from the core and the epithelial cells are extruded from a mantle layer of the coaxial needle FIGS. 19A-19B depict a coaxial needle (5) fed by two different cellular inputs. In one embodiment, the mesenchymal cells are deposited from the core of the needle and then the epithelial cells are deposited from the mantle layer of the needle to provide a segmented cell construct with the mesenchymal cells at the bottom end of the channels and the epithelial cells at the top end of the channels.

In one embodiment, the mesenchymal cells and epithelial cells are deposited as part of one or more compositions further comprising an extrusion compound. In another embodiment, the extrusion compound comprises alginate, a hydrogel, a collagen, Novogel®, Matrigel®, extracellular matrix components, or a water soluble, cross-linkable, biodegradable polymer.

In one embodiment, the cellular constructs are matured after being deposited in the hydrogel. In another embodiment, the cellular constructs are matured for 1 to 42 days. In another embodiment the cellular constructs are matured for 7 to 21 days.

In one embodiment, the method further comprises removing the cellular constructs from the hydrogel. The cellular constructs may be removed manually or by use of an automated device. In another embodiment, the automated device comprises at least one needle and one or more reservoirs in fluid communication with the needle and a means for extruding the contents of the at least one needle, wherein the one or more reservoirs comprise mesenchymal cells, epithelial cells or mixtures thereof, and an actuation means that positions the needle relative to the surface of the hydrogel. Means for extruding the contents of the needle include application of pressure, application of compressed gas, use of a piston, hydraulics, or a combination thereof. In another embodiment, the automated device comprises a computer processor communicatively connected to the means for extruding the contents of the at least one needle. In this embodiment, the computer processor controls the timing and amount of cellular deposition into the hydrogel.

In one embodiment, the needle is beveled. In another embodiment, the needle is beveled 10 to 45 degrees. In another embodiment, the needle is beveled about 30 degrees. In another embodiment, the outer diameter of the needle is about 250 μm to about 1250 μm. In another embodiment, the outer diameter of the needle is 350 to 1000 μm. In another embodiment, the outer diameter of the needle is about 500 μm. In another embodiment, the inner diameter of the needle is between about 150 to about 1000 μm.

In one embodiment, the automated device deposits a plurality of constructs in the hydrogel. In another embodiment, the automated device deposits 1,000 to 10,000 cellular constructs in the hydrogel.

The mesenchymal and epithelial cells may be derived from any mammal. In one embodiment, the mesenchymal and epithelial cells are human cells.

In one embodiment, the epithelial cells are not deposited as spheroids.

Cellular Constructs

Provided are cellular constructs in the form of a column comprising mesenchymal cells and epithelial cells. In one embodiment the cellular constructs comprise additional cells. In one embodiment, the cellular constructs further comprise melanocytes.

In one embodiment, the cellular construct is substantially straight, i.e., it does not deviate in thickness by more than about 20% along its length. In another embodiment, the cellular construct is curved. In another embodiment, the surfaces of the cellular construct are irregular, e.g., they comprise bumps, ridges, valleys and/or crevices.

In one embodiment, the mesenchymal cells are segmented at one end of the cellular construct and the epithelial cells are segmented at the other end of the cellular construct.

In one embodiment, the cellular construct is 50 to 10,000 μm in length and 50 to 2000 μm in diameter. In another embodiment, the cellular construct is 4 to 10 mm in length and 50 to 750 μm in diameter. In another embodiment, the ratio of mesenchymal cells to epithelial cells is 10:1 to 1:10. In another embodiment, the ratio of mesenchymal cells to epithelial cells is 1:2 to 1:1.

In one embodiment, the mesenchymal cells are dermal papilla cells.

In one embodiment, the cellular construct further comprises cysts. In another embodiment, the cysts are capable of growing hair. In another embodiment, the cysts comprise dermal papilla cells.

In one embodiment, the epithelial cells are dermal epithelial cells. In another embodiment, the dermal epithelial cells are keratinocytes.

Methods of Hair Restoration

Provided is a method of hair restoration in an individual, comprising implanting at least one cellular construct as described herein into the skin of the individual. In one embodiment, the skin is the scalp.

In one embodiment, the implantation is manual. In this embodiment, the cellular construct is withdrawn from the hydrogel, optionally rinsed to remove hydrogel, and inserted into an opening made into the skin, e.g., with forceps. The opening may be made with a scalpel or punch.

In another embodiment, the implantation is automated. In this embodiment, the cellular construct is withdrawn from the hydrogel by a robotic device that removes the cellular constructs from the hydrogel and implants them into the skin of an individual. The robotic device may comprise a computer-aided device that positions a tube, removes the cellular construct from the hydrogel by insertion into the tube, and inserts the cellular constructs into the skin according to a computer script. In further embodiments, the computer script is, for example, one or more computer programs, computer applications, or computer modules. The robotic device may also create openings into the skin with a scalpel or punch according to a computer script to deliver the cellular constructs to the skin in a desired pattern, e.g., to restore the natural hair line of a scalp.

Parallel Bio-Printing System for Bio-Printing Cellular Construct

Also disclosed is a parallel bio-printing system comprising a first dispenser comprising a first bio-ink and a first outlet, the first bio-ink comprises a plurality of human cells; a second dispenser comprising a second bio-ink and a second outlet, the second bio-ink comprises a plurality of human cells; a common dispense module comprising a first module, a second module, and a common outlet; the first module is in fluidic communication with the first dispenser, the first module comprises a first inlet, a first body, and a first dispense tip; the second module is in fluidic communication with the second dispenser, the second module comprises a second inlet, a second body, and a second dispense tip; and the common outlet comprises the first dispense tip and the second dispense tip, the first dispense tip is substantially in parallel with the second dispense tip, the first dispense tip for depositing at least a portion of the first bio-ink, and the second dispense tip for depositing at least a portion of the second bio-ink.

In some embodiments of the dispensing system, the first module and the second module form a symmetric configuration. In some embodiments, the dispensing system further comprises a receiving surface. In some embodiments, the receiving surface comprises a semi-solid material. In some embodiments, the semi-solid material comprises a hydrogel derived from collagen, hyaluronate, hyaluronan, fibrin, alginate, agarose, chitosan, and combinations thereof. In some embodiments, the semi-solid material comprises a cellular construct, including but not limited to, a human tissue construct. In some embodiments, the second bio-ink has a different composition of human cells from the first bio-ink. In some embodiments, the first bio-ink comprises at least one cell type that is not present in the second bio-ink.

In some embodiments, the first bio-ink comprises mesenchymal cells. In some embodiments, the mesenchymal cells are dermal papilla cells. In some embodiments, the second bio-ink comprises epithelial cells. In some embodiments, the epithelial cells are dermal epithelial cells. In some embodiments, the dermal epithelial cells are keratinocytes. In some embodiments, the second bio-ink further comprises keratinocytes and smooth muscle cells. In addition to different cell types, the first and second bio-inks can comprise different concentrations of the same cell type or different cell types.

In some embodiments, the first bio-ink further comprises a gel. In some embodiments, the gel is a hydrogel.

In some embodiments, the first module and the second module are capable of aspirating the first bio-ink and the second bio-ink, respectively. In some embodiments, the first dispenser and the second dispenser are capable of aspirating the first bio-ink and the second bio-ink, respectively.

In some embodiments, the first dispenser is substantially in parallel with the second dispenser.

In some embodiments, the first dispenser is affixed to the first module, and the second dispenser is affixed to the second module. In some embodiments, the first dispenser is a separable unit from the first module, and the second dispenser is a separable unit from the second module.

In some embodiments, the first dispenser and the second dispenser are extrusion-based dispensers including, but not limited to, automated syringe dispensers or pneumatic-actuated dispensers.

In some embodiments, the common outlet comprises a diameter of approximately 0.4 mm to 2.0 mm, including but not limited to approximately 0.4 mm, 0.5 mm, 0.6 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, and 2.0 mm in diameter.

Parallel Bio-Printing Method for Making a Cellular Construct

Further disclosed is a method of making a cellular construct comprising the steps of descending a common outlet a first pre-determined distance into a semi-solid material, the common outlet comprises a first dispense tip and a second dispense tip, the first dispense tip is substantially in parallel with the second dispense tip, wherein as the common outlet descends into the semi-solid material, the common outlet displaces an area of the semi-solid material equivalent to an area of the common outlet descended into the semi-solid material; depositing, using the first dispense tip, a pre-determined amount of a first bio-ink into the semi-solid material, the first bio-ink comprises a plurality of human cells, wherein the depositing occurs while the common outlet ascends a first pre-determined distance; and depositing, using the second dispense tip, a pre-determined amount of a second bio-ink into the semi-solid material, the second bio-ink comprises a plurality of human cells, wherein the depositing occurs while the common outlet ascends a second pre-determined distance, wherein the dispensed pre-determined amount of the first bio-ink and the dispensed pre-determined amount of the second bio-ink form a cellular construct within the semi-solid material. In some embodiments, the foregoing method is performed in approximately 75 to 120 seconds. In some embodiments, the method further comprises repeating one or more cycles of the foregoing method. In some embodiments, the cellular construct is a human tissue construct.

In some embodiments, the method further comprises the steps of aspirating, prior to the depositing the pre-determined amount of the second bio-ink into the semi-solid material, a pre-determined amount of the first bio-ink using the first dispense tip. In some embodiments, the method further comprises aspirating, after the depositing of the pre-determined amount of the second bio-ink into the semi-sold material, a pre-determined amount of the second bio-ink using the second dispense tip. In some embodiments, the method further comprises pausing, prior to the depositing the pre-determined amount of the second bio-ink into the semi-solid material, any action by the common outlet for a pre-determined amount of time. In some embodiments, the method further comprises pausing, after the depositing of the pre-determined amount of the second bio-ink into the semi-sold material, any action by the common outlet for a pre-determined amount of time.

In some embodiments, the method further comprises ascending, prior to the dispense of the pre-determined amount of the first bio-ink, the common outlet a pre-determined length within the semi-solid material. In some embodiments, the method further comprises moving, prior to the dispense of the pre-determined amount of the second bio-ink, the common outlet a pre-determined length horizontally. In some embodiments, the method further comprises moving, after the dispense of the pre-determined amount of the second bio-ink, the common outlet a pre-determined length horizontally; and moving the common outlet vertically out of the semi-solid material. In some embodiments, the method further comprises repeating one or more cycles of the foregoing method, which further comprises aspirating, prior to the dispense of the pre-determined amount of the first bio-ink for a second cycle, the second bio-ink from the second dispense tip back to the second module.

In some embodiments, the semi-solid material is a hydrogel. In some embodiments, the semi-solid material comprises a hydrogel derived from collagen, hyaluronate, hyaluronan, fibrin, alginate, agarose, chitosan, and combinations thereof. In some embodiments, the semi-solid material comprises a cellular construct, including but not limited to, a human tissue construct.

In some embodiments, the first bio-ink has a different composition of human cells from the second bio-ink. In some embodiments, the first bio-ink comprises at least one cell type that is not present in the second bio-ink.

In some embodiments, the first bio-ink comprises mesenchymal cells. In some embodiments, the mesenchymal cells are dermal papilla cells. In some embodiments, the second bio-ink comprises epithelial cells. In some embodiments, the epithelial cells are dermal epithelial cells. In some embodiments, the dermal epithelial cells are keratinocytes. In some embodiments, the second bio-ink further comprises keratinocytes and smooth muscle cells. In addition to different cell types, the first and second bio-inks can comprise different concentrations of the same cell type or different cell types.

In some embodiments, the first dispenser and the second dispenser are extrusion-based dispensers including, but not limited to, automated syringe dispensers or pneumatic-actuated dispensers.

The pre-determined amount of the first bio-ink and the second bio-ink can be any desired volume, as different cellular constructs have different structures and volumes. In some embodiments, the pre-determined amount of the first bio-ink is approximately 0.5 to 1.0 microliters (µL), including but not limited to approximately 0.5 µL, 0.6 µL, 0.7 µL, 0.8 µL, 0.9 µL, and 1.0 µL. In some embodiments, the pre-determined amount of the second bio-ink is approximately 2.0 to 3.0 microliters (µL), including but not limited to approximately 2.0 µL, 2.1 µL, 2.2 µL, 2.3 µL, 2.4 µL, 2.5 µL, 2.6 µL, 2.7 µL, 2.8 µL, 2.9 µL, and 3.0 µL.

In some embodiments, the dispensed first bio-ink forms a substantially straight having a length of approximately 0.5 to 1.0 millimeters (mm), including but not limited to approximately 0.5 mm, 0.6 mm, 0.7 mm, 0.8 mm, 0.9 mm, and 1.0 mm and a diameter of approximately 0.5 to 1.5 mm, including but not limited to approximately 0.5 mm, 0.6 mm, 0.7 mm, 0.8 mm, 0.9 mm, and 1.0 mm. In some embodiments, the dispensed second bio-ink forms a substantially straight having a length of approximately 2.5 to 3.5 millimeters including but not limited to approximately 2.5 mm, 2.6 mm. 2.7 mm, 2.8 mm, 2.9 mm, 3.0 mm, 3.1 mm, 3.2 mm, 3.3 mm, 3.4 mm, and 3.5 mm and a diameter of approximately 0.5 to 1.5 mm, including but not limited to approximately 0.5 mm, 0.6 mm, 0.7 mm, 0.8 mm, 0.9 mm, 1.0 mm, 1.1 mm, 1.2 mm, 1.3 mm, 1.4 mm, and 1.5 mm. In other embodiments, the first bio-ink and the second bio-ink can have different lengths and different structures (i.e. not substantially straight), as different cellular constructs have different structures and volumes.

In some embodiments, the cellular construct initially formed has a substantially straight having a length of approximately 3.0 to 4.5 millimeters, including but not limited to approximately 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, and 4.5 mm, a diameter of approximately 0.5 to 1.5 mm, including but not limited to approximately 0.5 mm, 0.6 mm, 0.7 mm, 0.8 mm, 0.9 mm, 1.0 mm, 1.1 mm, 1.2 mm, 1.3 mm, 1.4 mm, and 1.5 mmm. In other embodiments, the formed cellular construct can have different lengths and different structures (i.e. not substantially straight), as different cellular constructs have different structures, lengths, and volumes.

In some embodiments, wherein at the first ascending step, the pre-determined distance ascended is approximately 1.0 to 2.0 millimeters (mm), including but not limited to approximately 1.0 mm, 1.1 mm, 1.2 mm, 1.3 mm, 1.4 mm, 1.5 mm, 1.6 mm, 1.7 mm, 1.8 mm, 1.9 mm, and 2.0 mm. The pre-determined amount of the first bio-ink and the second bio-ink can be any desired volume, as different cellular constructs have different structures and volumes In some embodiments, the pre-determined amount of the first bio-ink aspirated is approximately 1.0 to 1.5 microliters (µL), including but not limited to approximately 1.0 µL, 1.1 µL, 1.2 µL, 1.3 µL, 1.4 µL, and 1.5 µL. In some embodiments, the pre-determined amount of the second bio-ink aspirated is approximately 2.0 to 3.0 microliters (µ), including but not limited to approximately 2.0 µL, 2.1 µL, 2.3 µL, 2.4 µL, 2.5 µL, 2.6 µL, 2.7 µL, 2.8 µL, 2.9 µL, and 3.0 µL.

In some embodiments, when repeating one or more cycles of this foregoing method, the pre-determined amount of the second bio-ink aspirated, before the common outlet descends into the semi-solid material, is approximately 1.0 to 1.5 microliters (µ), including but not limited to approximately 1.0 µL, 1.1 µL, 1.2 µL, 1.3 µL, 1.4 µL, and 1.5 µL. In some embodiments, the pre-determined length horizontally is approximately 0.1 to 0.5 millimeters (mm), including but not limited to approximately 0.1 mm, 0.2 mm, 0.3 mm, 0.4 mm, and 0.5 mm. In some embodiments, wherein at the first ascending step, the first pre-determined length is equal to approximately a maximum depth of the semi-solid material, which can approximately 1.0 to 2.0 millimeters (mm), including but not limited to approximately 1.0 mm, 1.2 mm, 1.3 mm, 1.4 mm, 1.5 mm, 1.6 mm, 1.7 mm, 1.8 mm, 1.9 mm, and 2.0 mm. In some embodiments, the pre-determined amount of time paused is approximately 5 to 15 seconds, including but not limited to approximately 1, 2, 3, 4, 5, 6, 7, 8, 9, 10, 11, 12, 13, 14, and 15 seconds.

Parallel Bio-Printing Method for Bio-Printing Cellular Construct with Gradients

In some embodiments, the method further comprises creating a gradient by depositing one or more bio-inks as the common outlet, including the dispense tips, deposits while the common outlet ascends. In some embodiments, the gradient is based on different cell concentrations of one or more cell types in the one or more bio-inks. For example, the gradient would comprise an increasing or decreasing cell concentration of one or more cell types vertically, such as lower cell concentrations to higher cell concentrations from lowest vertical point to highest vertical point, or alternatively, higher cell concentrations to lower cell concentrations from lowest vertical point to highest vertical point. As previously described, the gradient can be created in a supporting material, such as a semi-solid material, including a cellular construct including a human tissue construct. The different cell concentrations of one or more cell types can be achieved by preparing bio-inks having different cell concentrations. For example, the first bio-ink can comprise one cell concentrations of one or more cell types, and the second bio-ink can comprise a different cell concentration of one or more cell types. For example, the first bio-ink can comprise one cell concentrations of mesenchymal cells, and the second bio-ink can comprise a different cell concentration of mesenchymal cells. Alternatively, the first bio-ink can comprise one cell concentrations of a combined mixture of mesenchymal cells and epithelial cells, and the second bio-ink can comprise a different cell concentration of a combined mixture of mesenchymal cells and epithelial cells. Optionally, two or more cell types can be utilized.

In some embodiments, the gradient is based on different cell types in the one or more bio-inks, and based on different cell concentrations of one or more cell types in the one or more bio-inks. For example, the first bio-ink can comprise one cell concentrations of mesenchymal cells, and the second bio-ink can comprise another cell concentration of epithelial cells. Alternatively, the first bio-ink can comprise one cell concentrations of a combined mixture of mesenchymal cells and epithelial cells, and the second bio-ink can comprise a different cell concentration of a combined mixture of mesenchymal cells and epithelial cells. Optionally, two or more cell types can be utilized.

In some embodiments, the gradient is based on different cell types in the one or more bio-inks. For example, the first bio-ink can comprise mesenchymal cells (i.e. dermal papilla cells) and the second bio-ink can comprise epithelial cells (i.e. dermal epithelial cells, keratinocytes).

EXAMPLES

Example 1

Deposition of Mixed Aggregates of Cells

Figure 1B:
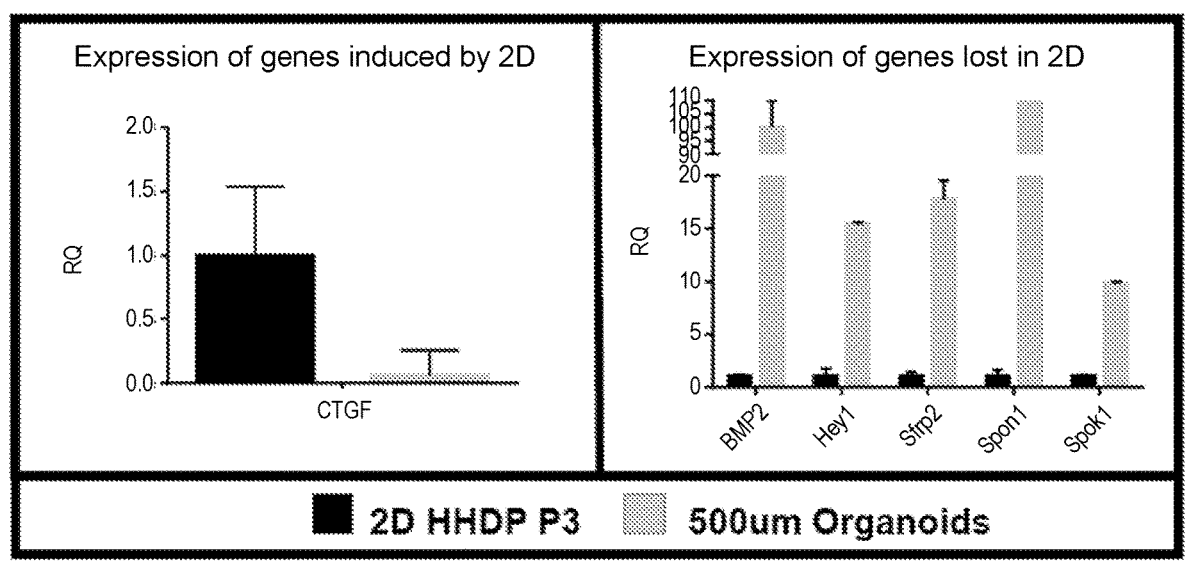
Figure 2E:
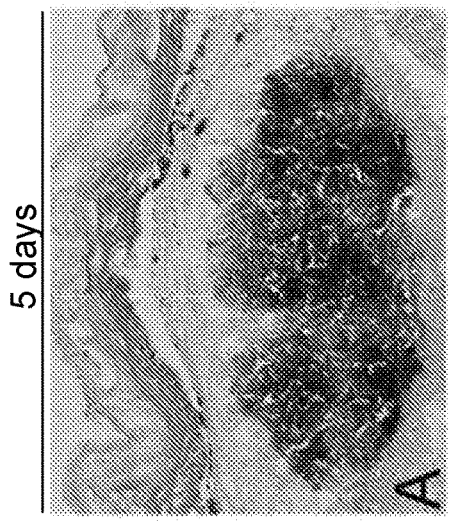
FIGS. 2A-2F depict micrographs of cultured cells showing cysts at 14 days (FIGS. 2A-2D) in comparison to HHDP cells cultured for 5 days (FIG. 2E) and 6 weeks (FIG. 2F) as reported by Higgins et al., *PNAS* 110:19679-88 (2013). The organoids were made from 80:20 HHDP:HEK.
Figure 2F:
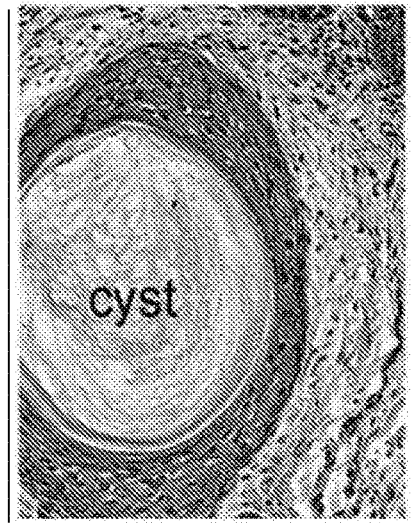
Figure 2B:
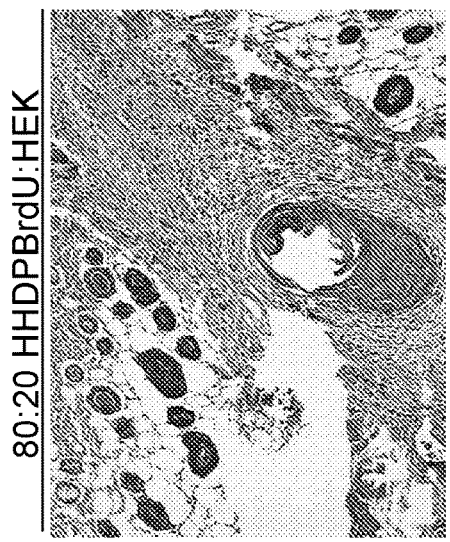
Figure 2D:
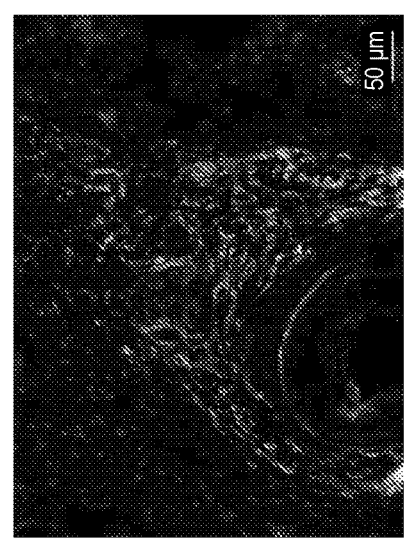
Figure 2A:
Figure 2C:
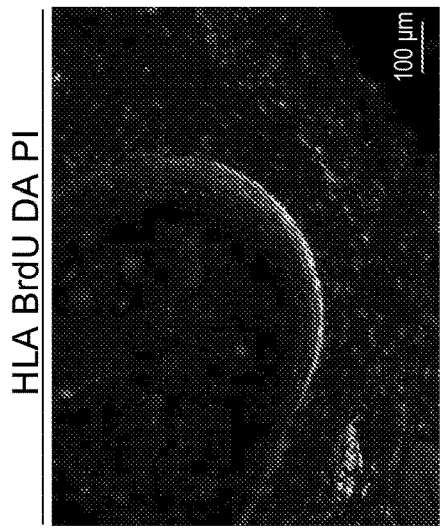

The starting point involved deposition of mixed aggregates of dermal papilla cells and keratinocytes. Aggregated spheroid structures (See, FIG. 1A) are comparable to those described in the literature (Higgins (2013) and from hair-like structures after in vivo implantation. In our hands, aggregates never underwent significant remodeling in vitro. And, gene expression patterns were lost in 2D culture (FIG. 1B). A lack of remodeling (FIGS. 2A-2F) is consistent with other reports and there are no suggestions of reproducible in vitro remodeling of spheroid structures. Given a more robust fabrication process, we hoped that our aggregates had increased capacity for maturation, if provided a suitable in vitro environment.

Figure 3A:
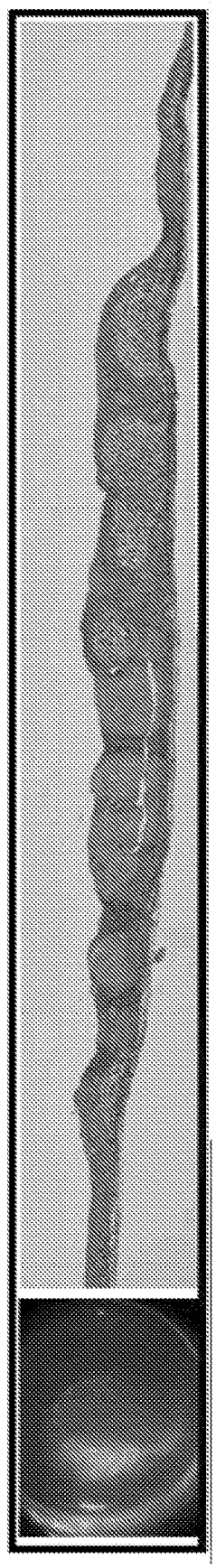
FIG. 3A depict results from implanting HHDP cells into full thickness bioprinted skin.
Figure 3D:
FIGS. 3B-3E depict bioprinted dermal papilla aggregates with a surrounding dermal support (FIG. 3B) with a keratinocyte overlay (FIG. 3C) and after culture for 7 days (FIG. 3D).
Figure 3C:
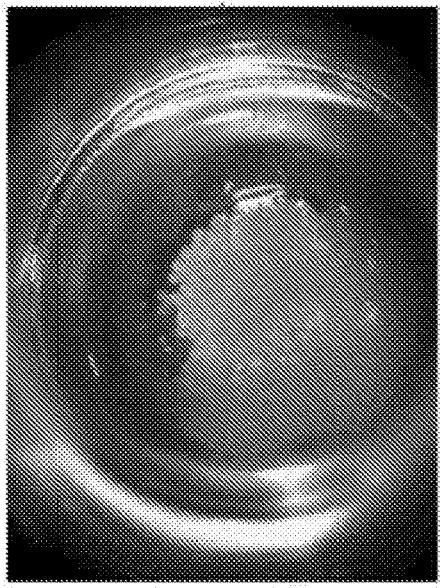
Figure 3B:
Figure 3F:
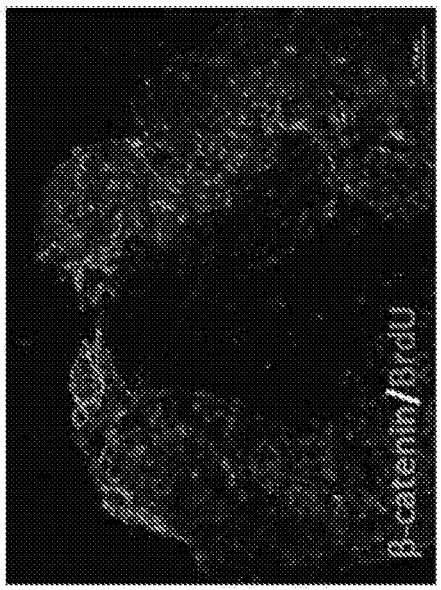
FIGS. 3F-3H depict staining of the printed organoids. There was not dramatic in vivo-like remodeling of the organoids and a common failure mode was aggregation of the organoids within a week.
Figure 3H:
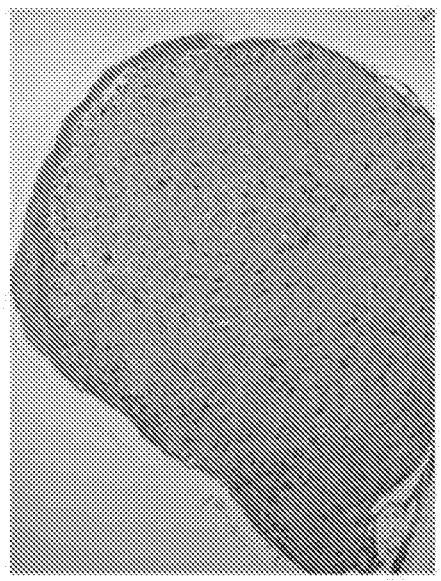
Figure 3E:
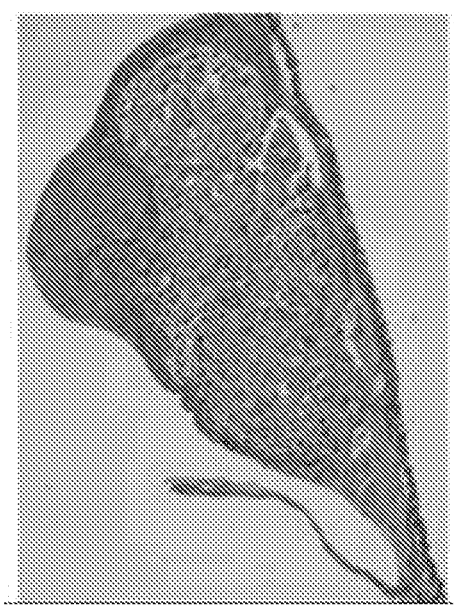
Figure 3G:
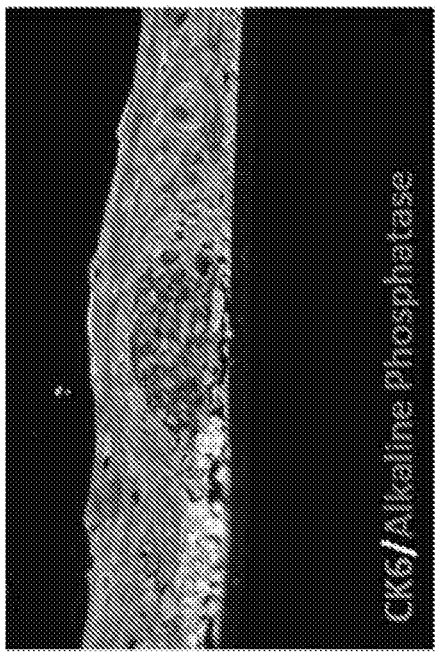

To further push the morphogenesis of aggregates, we attempted several methods of promoting hair formation. First, we introduced aggregates into bioprinted skin tissue (see, e.g., U.S. Publ. Appl. 2016/0122723 for methods of making bioprinted skin tissue). Results (FIG. 3A) were inconsistent and lacked the morphogenesis and cyst formation observed in vivo. Second, we deposited aggregates onto layers of dermal fibroblasts and added extracellular matrix (FIGS. 3B-3D). This was unsuccessful because instead of remaining as individual hair forming structures, aggregates further coalesced into large structures without signs of additional morphogenesis (FIGS. 3E-3H). Finally, aggregates were deposited and covered with a pseudo-epidermis composed of keratinocytes. This approach also failed to induce remodeling of cell aggregates. These experiments led us to believe that inducing remodeling of hair follicle aggregates in vitro posed significant technical engineering challenges and alternative approaches were required to overcome these barriers.

Example 2

Deposition of Cells into Hydrogel Channels

Figure 4:
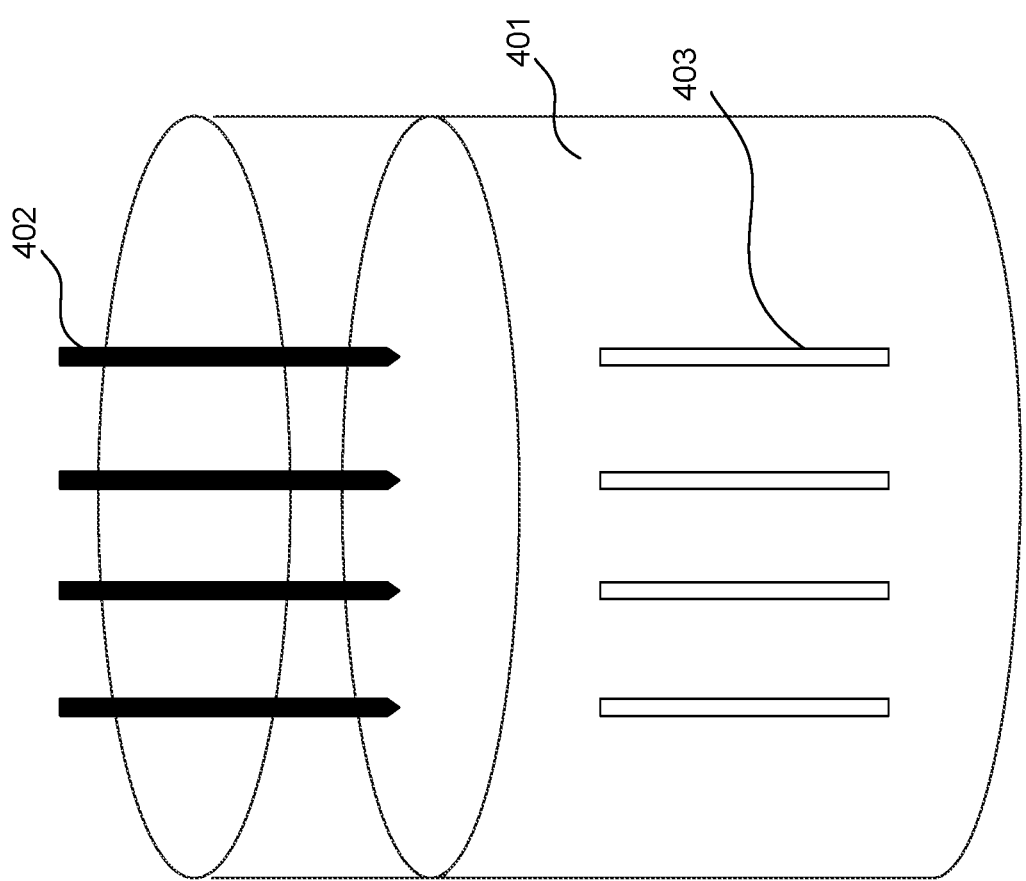
FIG. 4 is a schematic depicting a method to make tissue constructs comprising mesenchymal cells and epithelial cells. The supportive gel (401) is an inert, non-cell adhesive hydrogel (e.g., Novagel®, alginate, or hyaluronic acid). The cells comprise 100% epithelial and mesenchymal cells (70:30 ratio) and are inserted into the gel by a plurality of needles (402) (e.g., 500 µm, beveled 30° 30 mm) to give channels (403). The units are cultured for 7-21 days or more.

The failures described in Example 1 led us to develop new methods that included automated fabrication, eliminated aggregation, and incorporated polarity, which was expected to aid in subsequent transplantation procedures. A first method of bioprinting follicular units was developed with significantly improved results compared to the cell aggregate experiments. This method involved bioprinting discrete follicle channels that include the relevant cell types within a hydrogel. FIG. 4 depicts insertion of needles containing the cells into the hydrogel to form channels.

Prior to preparation of cells, a hydrogel base is poured. The hydrogel composition was optimized and focused on biocompatible materials with low cell adhesive properties to promote aggregation. Agarose, alginate and hyaluoric acid (HA) were chosen and tested as the lead candidates. Hydrogels were made and deposited into a well with sufficient time for crosslinking. As tested, the hydrogel was acellular but may contain other cell types such as dermal fibroblasts, endothelial cells, pre-adipocytes or immune cells may be incorporated. Additionally, the construct was designed such that cellular channels within the gel as well as a small volume of gel would be transplanted. In one embodiment, the hydrogels are compatible with clinical use, strong enough to allow surgical manipulation and useful in dermatology applications.

Hydrogels form a base for a new method of tissue fabrication. A bioprinter deposits channels of cells directly into the hydrogel. A cell mixture is made that includes human dermal papilla cells, human keratinocytes as well as potential accessory cells such as melanocytes or specialized sheath cells. All cells are human, untransformed and fully differentiated. Cells are mixed in various ratios and loaded into a custom Hamilton syringe without excipients. Syringes are placed onto the bioprinter and then printed into the gel using a pre-designed script. The script dictates the number of proto-follicles that are formed and their respective position within the construct. Varying needle size allows control over the diameter of the construct. Once configured, the printer then injects the cell suspension into the hydrogel base forming a channel of cells.

Figure 5B:
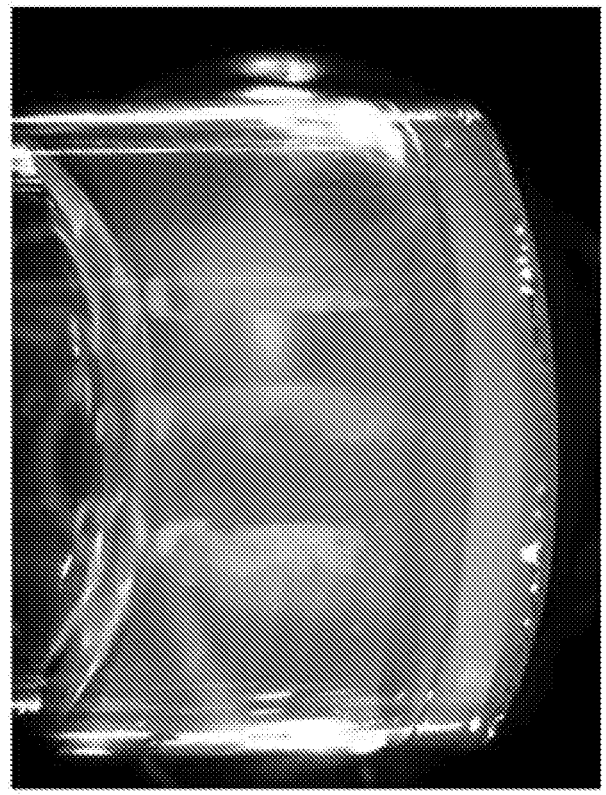
FIGS. 5A-5B depict photographs of 4 mm long cell constructs (made from mixed cells) deposited into a hydrogel with a 260 µm (FIG. 5A) vs. a 515 µm (FIG. 5B) outer diameter sized needle. These results show that the size of the needle is important to obtain channels of cells in the hydrogel. The 500 µm needle worked best.
Figure 5A:
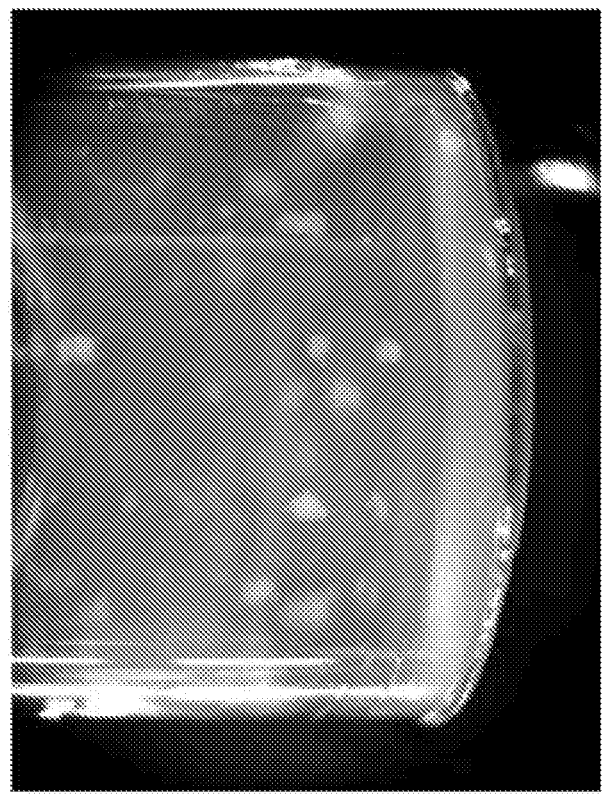

Printing with this method was not immediately feasible as several challenges had to be overcome. First, the hydrogel composition/concentration was optimized so that bioprinter injection created a stable channel to allow continued maintenance of individual units. Second, the tip of the needle was found to be critical. A beveled needle was found to be required to achieve consistent deposition. We tested several different styles and sizes of needles to determine this. Failed attempts led to discontinuous deposition, cells that came out of the top of the channel and fissures in the gel that broke down the intended geometry. FIGS. 5A-5B depict photographs of 4 mm long cell constructs (made from mixed cells deposited into a hydrogel with a 250 µm (FIG. 5A) vs. a 500 µm (FIG. 5B) sized needle. These results show that the size of the needle is important to obtain channels of cells in the hydrogel. FIGS. 6A-6C are photographs depicting the effect of various types of hydrogel compositions (FIG. 6A, rat-tail collagen (6 mg/ml); FIG. 6B, gelatin (8%); FIG. 6C, laminin/fibronectin (15 µg/ml±12.5)) on cellular construct maturation and cohesion within the channels. These results indicate that the addition of extracellular matrix (ECM) did not significantly improve deposition.

Characterization of optimized channel prints cultured for 1 to 3 weeks revealed remodeling into follicle-like structures (FIGS. 8A-8DF). Within the channels, cyst structures were commonly found. This finding is in contrast to aggregates maintained in vitro but similar to remodeling after in vivo injection. Again, the channel prints were never exposed to in vivo conditioning. Cysts that form in bioprinted channels often contain dermal papilla cells, suggesting a positive correlation between remodeling and the reciprocal signaling between the mesenchymal and epithelial cell types. Staining of the epithelial cells with markers such as CK15, EpCam and CK6 further supported differentiation of keratinocytes consistent with follicle morphogenesis.

Figure 8A:
FIGS. 8A-8D are micrographs of paste-only prints in which 100% cellular mixtures of dermal cells are bioprinted into the desired follicle unit geometry and then cultured for 14 days (FIG. 8A) and 21 days (FIGS. 8B-8D).
Figure 8B:
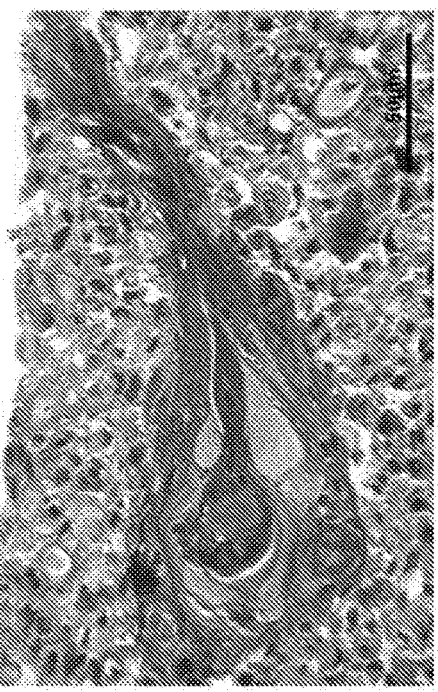
Figure 8C:
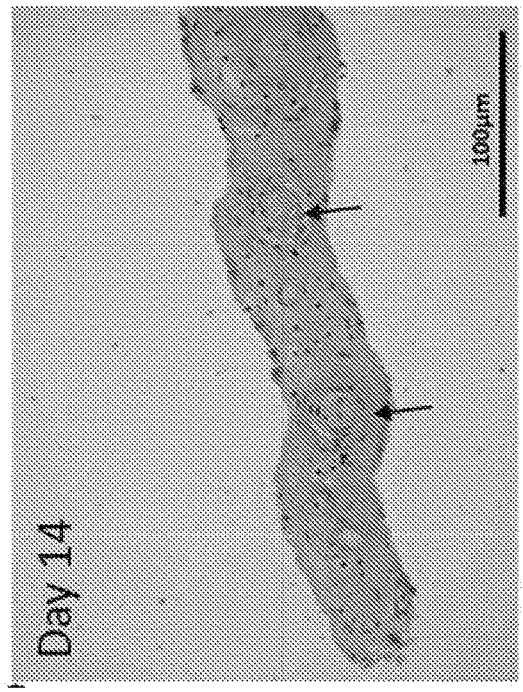
Figure 8D:
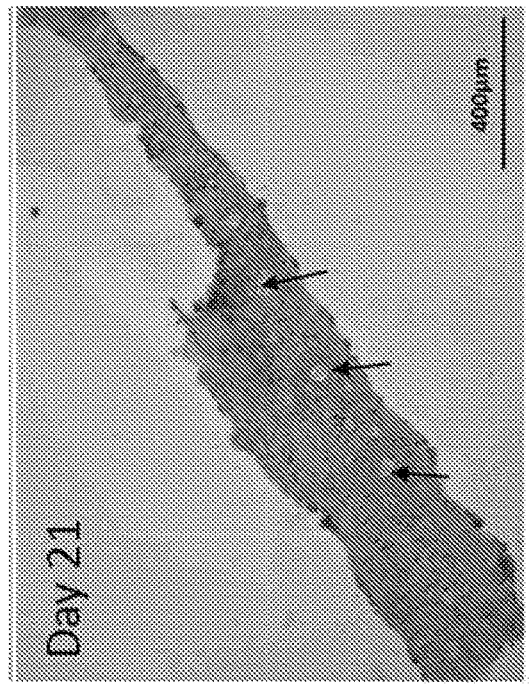

FIGS. 8A-8D are micrographs of paste-only prints in which 100% cellular mixtures are automatically deposited as channels into a preformed hydrogel and then cultured for 14 days (FIG. 8A) and 21 days (FIGS. 8B-8D). These tissue constructs developed cyst formation characteristic of hair follicles. Small amounts of ECM can be added to the cell mixture to drive cyst maturation (FIG. 8D).

Figure 9A:
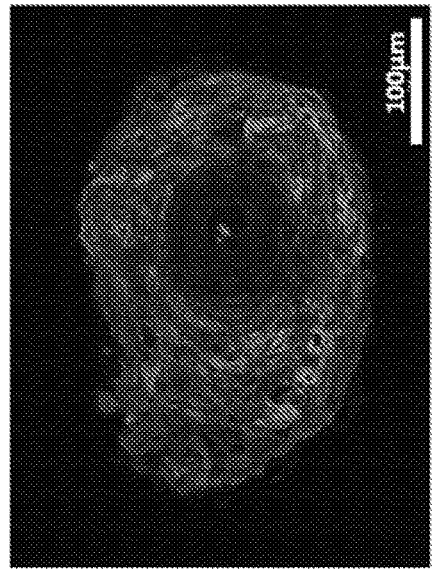
FIGS. 9A-9F depict micrographs of the cysts with BrdU+ staining when cultured for 14 days (FIGS. 9A-9C) and 21 days (FIGS. 9D-9F). The BrdU+ staining shows the presence of dermal papilla cells in the cysts.
Figure 9B:
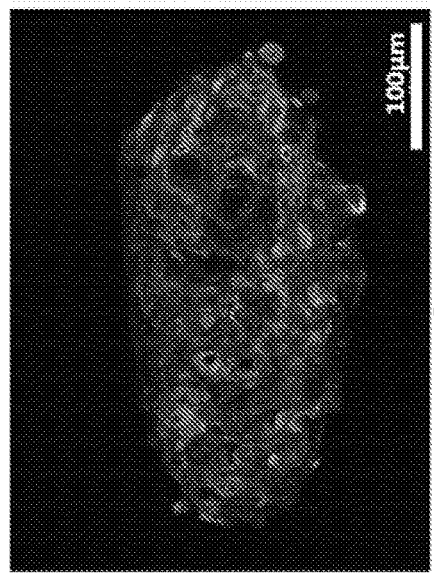
Figure 9C:
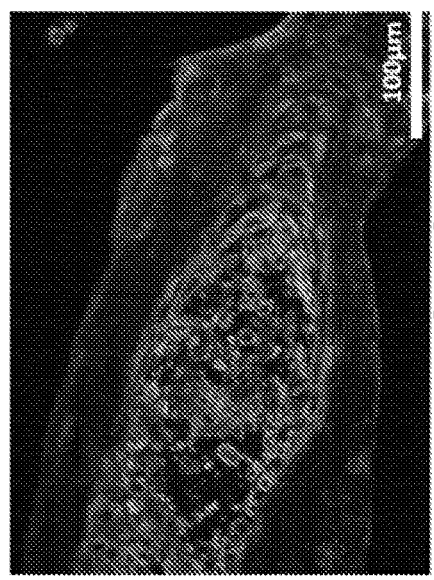
Figure 9D:
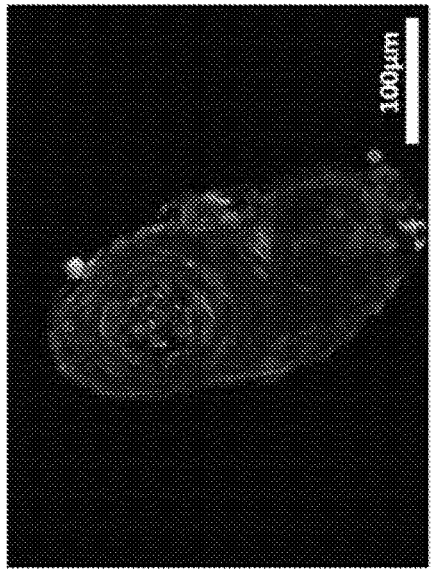
Figure 9E:
Figure 9F:
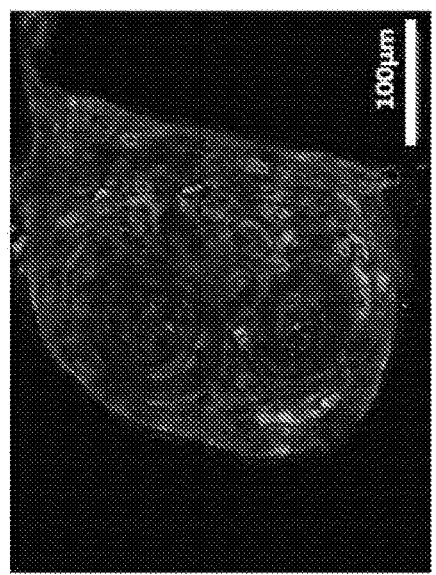
Figure 10A:
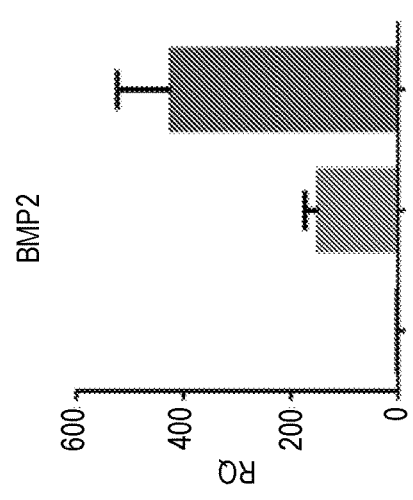
FIGS. 10A-10F are bar graphs (FIGS. 10A-10C) and micrographs (FIGS. 10D-10F) showing that gene expression in the cysts changed quickly over 2, 5 and 21 days and suggests more robust induction when compared to spheroids.
Figure 10B:
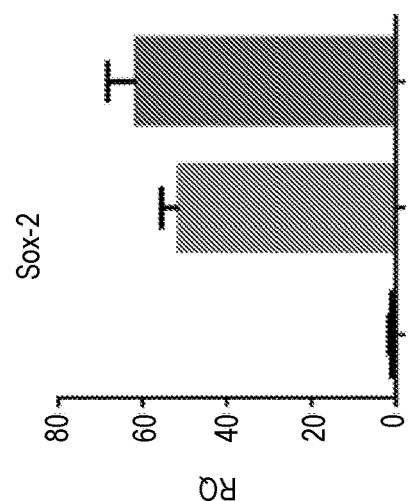
Figure 10C:
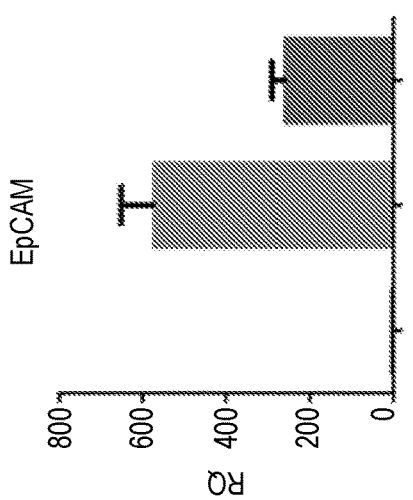
Figure 10D:
Figure 10E:
Figure 10F:
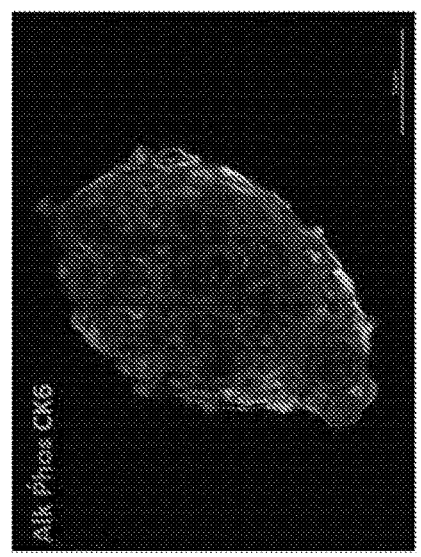

FIGS. 9A-9F depict micrographs of the cysts with BrdU+ staining when cultured for 14 days (FIGS. 9A-9C) and 21 days (FIGS. 9D-9F). The BrdU+ staining shows the presence of dermal papilla cells in the cysts.

FIGS. 10A-10F are bar graphs (FIGS. 10A-10C) and micrographs (FIGS. 10D-10F) showing that gene expression in the cysts changes quickly over 2, 5 and 21 days.

Figure 11C:
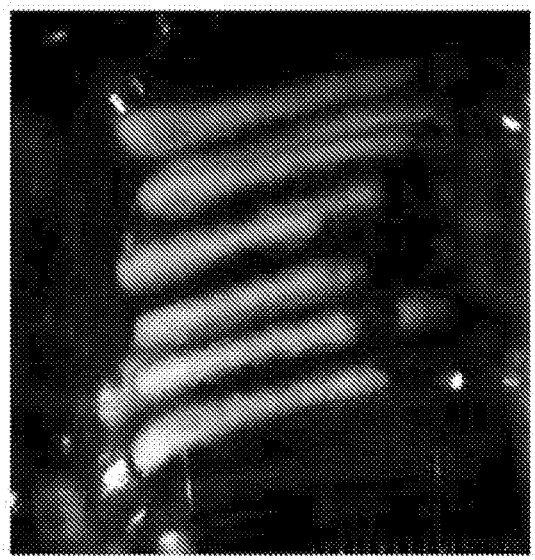
FIGS. 11A-11C are photographs of deposited cell paste in alginate gel. Use of an alginate gel resulted in very smooth deposition compared to other hydrogels. Although some channels had a cap of cells, they were much less frequent than with other hydrogels.
Figure 11B:
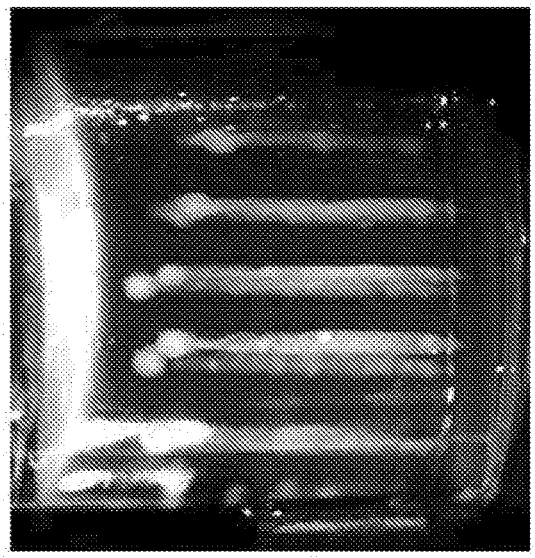
Figure 11A:

FIGS. 11A-11C are photographs of deposited cell paste in alginate gel. Use of an alginate gel resulted in very smooth deposition compared to other hydrogels. Although some channels had a cap of cells, they were much less frequent than with other hydrogels.

Figure 12A:
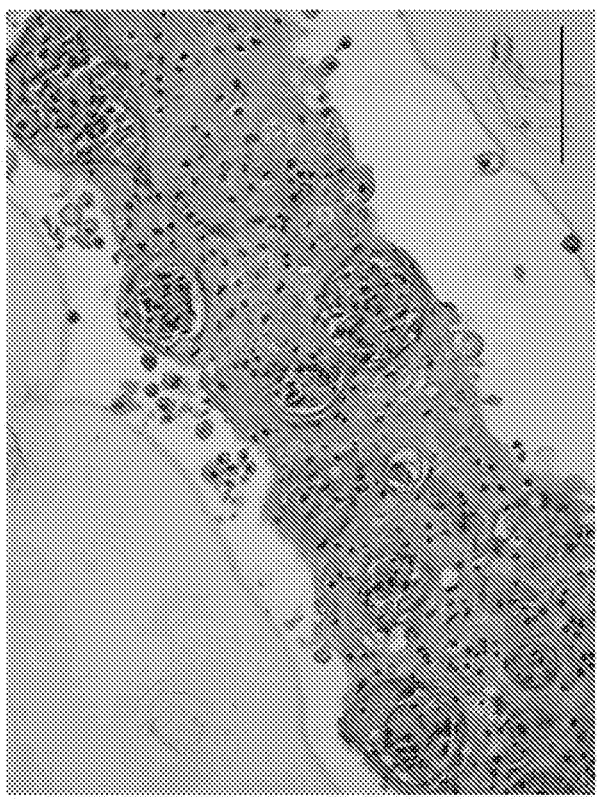
FIGS. 12A-12B are micrographs of tissue constructs deposited in alginate after 7 days. Cysts formed quickly and efficiently in the alginate gel.
Figure 12B:

FIGS. 12A-12B are micrographs of tissue constructs deposited in alginate after 7 days. Cysts formed quickly and efficiently in the alginate gel.

Figure 13B:
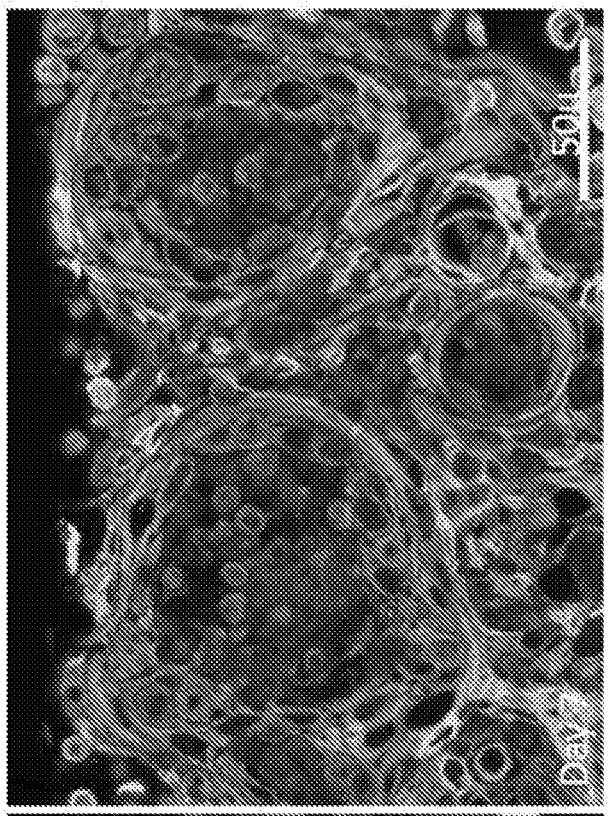
FIGS. 13A-13B are micrographs of tissue constructs at day 1 (FIG. 13A) and day 7 (FIG. 13B) showing that, over time, partitioning of cysts became more organized.
Figure 13A:
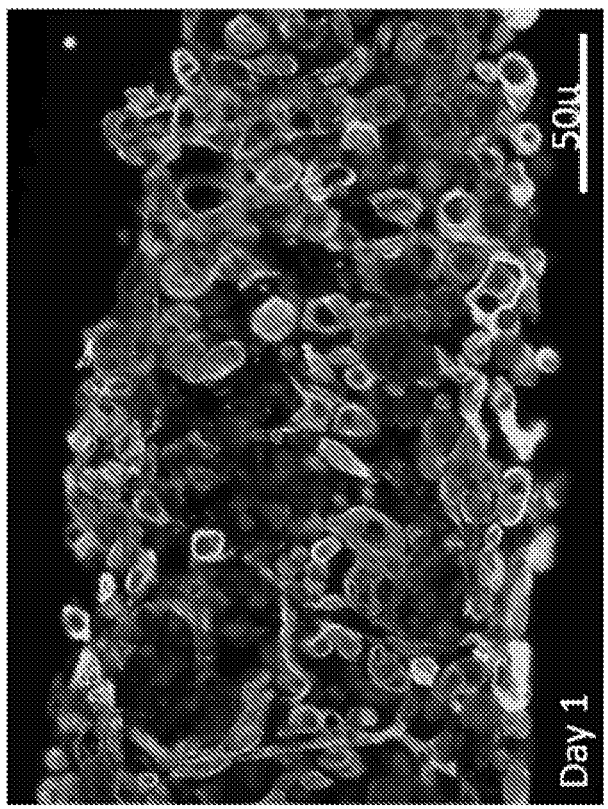
Figure 14B:
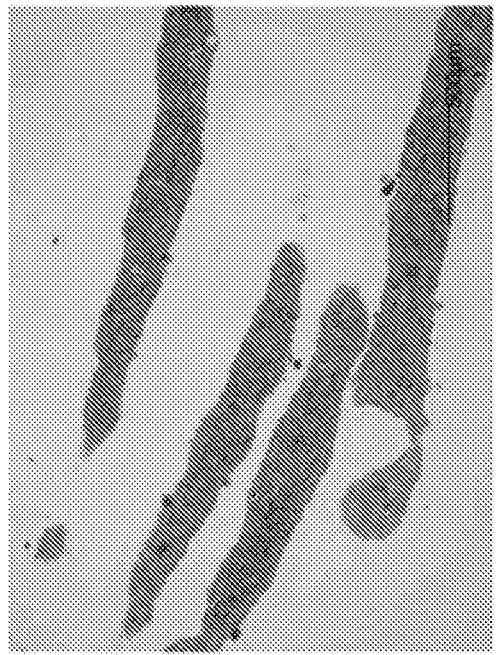
FIGS. 14A-14D are micrographs of tissue constructs 14 days post deposition showing formation of cyst-like structures in tissue constructs.
Figure 14D:
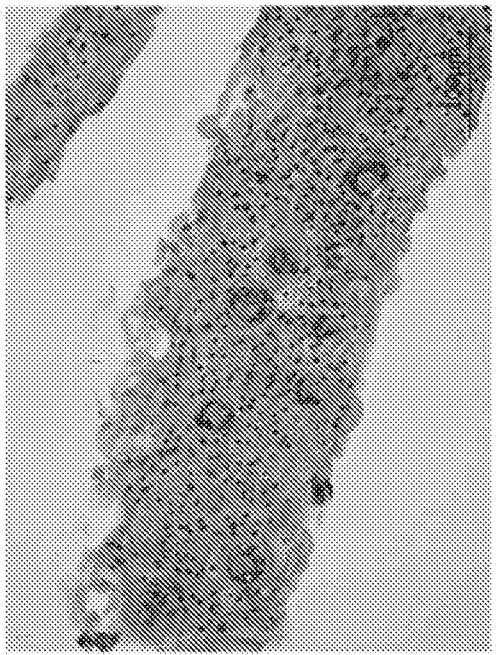
Figure 14A:
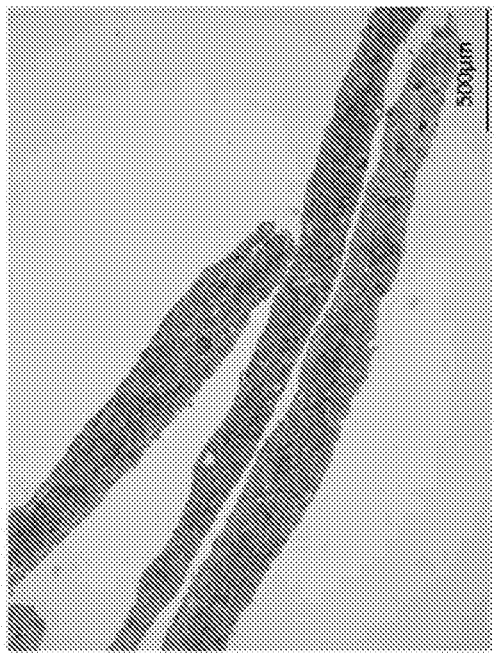
Figure 14C:
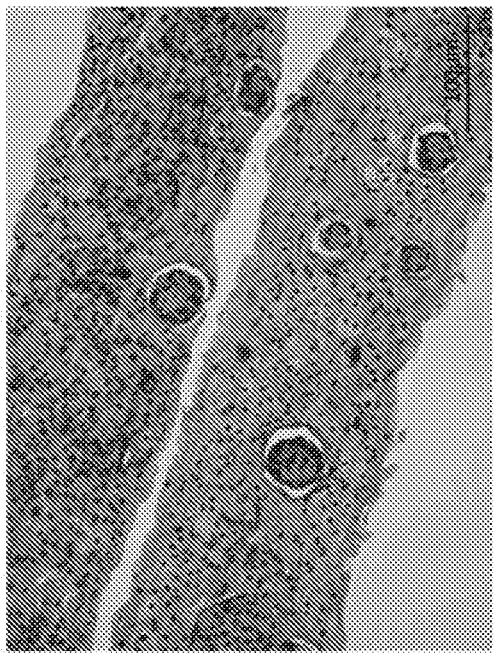
Figure 15A:
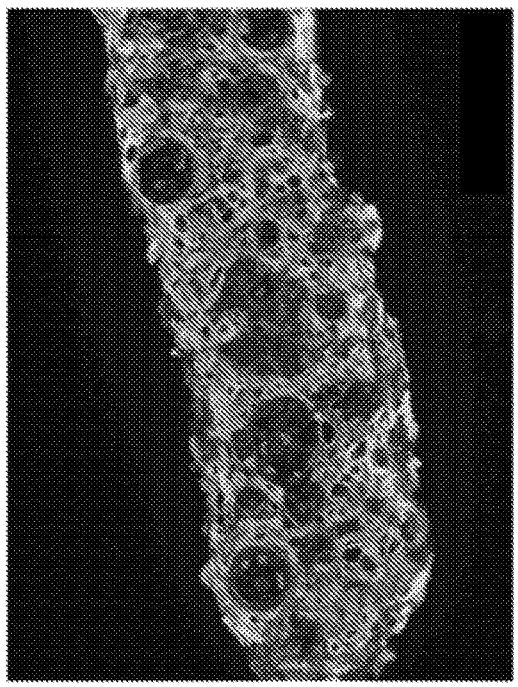
FIGS. 15A-15D are micrographs of tissue constructs stained at 14 days post deposition with BrdU (red) and CK6 (green). The staining pattern shows that the cells persist and are evenly distributed in the tissue construct.
Figure 15B:
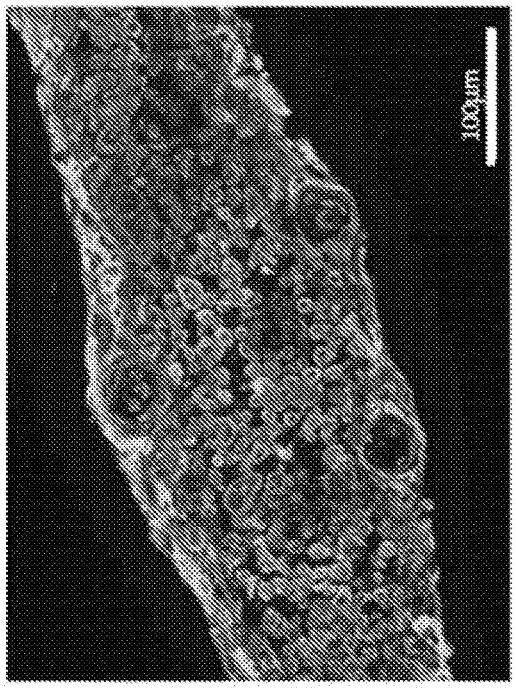
Figure 15C:
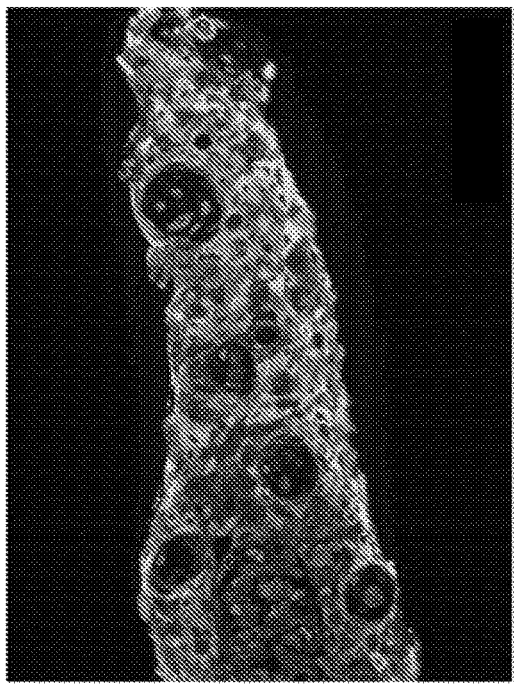
Figure 15D:
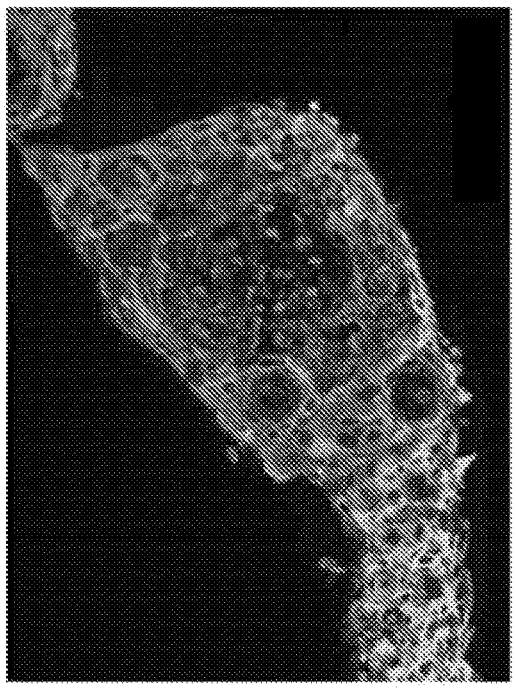

FIGS. 13A-13B are micrographs of tissue constructs at day 1 (FIG. 13A) and day 7 (FIG. 13B) showing that, over time, partitioning of cysts became more organized.

FIGS. 14A-14D are micrographs of tissue constructs 14 days post deposition showing formation of cyst-like structures in tissue constructs.

FIGS. 15A-15D are micrographs of tissue constructs stained at 14 days post deposition with BrdU (red) and CK6 (green). The staining pattern shows that the cells persist and were evenly distributed in the tissue construct.

Figure 16:
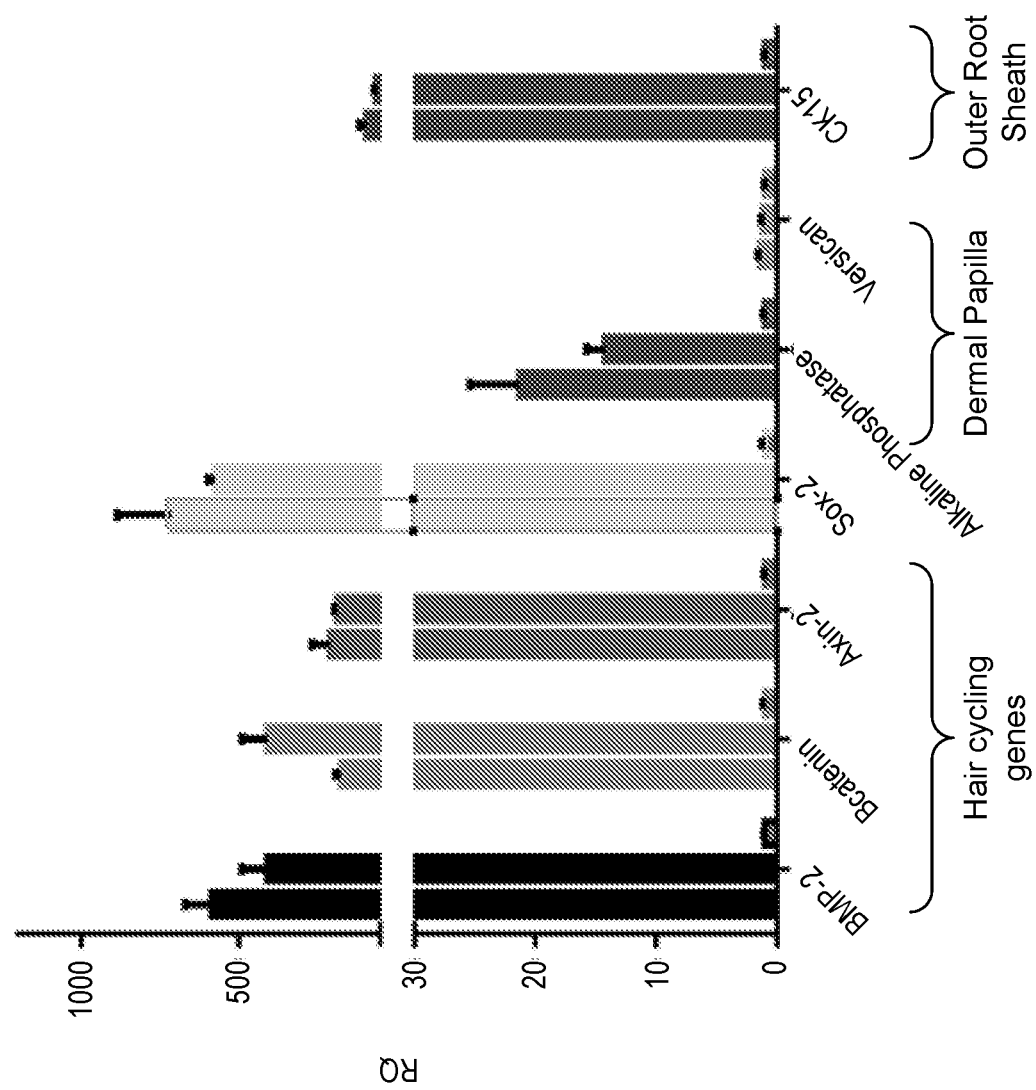
FIG. 16 is a bar graph showing that, at day 15, the tissue constructs manifest up-regulation of follicle associated genes.

FIG. 16 is a bar graph showing that, at day 15, the tissue constructs manifest up-regulation of follicle associated genes.

After 1 week of culture bioprinted channels were removed from the well and were manipulated successfully with surgical tools. This established that the technique is capable of (1) proto-follicle formation, (2) patterned deposition of relevant cell types and (3) material competent for surgical installation.

Example 3

Deposition of Cells with a Coaxial Needle to Make a Segmented Tissue Construct

In one embodiment, a coaxial needle introduces two different cell populations utilizing a single needle punch into the hydrogel. The process is as follows: 1) The coaxial nozzle has two independent flow streams with a common exit orifice. The two cell types are loaded in a fashion such that the dermal papilla cells occupy the core flow path and the keratinocytes occupy the mantle flow path. 2) The coaxial needle enters the hydrogel vertically to an appropriate depth. 3) A bolus of papilla cells is delivered via the core flow path. 4) As the coaxial needle is retracted from the hydrogel, keratinocytes are backfilled utilizing the mantle flow. In this fashion a single injection delivers both cell types in the desired segmentation.

Figure 17:
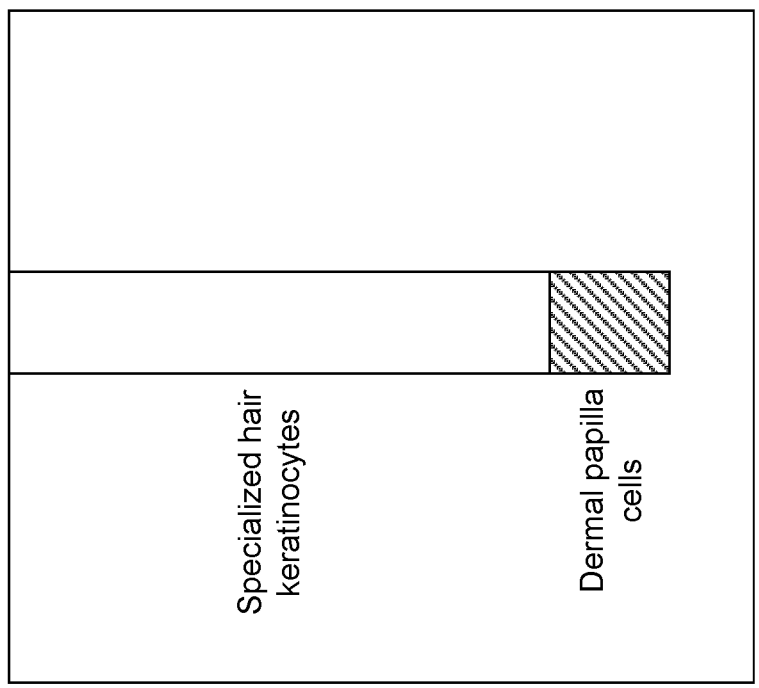
FIG. 17 depicts a segmented construct with dermal papilla cells at the bottom and keratinocytes at the top of the channel.

FIG. 17 depicts a segmented construct with dermal papilla cells at the bottom and keratinocytes at the top of the channel.

Figure 18:
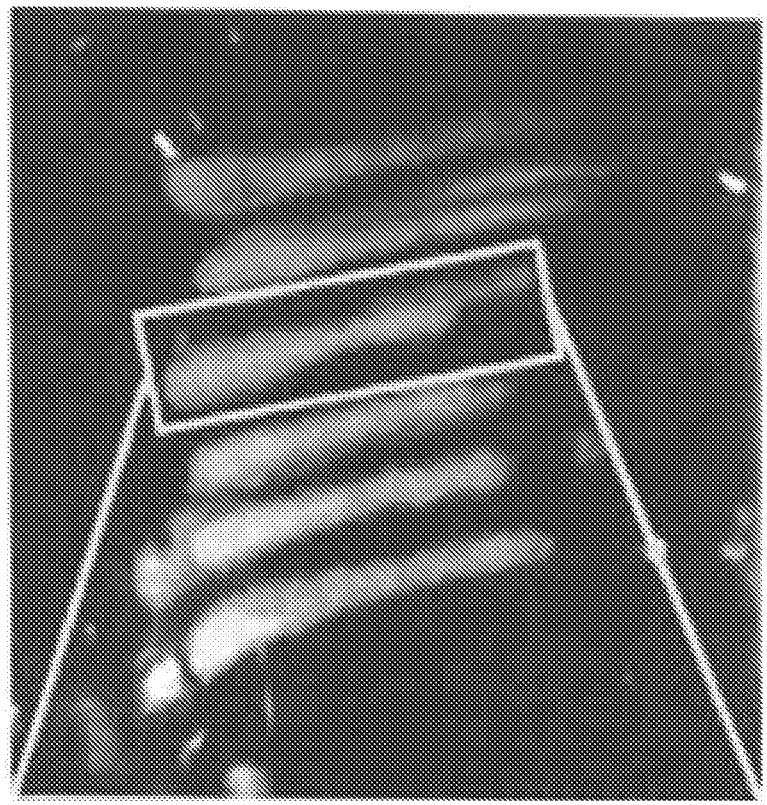
FIG. 18 is a photograph of channels deposited in a alginate with dermal papilla cells at the bottom and keratinocytes at the top. Good verticality and clustering of homogeneous cells mixtures was obtained.

FIG. 18 is a photograph of channels deposited in alginate with dermal papilla cells at the bottom and keratinocytes at the top. Good verticality and clustering of homogeneous cells mixtures was obtained.

FIGS. 19A-19B depict a coaxial needle providing concentric flow of two different inputs for two different types of cells, e.g., wherein the mesenchymal cells are extruded from the core and the epithelial cells are extruded from a mantle layer. FIG. 19B depicts a magnified portion of the end of the needle showing a 30° bevel.

FIGS. 20A-20E depict the coaxial needle delivery technique. FIG. 20A depicts the coaxial needle, primed with mesenchymal cells in the core and epithelial cells are in the mantle layer, wherein the needle is position on top of the hydrogel. FIG. 20B depicts the injection of the needle into the hydrogel. FIG. 20C depicts injection of the mesenchymal cells into the hydrogel. FIG. 20D depicts injection of the epithelial cells as the needle is withdrawn. FIG. 20E depicts the withdrawn needle above the hydrogel containing a channel with mesenchymal cells segmented at the bottom of the channel and epithelial cells segmented at the top of the channel.

Figure 22:
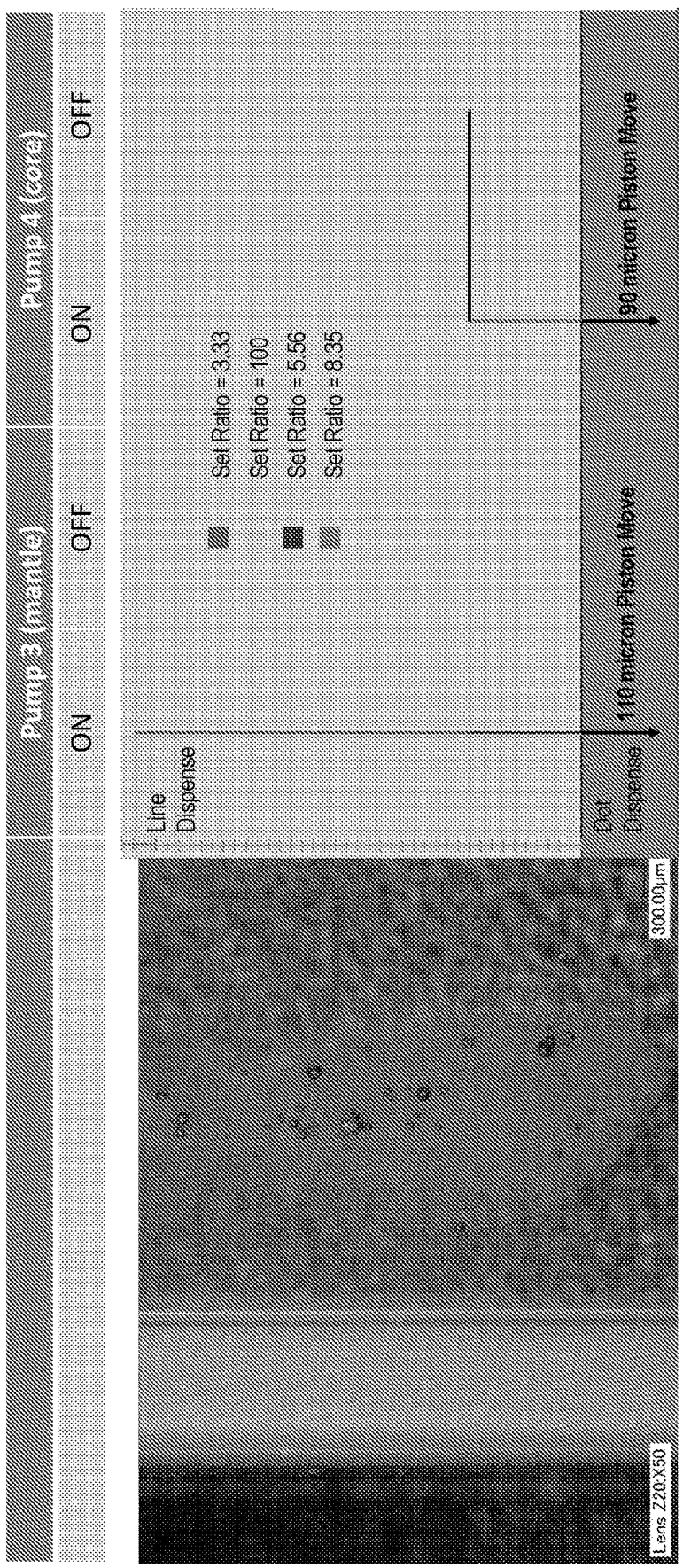
FIG. 22 (left panel) depicts a micrograph showing the results of the coaxial deposition of two different bead solutions according to a deposition program (right panel) using a bioprinter containing 4 pumps.

FIG. 22 (left panel) depicts the results of the coaxial deposition of two different bead solutions according to a deposition program (right panel) using a bioprinter containing 4 pumps. The core material delivered by pump 4 contained yellow dyed 10 micron beads. The mantle material in delivered by pump 2 contained violet dyed 10 micron beads. Tick-marks are spaced in intervals of 100 microns (to scale of image). The needle tip was inserted into the gel position labeled A. The duration of the following movements is below the dashed line. The needle is moved up 700 microns. Pump piston 3 is then moved 110 microns to deposit mantle material, while pump 4 is also moved 90 microns to simultaneously deposit core material. The duration of withdrawal is above the dashed line. During the first 1000 microns of travel, both core and mantle material are being deposited. During the subsequent 3000 microns, only mantle material was deposited.

Figures 23A, 23B:
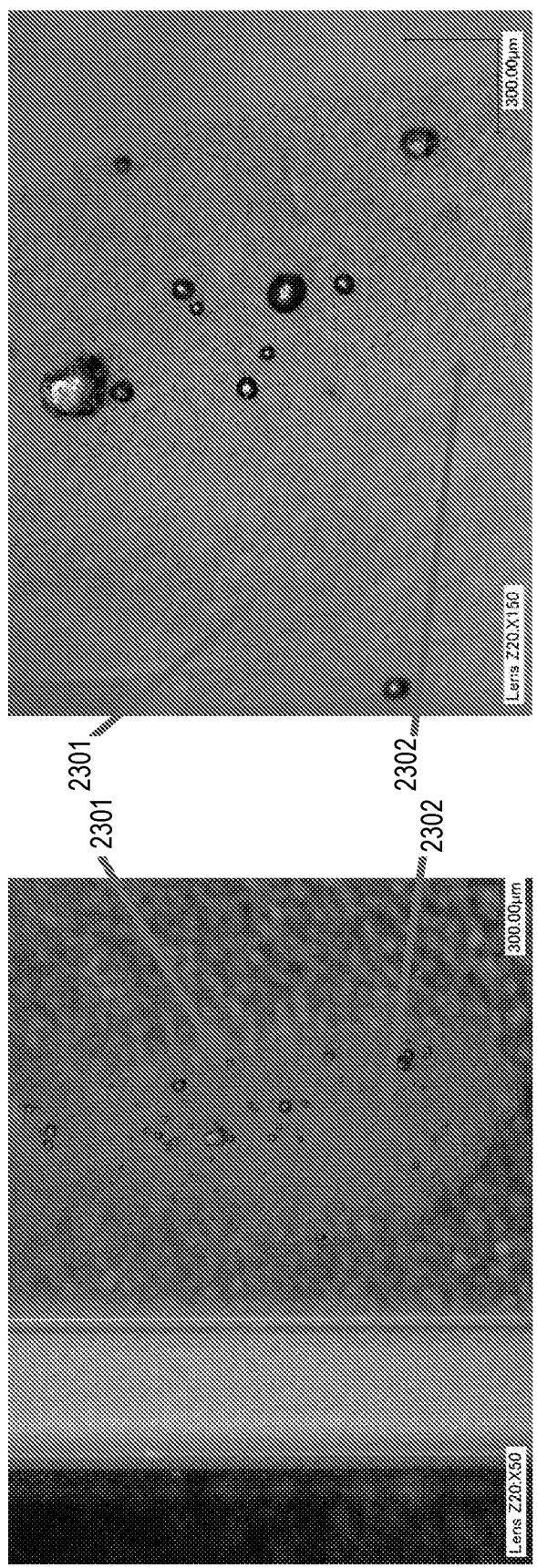
FIGS. 23A-23B depict micrographs showing the results of coaxial deposition.

FIGS. 23A-23B depict micrographs showing the results of coaxial deposition. The core of the needle was connected to pump-head 4 syringe, which contained yellow micron particles suspended in Novogel 2.0. The mantle of the needle was connected to pump-head 3 syringe, which contained violet micron particles suspended in Novogel 2.0. The material was deposited into solid Novogel 2.0 (which is optimal for imaging) contained within a cuvette. The micrographs showed outer material (2301) (violet micron particles suspended in Novogel 2.0) and inner material (yellow micron particles suspended in Novogel 2.0).

Example 4

Deposition of Cells with a Single Compartment Needle to Make a Segmented Tissue Construct Another technique relies on a standard single compartment needle that is connected to a hypodermic syringe loaded with keratinocytes. The needle then proceeds to a vial containing dermal papilla cells and aspirates a small bolus. Thus within the single compartment needle exists the desired stratification that will be extruded as-is into the hydrogel with a single needle injection.

FIGS. 21A-21D depict this method of providing segmented channels where a needle is first primed with mesenchymal cells and placed over a vessel containing epithelial cells (FIG. 21A), the needle is inserted into the epithelial cells and the epithelial cells are aspirated into the needle (FIG. 21B), the needle is then inserted into the hydrogel (FIG. 21C), and the needle with withdrawn from the hydrogel concurrent with the injection of the mesenchymal cells and epithelial cells (FIG. 21D) to give a channel with mesenchymal cells segmented at the bottom of the channel and epithelial cells segmented at the top of the channel.

Figure 24A:
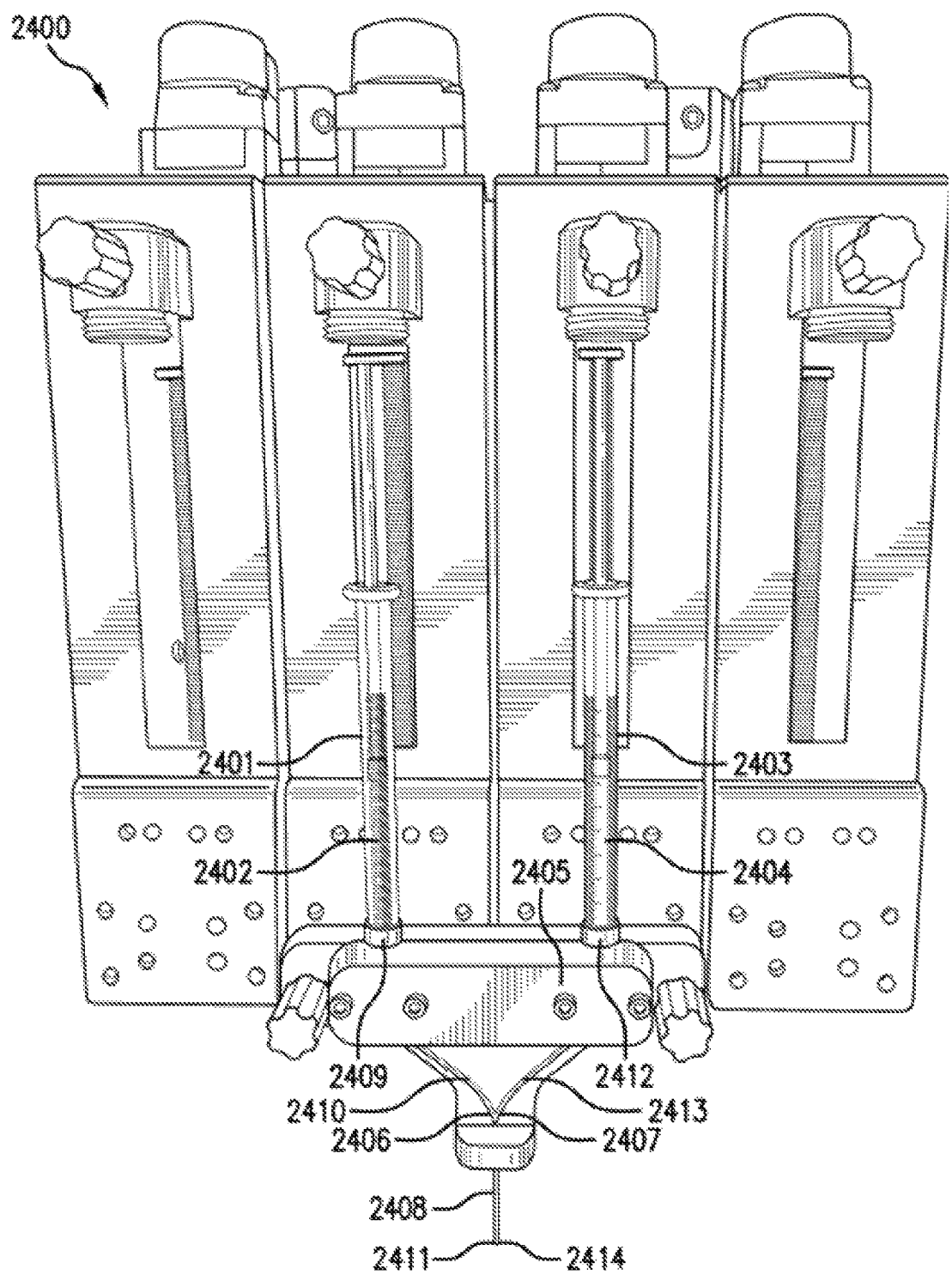
FIGS. 24A-24C depict an exemplary embodiment of the parallel bio-printing system disclosed herein, with FIG. 24A and FIG. 24C depicting side views, and FIG. 24B depicting a bottom view.
Figure 24B:
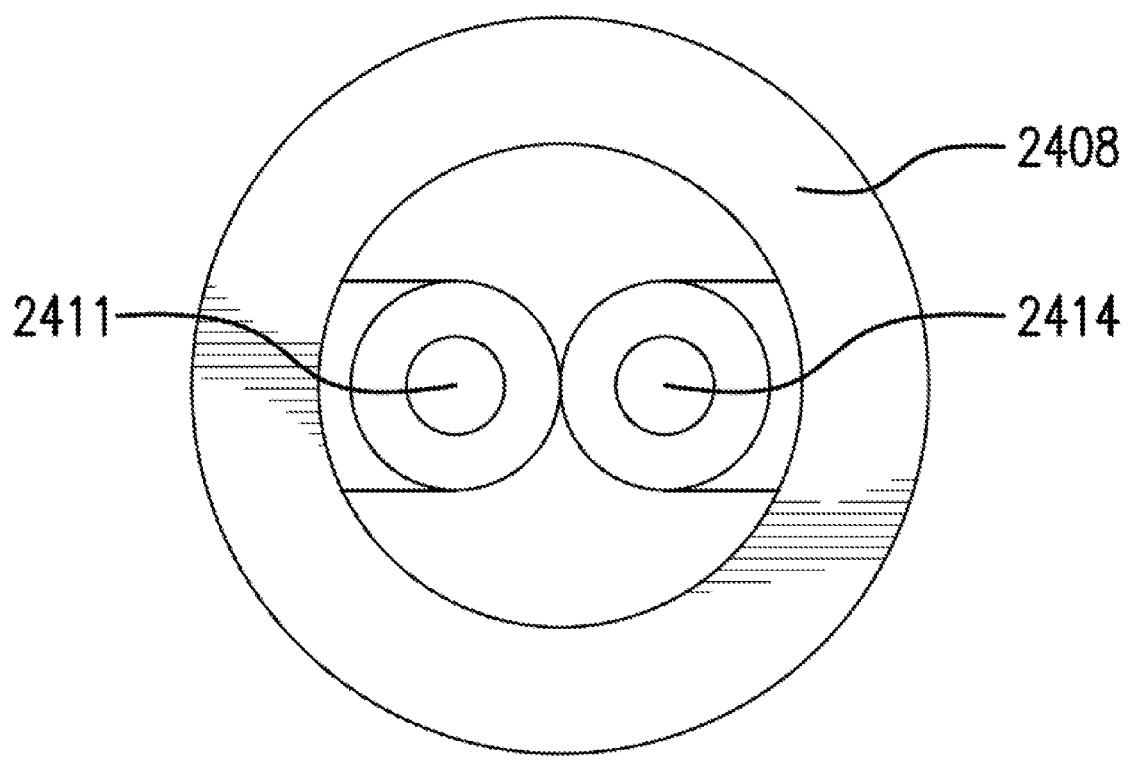
Figure 24C:
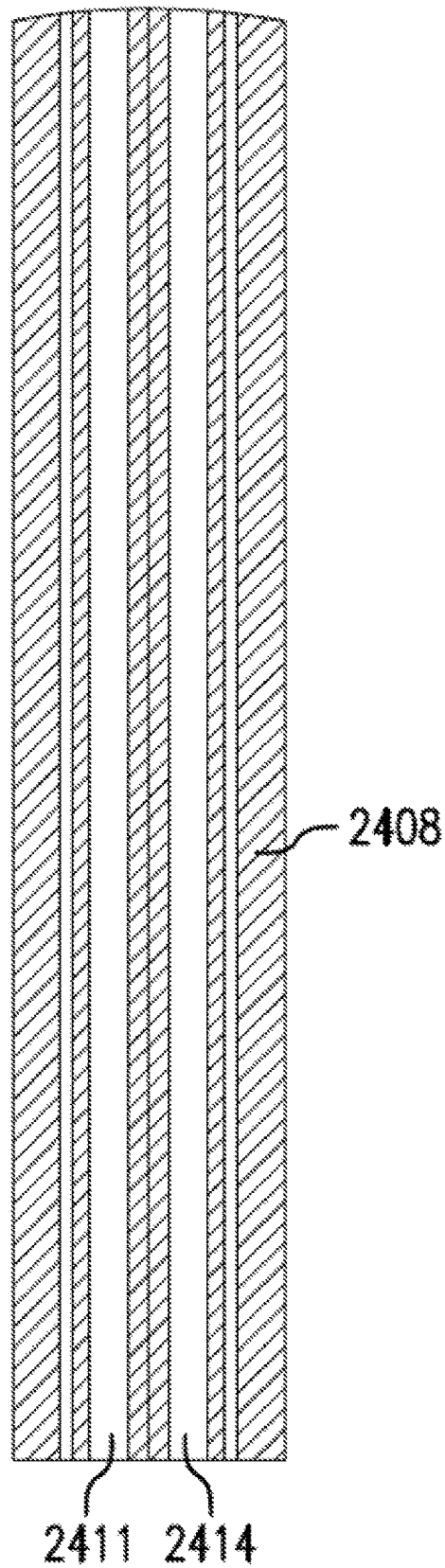

FIGS. 24A-24C depict an exemplary embodiment of the parallel bio-printing system 2400 disclosed herein, with FIG. 24A and FIG. 24C depicting side views, and FIG. 24B depicting a bottom view. As shown in FIG. 24A, the parallel bio-printing system 2400 comprises the first dispenser 2401, the second dispenser 2403, and the common dispense module 2405. The first dispenser 2401 comprises a first bio-ink 2402 and a first outlet (not shown). The second dispenser 2403 comprises a second bio-ink 2404 and a second outlet (not shown). The first dispenser 2401 and the second dispenser 2403 are extrusion-based dispensers, such as an automated syringe dispenser or a pneumatic-actuated dispenser. Other types of dispensers suitable for bio-printing are possible with the first dispenser 2401 and the second dispenser 2403. Although not shown, the first outlet and the second outlet is a dispense outlet, such as a dispense tip. As shown in FIG. 24A, the first outlet of the first dispenser 2401 is coupled to the first inlet 2409 of the first module 2406 and the second outlet of the second dispenser 2403 is coupled to the second inlet 2405 of the second module 2407.

In this exemplary embodiment of FIG. 24, the first bio-ink 2402 has a different composition of human cells from the second bio-ink 2404. The first bio-ink 2402 comprises epithelial cells, and specifically, dermal epithelial cells, and more specifically, keratinocytes. The second bio-ink 2404 comprises mesenchymal cells and specifically, dermal papilla cells. Other cell types and/or other cell concentrations of the same or different cell types of the first and second bio-inks are possible. For brevity, the different types of the first and second bio-inks are described in the "PARALLEL BIO-PRINTING SYSTEM FOR BIO-PRINTING CELLULAR CONSTRUCT" section.

As shown in FIG. 24A, the first dispenser 2401 affixed to the first module 2406, and the second dispenser 2403 is affixed to the second module 2407. However, the first dispenser 2401 is a separable unit from the first module 2406, and the second dispenser 2403 is a separable unit from the second module 2407. Optionally, the first dispenser 2401 can be in unison with the first module 2406, and the second dispenser 2403 can be in unison with the second module 2407, thereby negating the need of the first outlet (not shown) of the first dispenser 2401, the second outlet (not shown) of the second dispenser 2403, the first inlet 2409, and the second inlet 2405.

As shown in FIG. 24A, the common dispense module 2405 comprises a first module 2406, a second module 2407, and a common outlet 2408. The first module 2406 comprises a first inlet 2409, a first body 2410, and a first dispense tip 2411. The first module 2406 is in fluidic communication with the first dispenser 2401. The second module 2407 comprises a second inlet 2412, a second body 2413, and a second dispense tip 2414. The second module 2407 is in fluidic communication with the second dispenser 2403. As shown in FIG. 24A, the first module 2406 and the second module 2407 form a symmetric configuration.

As shown in FIG. 24B, the common outlet 2408 comprises the first dispense tip 2411 and the second dispense tip 2414. As shown in FIG. 24C, the first dispense tip 2411 is substantially in parallel with the second dispense tip 2414. Also shown in FIG. 24C, the first dispense tip 2411 and the second dispense tip 2414 are also substantially in parallel with the common outlet 2408. Optionally, the first dispense tip 2411 and the second dispense tip 2414 do not have to be substantially in parallel with the common outlet 2408. For example, the common outlet 2408 can protrude from the first dispense tip 2411 and the second dispense tip 2414, such as protruding lower than the first dispense tip 2411 and the second dispense tip 2414, or protruding higher than the first dispense tip 2411 and the second dispense tip 2414. The common outlet can have a diameter of approximately 0.4 mm to 2.0 mm and in this exemplary embodiment of FIGS. 24A-24C, the common outlet 2408 is approximately 1.0 mm in diameter, which corresponds to the approximate diameter of the cellular construct created by the exemplary embodiments of method 2500 described in FIGS. 25A-B.

Optionally, the parallel bio-printing system 2400 can have three or more dispensers, and thus, the components of this system 2400 can be scaled accordingly to meet the higher demand in throughput, or variations in cell types or cell concentrations.

Figure 25A:
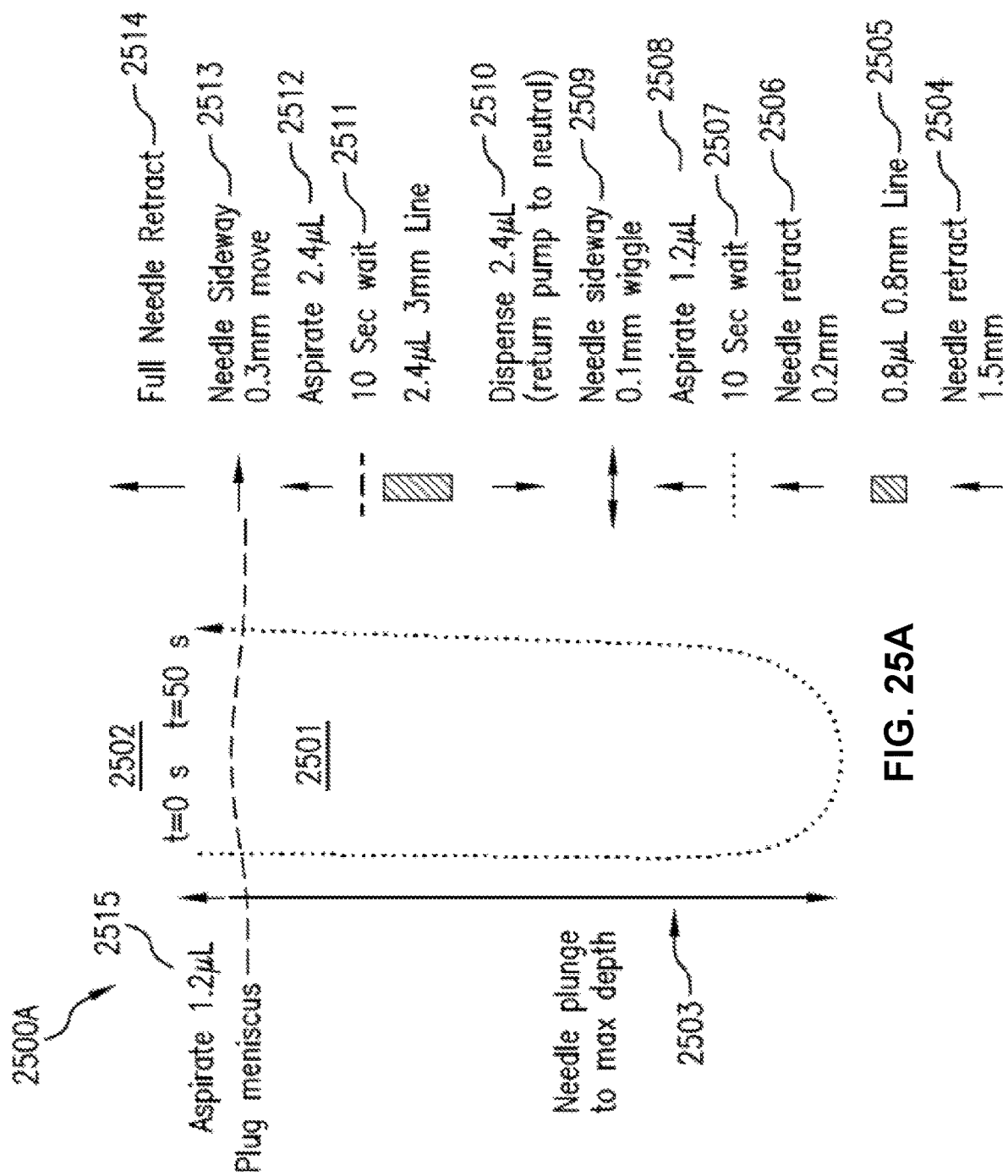
FIGS. 25A-25B depict exemplary embodiments of the parallel bio-printing methods disclosed herein using the exemplary embodiment of the parallel bio-printing system described in FIGS. 24A-C.
Figure 25B:
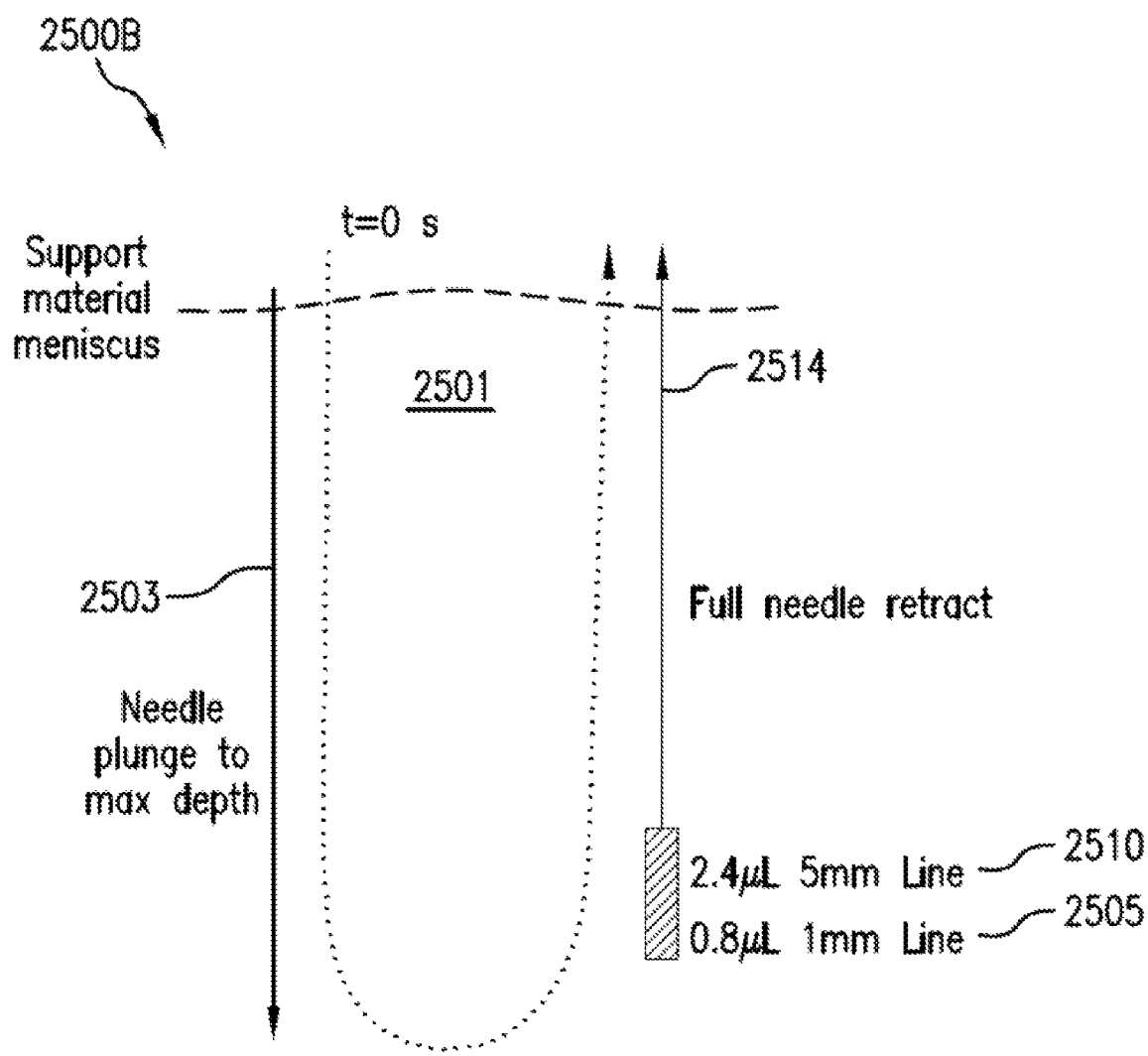

FIGS. 25A-25B depict exemplary embodiments of the parallel bio-printing methods 2500A-B disclosed herein using the exemplary embodiment of the parallel bio-printing system 2400 described in FIGS. 24A-C. In the exemplary embodiment of FIGS. 25A, the parallel bio-printing method 2500A comprises steps 2503-2514 and optionally, step 2515. At step 2503, the parallel bio-printing system 2400, and in particular the common outlet 2408, descends a pre-determined distance into a semi-solid material 2501. In this embodiment, the pre-determined distance is equal to approximately a maximum depth of the semi-solid material. In this exemplary embodiment of FIGS. 25A-B, the semi-solid material 2501 comprises alginate.

At step 2504, the common outlet 2408 ascends a pre-determined distance of approximately 1.0 to 2.0 millimeters (mm) and in this embodiment, the common outlet 2408 ascends approximately 1.5 mm. At step 2505, the first dispense tip 2411 deposits a pre-determined amount of a first bio-ink 2402 into the semi-solid material 2501, wherein the depositing occurs while the common outlet 2408 is ascending. The dispensed pre-determined amount of the first bio-ink 2402 is approximately 0.8 has a substantially straight having a length of approximately 0.8 mm and a diameter of approximately 1.0 mm. Optionally, at step 2505, the pre-determined amount of the first bio-ink 2402 can have a substantially straight having a length of approximately 1.0 mm instead of 0.8 mm, wherein the approximately 0.8 µL is evenly distributed over the 1.0 mm length. The advantage of depositing the approximately 0.8 µL over a length of approximately 0.8 mm instead of 1.0 mm is that the extra 0.2 mm can be additional room for the common outlet 2408 to retract, thereby creating a wider gap between the first bio-ink and the second bio-ink, which reduces the risk of the first bio-ink streaking into the dispensed second bio-ink.

In this exemplary embodiment of FIGS. 25A-25B, the first bio-ink 2402 has a different composition of human cells from the second bio-ink 2404. The first bio-ink 2402 comprises epithelial cells, and specifically, dermal epithelial cells, and more specifically, keratinocytes. The second bio-ink 2404 comprises mesenchymal cells and specifically, dermal papilla cells. Other cell types and/or other cell concentrations of the same or different cell types of the first and second bio-inks are possible. For brevity, the different types of the first and second bio-inks are described in the "PARALLEL BIO-PRINTING METHOD FOR BIO-PRINTING CELLULAR CONSTRUCT" section. At step 2506, the common outlet 2408 ascends approximately 0.2 mm. At step 2507, prior to the depositing the pre-determined amount of the second bio-ink 2404 into the semi-solid material 2501, the method 2500A pauses any action by the common outlet 2408 for a pre-determined amount of time. In the exemplary embodiment of FIG. 25A, at step 2501, this pre-determined amount of time is approximately 10 seconds. At step 2508, prior to the depositing the pre-determined amount of the second bio-ink 2404 into the semi-solid material 2501, the method 2500A aspirates a pre-determined amount of 1.2 µL of the first bio-ink 2402 using the first dispense tip 2411.

At step 2509, prior to the dispense of the pre-determined amount of the second bio-ink 2404, the common outlet 2408 moves a pre-determined length horizontally, and in this exemplary embodiment, the pre-determined length horizontally is approximately 0.1 mm. Optionally, at step 2509, the movement can be a wiggle of the pre-determined length horizontally, and in particular, a wiggle of approximately 0.1 mm. During this step 2509, the common outlet 2408 conducts the following series of horizontal moves, +X 0.1 mm, +Y 0.1 mm, −X 0.1 mm, and −Y 0.1 mm. The motivation for this step 2509 is to encourage the dispensed fire bio-ink to break away from the common outlet 2408, which in turn will reduce the streaking of the first bio-ink into the second bio-ink.

At step 2510, the second dispense tip 2414 deposits a pre-determined amount of a second bio-ink 2404 into the semi-solid material 2501, wherein the depositing occurs while the common outlet 2408 is ascending. The dispensed pre-determined amount of the first bio-ink 2404 is approximately 2.4 µL, has a substantially straight having a length of approximately 3.0 mm and a diameter of approximately 1.0 mm. The second bio-ink 2404 comprises mesenchymal cells and specifically, dermal papilla cells.

At step 2511, after the depositing of the pre-determined amount of the second bio-ink 2404 into the semi-sold material 2501, the method 2500A pauses any action by the common outlet for a pre-determined amount of time. At step 2511 of this exemplary embodiment, this pre-determined amount of time is approximately 10 seconds.

At step 2512, after the depositing of the pre-determined amount of the second bio-ink 2404 into the semi-sold material 2501, the method 2500A aspirates a pre-determined amount of approximately 1.2 µL of the second bio-ink using the second dispense tip.

At step 2513, after the dispense of the pre-determined amount of the second bio-ink 2404, the common outlet 2408 moves a pre-determined length of approximately 0.3 mm horizontally, and subsequently, common outlet 2408 moves vertically out of the semi-solid material 2501.

At step 2514, the common outlet 2408 retracts out of the semi-solid material 2501 to identifier 2502. Identifier 2502 is outside of, and above the surface of, the receiving surface or semi-solid material 2501. Identifier 2502 can be an air medium.

Steps 2503 to 2514 of the parallel bio-printing method 2500A can be completed in approximately 120 seconds or less. The dispensed pre-determined amount of the first bio-ink 2402 and the dispensed pre-determined amount of the second bio-ink 2404 form a cellular construct within the semi-solid material 2501. As such, in the exemplary embodiment of method 2500A, the formed cellular construct comprises approximately 2.8 µL made up of 0.8 µL of dermal papilla cells and approximately 2.4 µL of keratinocytes, has a substantially straight having a length of approximately 3.2 mm (0.8 mm of dermal papilla cells and 2.4 mm of keratinocytes) and a diameter of approximately 1.0 mm.

Optionally, if the user wishes to repeat method 2500a (i.e. two or more cycles), then at step 2515, method 2500a aspirates a pre-determined amount of the second bio-ink 2404 using the second dispense tip 2414, and in particular, the pre-determined amount of the second bio-ink 2404 is approximately 1.2 µL. Subsequent to step 2525, the parallel bio-printing system 2400 will move to different X, Y, Z locations on the receiving surface in order to repeat the method of 2500A in the new desired location.

In the exemplary embodiment of FIG. 25B, the parallel bio-printing method 2500B is a simplified version of the parallel bio-printing method 2500A comprising only steps 2503, 2505, 2510, and 2514. At step 2503, the parallel bio-printing system 2400, and in particular the common outlet 2408, descends a pre-determined distance into a semi-solid material 2501. Identifier 2502 is outside of, and above the surface of, the receiving surface or semi-solid material 2501. In this embodiment, the pre-determined distance is equal to approximately a maximum depth of the semi-solid material. In this exemplary embodiment of FIGS. 25A-B, the semi-solid material 2501 comprises alginate.

At step 2505 of method 2500B, the first dispense tip 2411 deposits a pre-determined amount of a first bio-ink 2402 into the semi-solid material 2501, wherein the depositing occurs while the common outlet 2408 is ascending. The dispensed pre-determined amount of the first bio-ink 2402 is approximately 0.8 µL, has a substantially straight having a length of approximately 1.0 mm (instead of 0.8 mm in method 2500A) and a diameter of approximately 1.0 mm. At step 2505, the pre-determined amount of the first bio-ink 2402 of approximately 0.8 µL is evenly distributed over the 1.0 mm length. In this exemplary embodiment of FIGS. 25A-25B, the first bio-ink 2402 has a different composition of human cells from the second bio-ink 2404. The first bio-ink 2402 comprises epithelial cells, and specifically, dermal epithelial cells, and more specifically, keratinocytes. The second bio-ink 2404 comprises mesenchymal cells and specifically, dermal papilla cells. Other cell types and/or other cell concentrations of the same or different cell types of the first and second bio-inks are possible. For brevity, the different types of the first and second bio-inks are described in the "PARALLEL BIO-PRINTING METHOD FOR BIO-PRINTING CELLULAR CONSTRUCT" section.

At step 2510 of method 2500B, the second dispense tip 2414 deposits a pre-determined amount of a second bio-ink 2404 into the semi-solid material 2501, wherein the depositing occurs while the common outlet 2408 is ascending. The dispensed pre-determined amount of the first bio-ink 2404 is approximately 2.4 µL, has a substantially straight having a length of approximately 3.0 mm and a diameter of approximately 1.0 mm. The second bio-ink 2404 comprises mesenchymal cells and specifically, dermal papilla cells.

At step 2514 of method 2500B, the common outlet 2408 retracts out of the semi-solid material 2501 to identifier 2502. Identifier 2502 is outside of, and above the surface of, the receiving surface or semi-solid material 2501. Identifier 2502 can be an air medium.

The dispensed pre-determined amount of the first bio-ink 2402 and the dispensed pre-determined amount of the second bio-ink 2404 form a cellular construct within the semi-solid material 2501. As such, in the exemplary embodiment of method 2500A, the formed cellular construct comprises approximately 2.8 µL made up of 0.8 µL of dermal papilla cells and approximately 2.4 µL of keratinocytes, has a substantially straight having a length of approximately 3.2 mm (0.8 mm of dermal papilla cells and 2.4 mm of keratinocytes) and a diameter of approximately 1.0 mm.

Figure 26B:
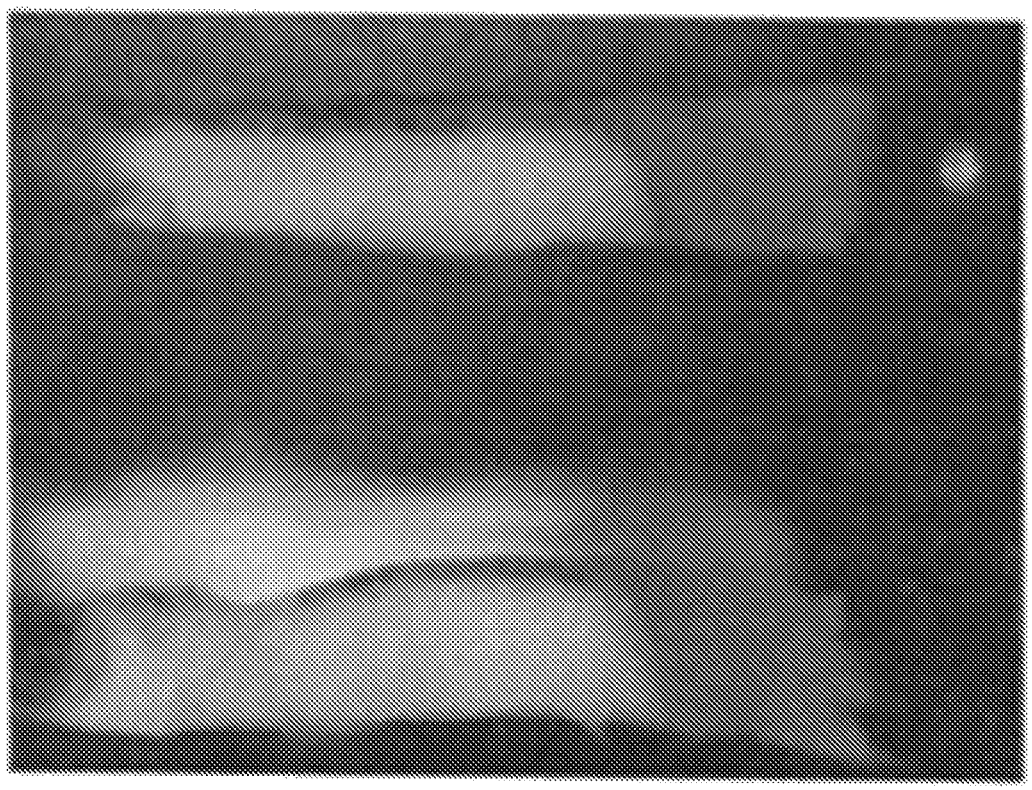
FIGS. 26A-26C depict cellular constructs produced using the parallel bio-printing systems and methods with different pause times and aspiration steps.
Figure 26A:
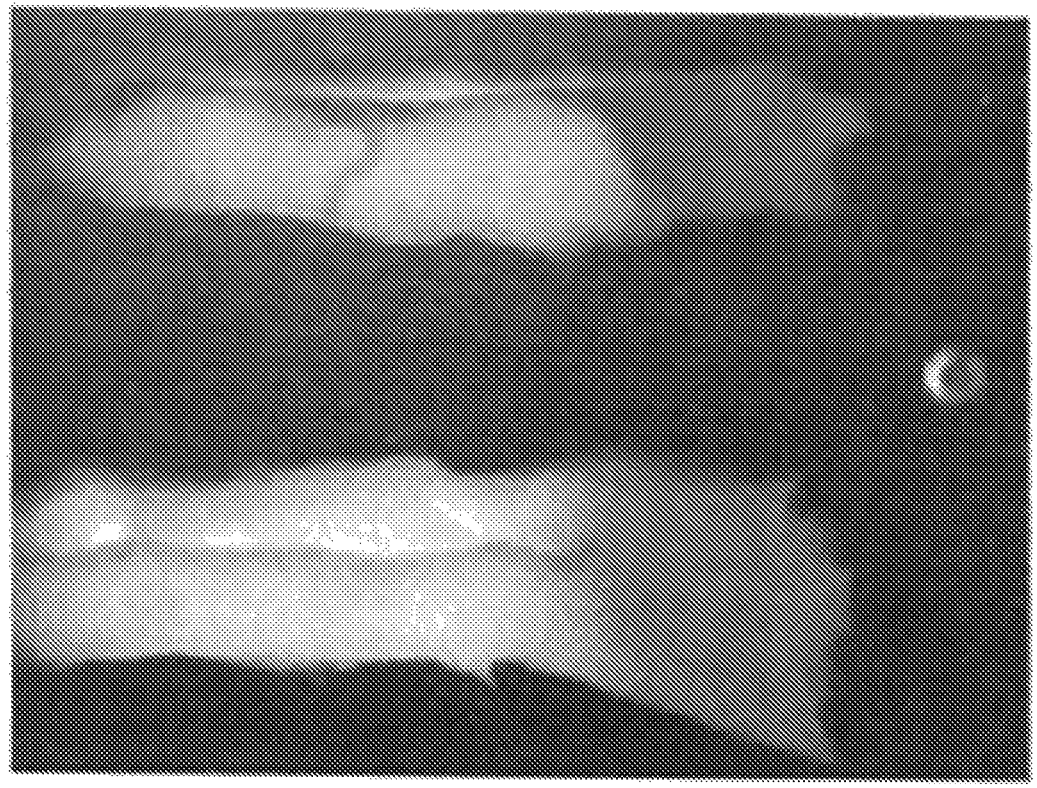
Figure 26C:
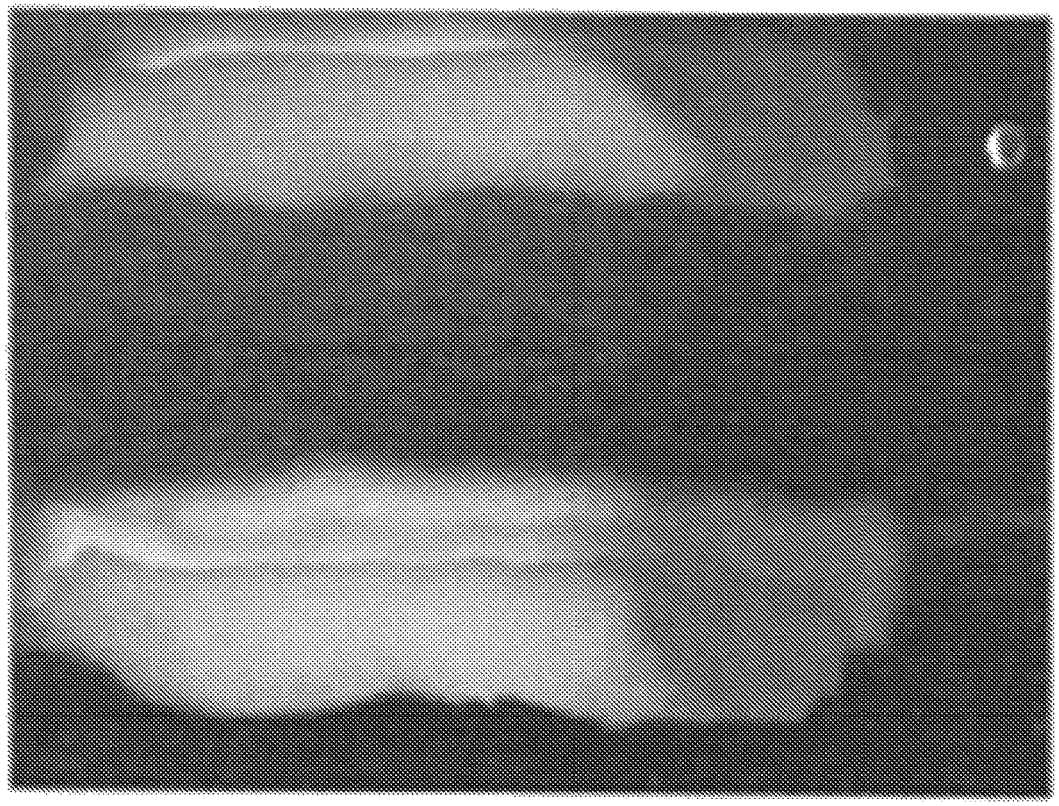

FIGS. 26A-26C depict cellular constructs produced using the parallel bio-printing system 2400 and variations of method 2500A with different pause times and aspiration steps. In particular, FIGS. 26A-26C depict formed cellular constructs each comprising approximately 2.8 µL made up of 0.8 µL of dermal papilla cells and approximately 2.4 µL of keratinocytes, has a substantially straight having a length of approximately 3.2 mm (0.8 mm of dermal papilla cells and 2.4 mm of keratinocytes) and a diameter of approximately 1.0 mm. FIG. 26A depict a formed cellular construct wherein at step 2507 of method 2500A, the pre-determined amount of time paused is approximately 120 seconds. By contrast, FIG. 26B depict a formed cellular construct wherein at step 2507 of method 2500A, the pre-determined amount of time paused is approximately 10 seconds. Significantly and unexpectedly, FIG. 26A has visibly less streaking than FIG. 24B, suggesting that the pausing step at step 2507 (or step 2511) can help significantly reduce the streaking problem.

The streaking problem was found to be reoccurring issue when there was a delayed flow of the bioinks, such as the first bio-ink 2402 or the second bio-ink 2404, through the needles. Long after the piston from the dispenser, such as the first dispenser 2401 or the second dispenser 2403, has stopped actuating, bio-inks continues to flow out of the dispense tip. When bio-printing the target cellular construct, the delayed flow causes some of the first bio-ink 2402 to be dispensed concurrently with the second bio-ink 2404. The result is the streaking of the first bio-ink 2402 into the target region for the second bio-ink 2404. Additionally, when multiple cellular constructs are printed consecutively, the delayed flow of the second bio-ink 2404 from one cellular construct ends up streaking into the target region of the first bio-ink 2402 in the subsequent cellular construct. The solution for the delayed flow is the addition of the pausing step, such as steps 2507 or 2511, after each dispense of the respective bio-ink. With this modification, the streaking behavior is greatly reduced, since ample time is given to the bio-ink to flow into its designated region.

FIG. 26C depict a formed cellular construct wherein at step 2507 of method 2500A, the pre-determined amount of time paused is approximately 10 seconds, and at step 2508, the first dispense tip 2411 aspirates a pre-determined amount of 1.2 µL of the first bio-ink 2402. Significantly and unexpectedly, FIG. 26C has visibly less streaking than FIGS. 26A-26B, suggesting that the addition of the aspiration step at step 2508 (or steps 2512, step 2015) can help significantly reduce the streaking problem.

Figure 27B:
FIGS. 27A-27D depict cellular constructs produced using the parallel bio-printing systems and methods with and without an aspiration step.
Figure 27A:
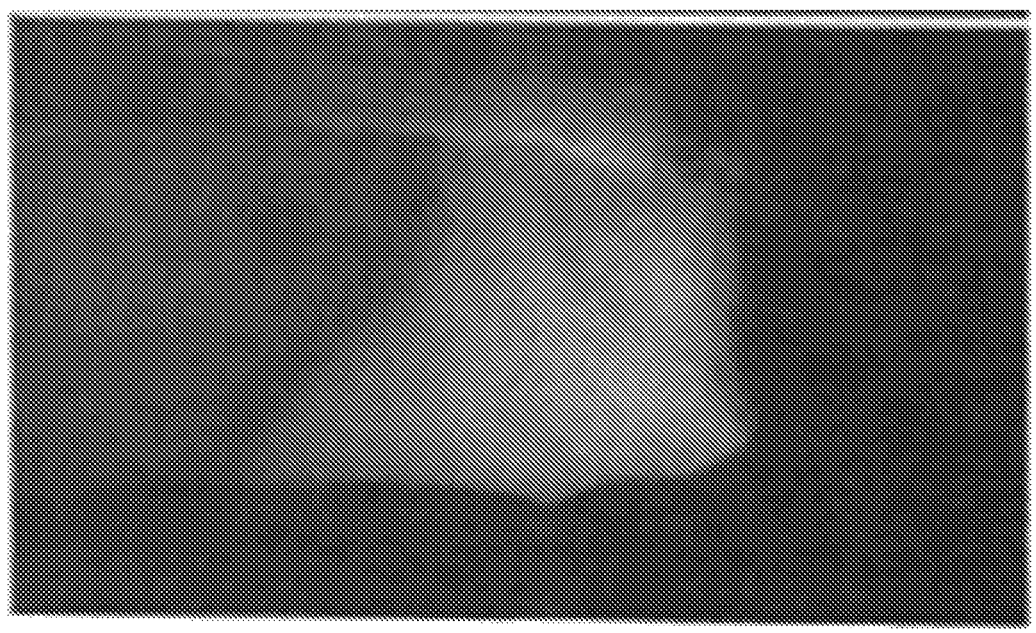
Figure 27D:
Figure 27C:
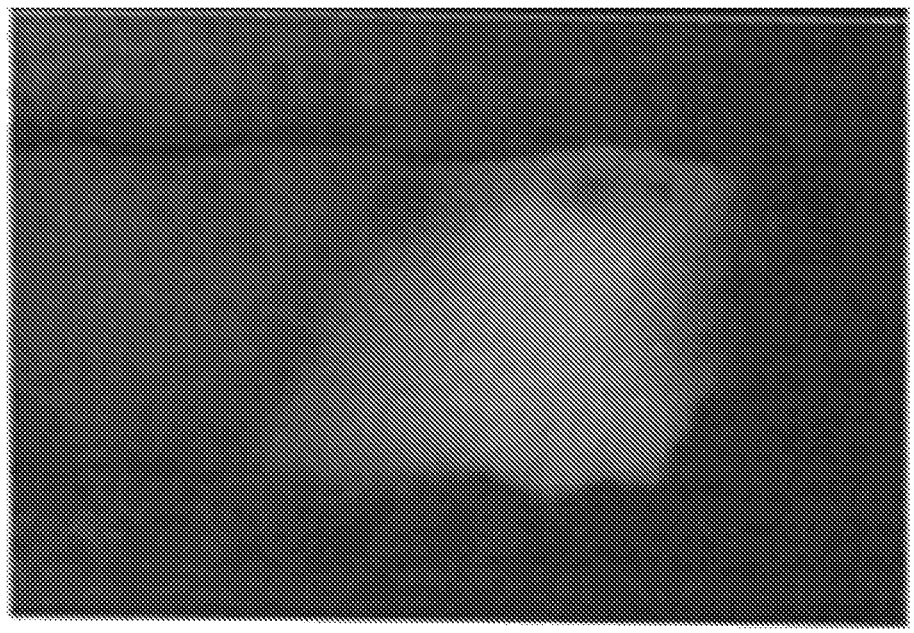

FIGS. 27A-27D depict cellular constructs produced using the parallel bio-printing system 2400 and variations of method 2500A with and without the aspiration step 2508. FIGS. 27A-27D depict formed cellular constructs each comprising approximately 2.8 µL made up of 0.8 µL of dermal papilla cells and approximately 2.4 µL of keratinocytes, has a substantially straight having a length of approximately 3.2 mm (0.8 mm of dermal papilla cells and 2.4 mm of keratinocytes) and a diameter of approximately 1.0 mm. FIGS. 27A-27B depicts a formed cellular construct wherein at the optional step 2515, the first dispense tip 2411 aspirates a pre-determined amount of 1.2 µL of the second bio-ink 2404. This aspiration step helps reduce the streaking of the second bio-ink 2404 when the first bio-ink 2402 is dispensed in the second cycle of method 2500A. By contrast, FIGS. 27C-27D depicts a formed cellular construct wherein the optional step 2515 is omitted. Significantly and unexpectedly, FIGS. 27A-27B does not visibly show the streaking of the second bio-ink 2404 in the first bio-ink 2402, which suggests that the aspiration step is a key step in reducing the streaking problem and immediately halting the flow of unwanted bio-inks. As shown in FIGS. 26C and 27A-27D, aspiration is another key feature that can reduce the streaking of unwanted bio-inks. The aspiration step (i.e. steps 2508, 2512, 2515) can be a complement to the pausing step (i.e. pausing steps 2507, 2511), as shown in FIG. 24C, or an aspiration step without the pausing step, as shown in FIGS. 27A-27D. If the aspiration step is utilized without the pausing step, it can be advantageous because the pausing step adds time, sometimes as long as minutes, needed to execute the method of 2500A or 2500B, thus reducing throughput. By contrast, aspiration adds only a few seconds to the time needed to execute the method of 2500A or 2500B. Additionally, aspiration is advantageous over the pausing because aspiration has shown to be able to immediately halt the flow of unwanted bio-inks.

Figure 28B:
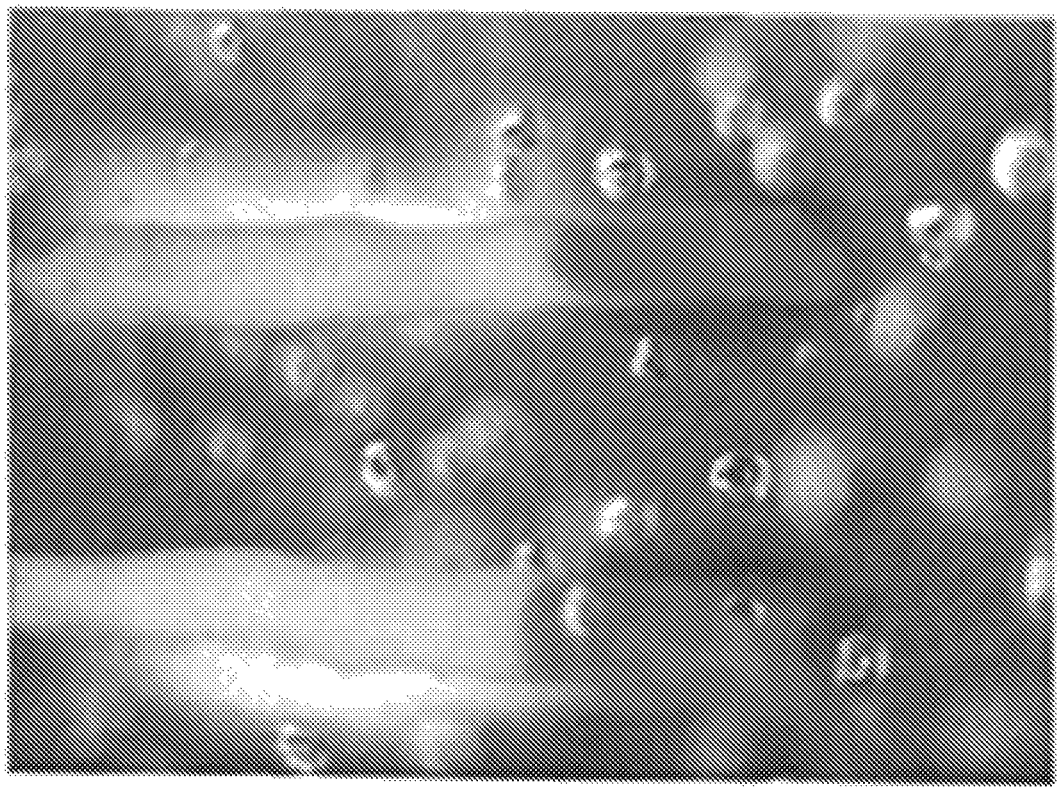
FIGS. 28A-28D depict cellular constructs produced using the parallel bio-printing systems and methods with and without an ascending step.
Figure 28A:
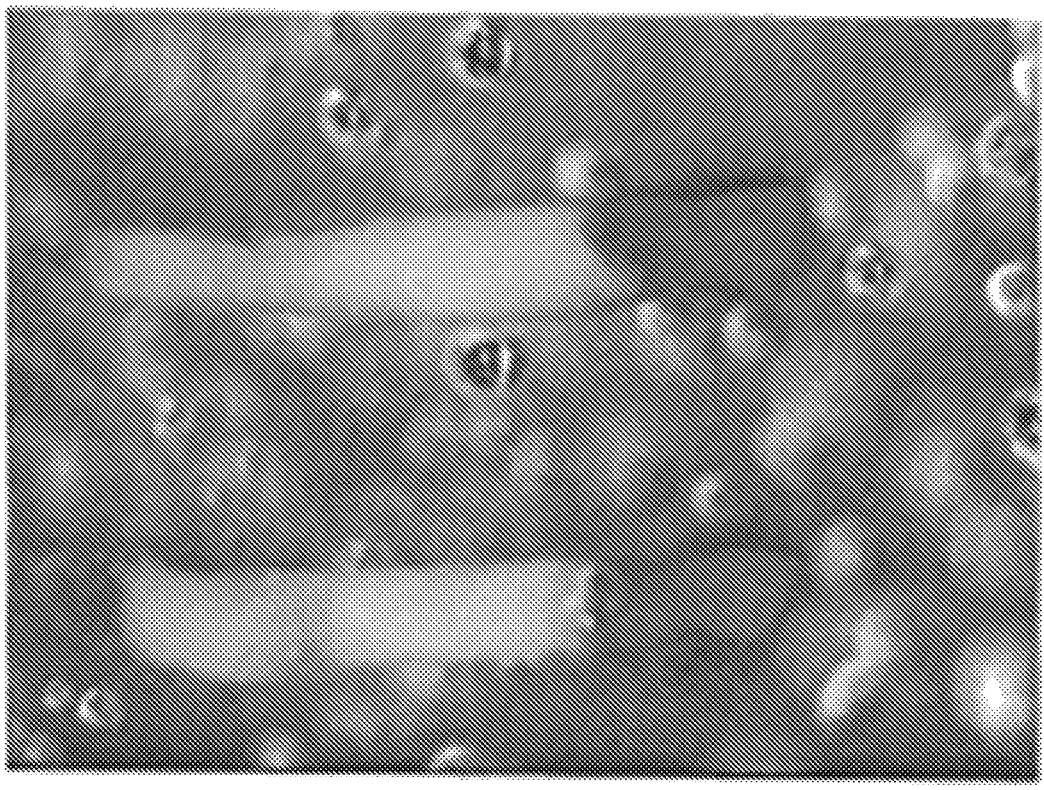
Figure 28D:
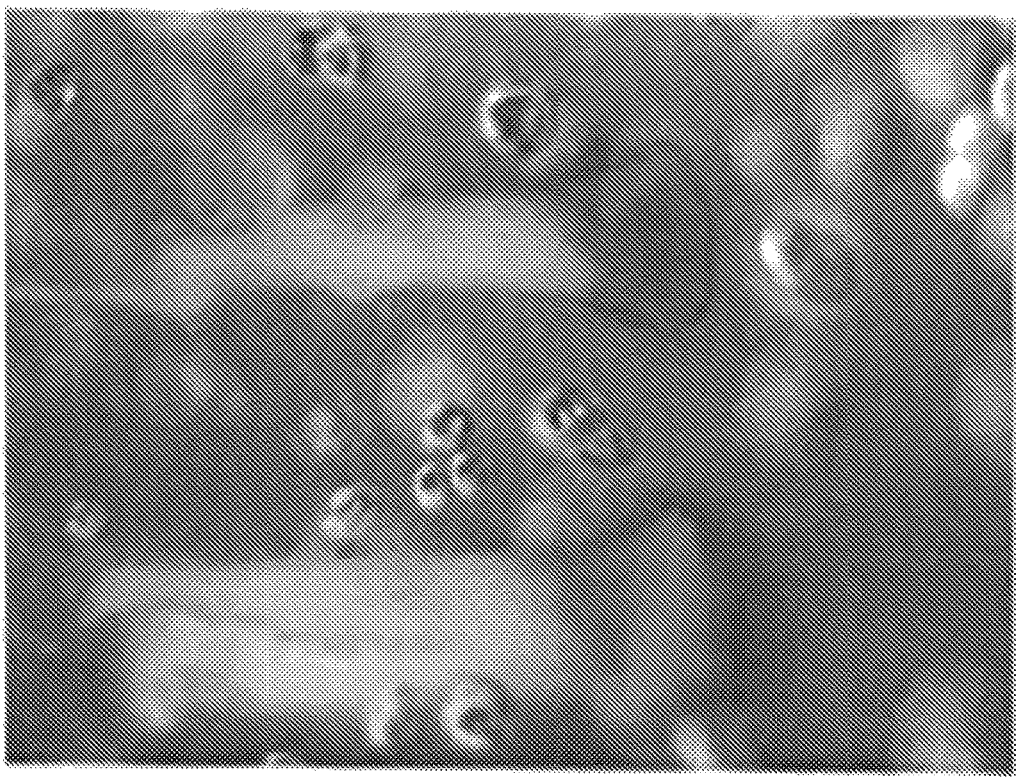
Figure 28C:
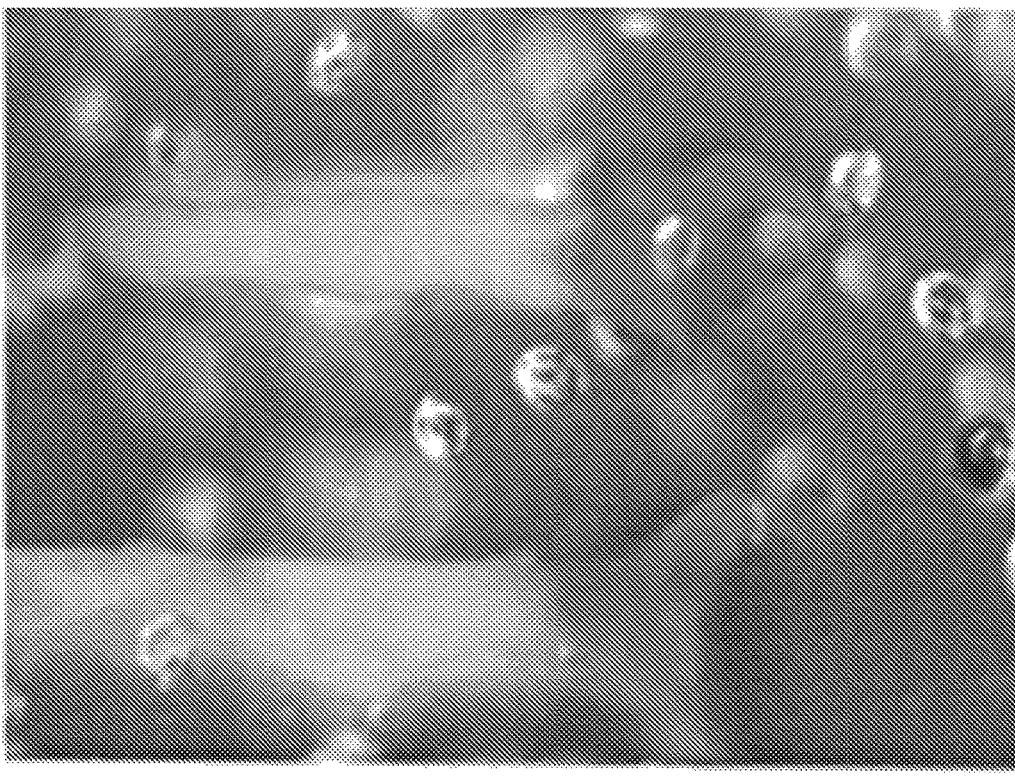

FIGS. 28A-28D depict cellular constructs produced using the parallel bio-printing systems 2400 and variations of methods 2500A with and without the ascending step 2504. FIGS. 28A-28D depict formed cellular constructs each comprising approximately 2.8 µL made up of 0.8 µL of dermal papilla cells and approximately 2.4 µL of keratinocytes, has a substantially straight having a length of approximately 3.2 mm (0.8 mm of dermal papilla cells and 2.4 mm of keratinocytes) and a diameter of approximately 1.0 mm. In particular, the cellular construct of FIGS. 28A-28B is produced with ascending step 2504. By contrast, the cellular construct of FIGS. 28C-28D is produced without ascending step 2504. In this example, at step 2504 of method 2500A, the common outlet 2408 ascends a pre-determined distance of approximately 1.5 mm. Significantly and unexpectedly, FIGS. 28A-B show no budging morphology of the first bio-ink 2402 whereas than FIGS. 28C-D shows the first-bio-ink budging outward radially from the needle axis. This outward budging is not desired because it can potentially facture the surrounding semi-solid material, which acts as support material to help the first bio-ink and the second bio-ink form the cellular construct. Therefore, the ascending step 2504 significantly reduces and/or eliminates the undesired budging morphology of the first bio-ink 2402.

Figure 29B:
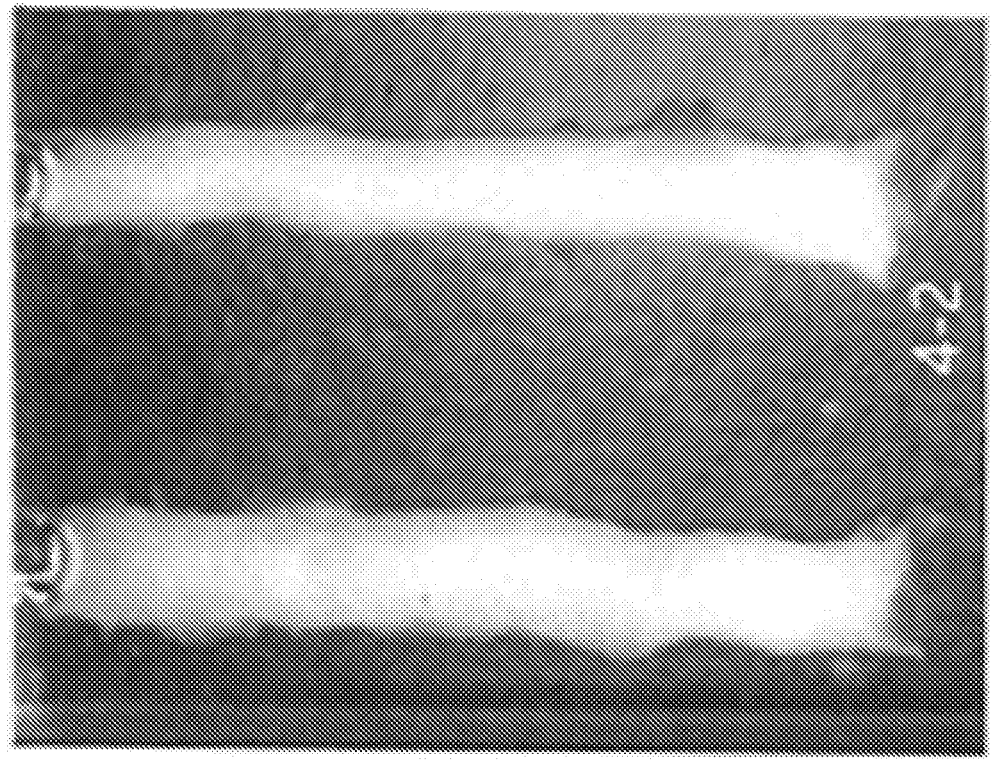
FIGS. 29A-29B depict cellular constructs produced using the parallel bio-printing systems and methods with and without a moving step.
Figure 29A:
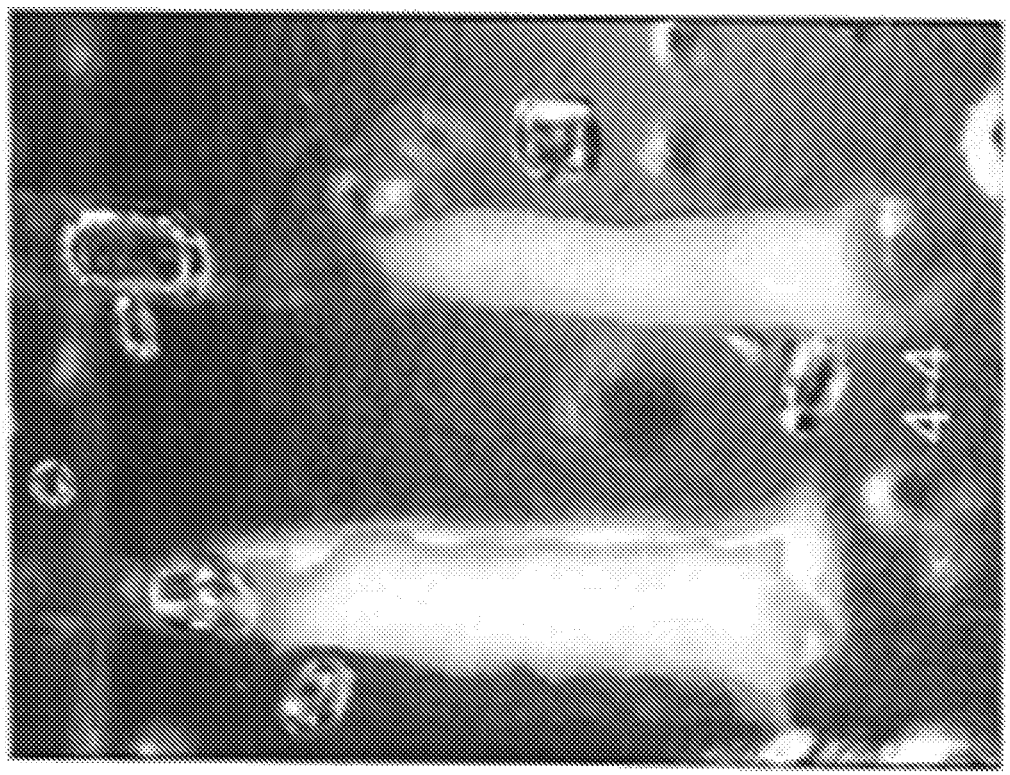

FIGS. 29A-29B depict cellular constructs produced using the parallel bio-printing systems 2400 and variations of method 2500A with and without a moving step 2513. FIGS. 26A-26C depict formed cellular constructs each comprising approximately 2.8 µL made up of 0.8 µL of dermal papilla cells and approximately 2.4 µL of keratinocytes, has a substantially straight having a length of approximately 3.2 mm (0.8 mm of dermal papilla cells and 2.4 mm of keratinocytes) and a diameter of approximately 1.0 mm. FIG. 29A depict the cellular constructs produced with moving step 2513. By contrast, FIG. 29B depict the cellular constructs produced without moving step 2513. At step 2513, the common outlet 2408 moves a pre-determined length of approximately 0.3 mm horizontally, and subsequently, common outlet 2408 moves vertically out of the semi-solid material 2501.

Significantly and unexpectedly, the FIG. 29A produces a cellular construct that is significantly shorter and has less stretched construct. FIG. 29B shows that the cellular construct becomes stretched to more than twice its original bio-printed length, which is not desired. The hypothesized cause for this unwanted stretching may be suction. Assuming that the semi-solid material forms an airtight seal around the dispense tips (i.e. first dispense tip 2411 and second dispense tip 2414), the retracting dispense tips introduces a lower pressure cavity that sucks up the deposited cellular construct that lies below. Thus, the additional step of the approximately 0.3 mm horizontal movement before the final ascending step out of the semi-solid material eliminated the stretching issue shown in FIG. 29B. Whereas previously the semi-solid material formed an airtight seal around the dispense tips, the horizontal 0.3 mm move forces open an air channel down to the dispense tips, preventing a low pressure cavity from forming, as shown in FIG. 29A.

While preferred embodiments of the present invention have been shown and described herein, it will be obvious to those skilled in the art that such embodiments are provide by way of example only. Numerous variations, changes and substitutions will occur to those skill in the art without departing from the invention. All patents, patent applications and publications cited herein are fully incorporated by reference herein.

What is claimed is:

1. A composition comprising a hydrogel comprising a plurality of channels comprising removable cellular constructs that comprise cysts capable of growing hair, wherein each cellular construct is in the form of a column comprising mesenchymal cells and epithelial cells, and wherein the mesenchymal cells comprise dermal papilla cells and the epithelial cells comprise keratinocytes.

2. The composition of claim 1, wherein:
   (a) the hydrogel, cellular constructs and/or the channels further comprise at least one additional cell type;
   (b) the hydrogel, cellular constructs and/or the channels comprise at least one hair follicle maturation factor that is a fibroblast growth factor (FGF), a Wnt agonist, or a combination thereof;
   (c) the cellular constructs further comprise melanocytes;
   (d) the cellular constructs are substantially straight or curved;
   (e) the surfaces of the cellular constructs are irregular;
   the mesenchymal cells are segmented at one end of the cellular constructs and the epithelial cells are segmented at the other end of the cellular constructs;
   (g) the cellular constructs are about 50 μm to about 10,000 μm in length and about 50 μm to about 2000 μm in diameter, or about 4 mm to about 10 mm in length and about 50 μm to about 750 μm in diameter;
   (h) the ratio of mesenchymal cells to epithelial cells is 10:1 to 1:10, or 1:2 to 1:1;
   (i) the mesenchymal and epithelial cells are human cells;
   (j) the hydrogel comprises collagen, hyaluronic acid or salt thereof, fibrin, alginate, agarose, chitosan, or a combination thereof;
   (k) the hydrogel is cross-linked; or
   (l) a combination thereof.

3. The composition of claim 2, wherein the FGF of (b) is FGF5, FGF7, FGF9, FGF10, or a combination thereof, and the Wnt agonist of (b) is CHIR99021, LiCl, SB-216763, CAS 853220-52-7, or a combination thereof.

4. The composition of claim 2, wherein the hydrogel of (j) and/or (k) comprises alginate.

5. A kit comprising the composition of claim 1 and (a) instructions for use of the kit, or (b) instructions for use of the kit and an instrument to implant the cellular constructs.

6. A method of making the composition of claim 1, comprising depositing mesenchymal cells comprising dermal papilla cells and epithelial cells comprising keratinocytes into a hydrogel, wherein the depositing forms a plurality of channels in the hydrogel comprising the mesenchymal cells and the epithelial cells, and culturing the hydrogel comprising the plurality of channels comprising the mesenchymal cells and the epithelial cells to produce removable cellular constructs in the channels that comprise cysts capable of growing hair, wherein each cellular construct is in the form of a column comprising the mesenchymal cells and epithelial cells.

7. The method of claim 6, wherein the hydrogel comprising the plurality of channels comprising the mesenchymal cells and epithelial cells is cultured for 1 to 42 days or 7 to 21 days.

8. The method of claim 6, wherein the depositing comprises inserting a needle into the hydrogel and then withdrawing the needle while concurrently extruding a mixture of the mesenchymal cells and epithelial cells from the tip of the needle.

9. The method of claim 8, wherein the mesenchymal cells are segmented at the tip of the needle.

10. The method of claim 9, wherein the mesenchymal cells are deposited from the tip of the needle and then the epithelial cells are deposited from the needle to provide a segmented cell construct with the mesenchymal cells at the bottom end of the channels and the epithelial cells at the top end of the channels.

11. The method of claim 10, wherein the needle is first loaded with epithelial cells and then the needle is loaded with mesenchymal cells at the tip of the needle prior to deposition of the cells.

12. The method of claim 8, wherein the needle is a co-axial device having two or more separate material pathways providing concentric flow around a common axis of at least two different inputs for at least two different types of cells, wherein the mesenchymal cells are extruded from the core and the epithelial cells are extruded from a mantle layer of the coaxial needle.

13. The method of claim 12, wherein the mesenchymal cells are deposited from the core of the needle and then the epithelial cells are deposited from the mantle layer of the coaxial needle to provide a segmented cell construct with the mesenchymal cells at the bottom end of the channels and the epithelial cells at the top end of the channels.

14. The method of claim 6, wherein:
   (a) the mesenchymal cells and epithelial cells are deposited as part of one or more compositions further comprising an extrusion compound that comprises alginate, a hydrogel, a collagen, extracellular matrix components, or a water soluble, cross-linkable, biodegradable polymer;
   (b) the deposition is controlled by an automated device comprising at least one needle and one or more reservoirs in fluid communication with the needle and a means for extruding the contents of the at least one needle, wherein the one or more reservoirs comprise mesenchymal cells, epithelial cells or mixtures thereof, and an actuation means that positions the needle relative to the surface of the hydrogel;
   (c) the mesenchymal and epithelial cells are human cells;
   (d) the epithelial cells are not deposited as spheroids;
   (e) the hydrogel is cross-linked; or
   (f) a combination thereof.

15. The method of claim 14, wherein the automated device in (b) deposits a plurality of constructs in the hydrogel and/or wherein the automated device comprises a computer processor communicatively connected to the means for extruding the contents of the at least one needle.

16. The method of claim 14, wherein the needle in (b) is beveled.

17. The method of claim 16, wherein the needle is beveled about 10 degrees to about 45 degrees, or about 30 degrees.

18. The method of claim 14, wherein the inner diameter of the needle in (b) is about 150 μm to about 1000 μm.

19. The method of claim 18, wherein the outer diameter of the needle is about 250 μm to about 1250 μm.

20. A method of producing a cellular construct in the form of a column comprising mesenchymal cells and epithelial cells, comprising removing the cellular construct from the composition of claim 1.

21. The method of claim 20, wherein:
   (a) the cellular construct further comprises melanocytes;
   (b) the cellular construct is substantially straight or curved;
   (c) the surfaces of the cellular construct are irregular;

(d) the mesenchymal cells are segmented at one end of the cellular construct and the epithelial cells are segmented at the other end of the cellular construct;

(e) the cellular construct is about 50 μm to about 10,000 μm in length and about 50 μm to about 2000 μm in diameter, or about 4 mm to about 10 mm in length and about 50 μm to about 750 μm in diameter;

(f) the ratio of mesenchymal cells to epithelial cells is 10:1 to 1:10, or 1:2 to 1:1;

(g) the mesenchymal and epithelial cells are human cells; or (h) a combination thereof.

22. A method of hair restoration in an individual, comprising removing at least one cellular construct from the composition of claim 1, and implanting the at least one cellular construct into the skin of the individual.

23. The method of claim 22, wherein the skin is the scalp and/or wherein the implantation is manual or automated.

* * * * *